(12) United States Patent
Savoy et al.

(10) Patent No.: US 11,131,615 B2
(45) Date of Patent: Sep. 28, 2021

(54) SENSOR AND METHODS FOR DETECTING AND QUANTIFYING IONS AND MOLECULES

(71) Applicant: Nanohmics, Inc., Austin, TX (US)

(72) Inventors: Steve M Savoy, Austin, TX (US); Elzbieta A Ledwosinska, Austin, TX (US); Jeremy J John, Austin, TX (US); Kyle W Hoover, Austin, TX (US); Daniel R Mitchell, Austin, TX (US); Chris W Mann, Austin, TX (US); Alexander P Greis, Austin, TX (US)

(73) Assignee: Nanohmics, Inc., Austin, TX (US)

(*) Notice: Subject to any disclaimer, the term of this patent is extended or adjusted under 35 U.S.C. 154(b) by 186 days.

(21) Appl. No.: 16/434,172

(22) Filed: Jun. 6, 2019

(65) Prior Publication Data

US 2019/0383720 A1    Dec. 19, 2019

Related U.S. Application Data

(60) Provisional application No. 62/681,829, filed on Jun. 7, 2018.

(51) Int. Cl.
*G01N 15/06* (2006.01)
*G01N 15/00* (2006.01)

(52) U.S. Cl.
CPC ..... *G01N 15/0606* (2013.01); *G01N 15/0656* (2013.01); *G01N 2015/0053* (2013.01)

(58) Field of Classification Search
CPC ........... G01N 15/0656; G01N 15/0606; G01N 27/06; G01N 33/18; G01N 2015/0053; G01N 2015/0687
See application file for complete search history.

(56) References Cited

U.S. PATENT DOCUMENTS 4,542,640 A    9/1985  Cliford
4,878,015 A *  10/1989  Schmidt ............... G01N 27/414
                                                    324/71.5
(Continued)

FOREIGN PATENT DOCUMENTS

WO    2006113618 A1    10/2006
WO    2010135834 A1    12/2010
(Continued)

OTHER PUBLICATIONS

Fine et al, "Metal Oxide Semi-Conductor Gas Sensors in Environmental Monitoring", Sensors, vol. 10, pp. 5469-5502, (Jun. 1, 2010).

(Continued)

*Primary Examiner* — Benjamin R Schmitt
(74) *Attorney, Agent, or Firm* — Murphy Strategic IP; George L. Murphy

(57) ABSTRACT

An apparatus comprises a housing defining a chamber that has a liquid disposed therein, and a sensor submerged in the liquid. The sensor comprises a porous conductive film on a substrate, and the film comprises chemiresistive semiconducting metal oxide structures. The sensor also comprises an electrode pair operably connected to the porous conductive film for generating electric current in the film and for detecting a change in an electrical property of the film. The apparatus can be used to detect, identify, and quantify ions and molecules in a liquid sample. Molecules and ions, in a liquid sample, that interact with the porous conductive film can cause a change in an electrical property of the film. The change in electrical property of the film can be correlated with the presence and amount of the molecules or ions.

26 Claims, 28 Drawing Sheets

(56) References Cited

U.S. PATENT DOCUMENTS

| | | | |
|---|---|---|---|
| 5,045,285 | A | 9/1991 | Kolesar, Jr. |
| 5,106,756 | A | 4/1992 | Zaromb |
| 5,922,183 | A | 7/1999 | Rauh |
| 7,575,933 | B2 | 8/2009 | Gabriel et al. |
| 8,114,591 | B2 | 2/2012 | Toumazou et al. |
| 8,443,647 | B1 | 5/2013 | Kolmakov |
| 8,563,240 | B2 | 10/2013 | Su et al. |
| 8,685,228 | B2 | 4/2014 | Toumazou et al. |
| 8,698,211 | B2 | 4/2014 | Toumazou et al. |
| 9,670,538 | B2 | 6/2017 | Huff et al. |
| 2004/0161370 | A1 | 8/2004 | Sunshine et al. |
| 2004/0189311 | A1* | 9/2004 | Glezer .............. C12Q 1/001 324/444 |
| 2006/0137669 | A1 | 6/2006 | Lindner |
| 2006/0263763 | A1 | 11/2006 | Simpson et al. |
| 2011/0179852 | A1 | 7/2011 | Polonsky et al. |
| 2012/0178199 | A1 | 7/2012 | Savoy et al. |
| 2012/0245055 | A1 | 9/2012 | Savoy et al. |
| 2012/0270205 | A1* | 10/2012 | Patel .............. G01N 27/126 435/5 |
| 2013/0197319 | A1 | 8/2013 | Monty et al. |
| 2014/0220706 | A1* | 8/2014 | Belbruno .......... G01N 33/182 436/501 |
| 2017/0095841 | A1 | 4/2017 | Ball et al. |
| 2017/0160221 | A1 | 6/2017 | Savoy et al. |
| 2017/0160227 | A1 | 6/2017 | Savoy et al. |
| 2017/0343538 | A9 | 11/2017 | Savoy et al. |
| 2017/0363600 | A9 | 12/2017 | Savoy et al. |
| 2018/0037952 | A1 | 2/2018 | Goldsmith |

FOREIGN PATENT DOCUMENTS

| | | |
|---|---|---|
| WO | 2011154362 A1 | 12/2011 |
| WO | 2012058096 A1 | 5/2012 |
| WO | 2017209839 A1 | 12/2017 |

OTHER PUBLICATIONS

Kanan et al, "Semiconducting Metal Oxide Based Sensors for Selective Gas Pollutant Detection", Sensors, vol. 9, pp. 8158-8196, (Oct. 16, 2009).

Kim et al, "Advances and new directions in gas-sensing devices", Acta Materialia, vol. 61, pp. 974-1000, (2013).

Korotcenkov et al, "Engineering approaches for the improvement of conductometric gas sensor parameters Part 1. Improvement of sensor sensitivity and selectivity (short survey)", Sensors and Actuators B:Chemical, vol. 188, pp. 709-728, (Aug. 7, 2013).

Becker et al, "Gas sensing properties of thin- and thick-®lm tin-oxide materials" Sensors and Actuators B, vol. 77, pp. 55-61, (2001).

Farahani et al, "Humidity Sensors Principle, Mechanism, and Fabrication Technologies: A Comprehensive Review", Sensors, vol. 14, pp. 7881-7939, (Apr. 30, 2014).

Gurrala et al, "Novel pH sensing semiconductor for point-of-care detection of HIV-1 viremia", Nature Sci Reports, vol. 6:36000, pp. 1-6, (Nov. 10, 2016).

Heather et al, "The sequence of sequencers: The history of sequencing DNA", Genomics, vol. 107, pp. 1-8 (Nov. 10, 2015).

Korotcenkov, "Metal oxides for solid-state gas sensors: What determines our choice?", Mater Sci Eng B, vol. 139, pp. 1-23, (2007).

Korotcenkov et al, "Material Design for Metal Oxide Chemiresistive Gas Sensors", J Sensor Sci Technol, vol. 22(1), pp. 1-17, (2013).

Ma et al, "Effect of Water Vapor on Pd-Loaded $SnO_2$ Nanoparticles Gas Sensor", Appl Mater Interfaces, vol. 7, pp. 5863-5869, (2015).

Miller et al, "Nanostructured Tin Dioxide Materials for Gas Sensor Applications", in Functional Nanomaterials, American Scientific Publishers (Valencia, CA USA), KE Geckeler and E Rosenberg eds, Chapter 30, pp. 1-24, (2006).

Pourmand et al, "Direct electrical detection of DNA synthesis", PNAS, vol. 103(17), pp. 6466-6470, (Apr. 25, 2006).

Rothberg et al, "An integrated semiconductor device enabling non-optical genome sequencing", Nature, vol. 475, pp. 348-352 (Jul. 21, 2011).

Seo et al, "Development of inlaid electrodes for whole column electrochemical detection in HPLC", Lab Chip, vol. 9, pp. 2238-2244, (2009).

Shankar et al, "Gas sensing mechanism of metal oxides: The role of ambient atmosphere, type of semiconductor and gases—A review", ScienceJet, vol. 4(126), pp. 1-18, (Oct. 8, 2014).

Sun et al, "Metal Oxide Nanostructures and Their Gas Sensing Properties: A Review", Sensors, vol. 12, pp. 2610-2631, (Feb. 27, 2012).

Wang et al, "Metal Oxide Gas Sensors: Sensitivity and Influencing Factors", Sensors, vol. 10, pp. 2088-2106, (Mar, 15, 2010).

* cited by examiner

SENSOR AND METHODS FOR DETECTING AND QUANTIFYING IONS AND MOLECULES

This application claims priority under 35 U.S.C. § 119 to U.S. Provisional Application No. 62/681,829 filed Jun. 7, 2018, which is incorporated by reference herein in its entirety.

STATEMENT REGARDING FEDERALLY SPONSORED RESEARCH

The invention was made, in part, with government support under National Cancer Institute Contract HHSN261201600035C, U.S. Defense Health Agency Contract W81XWH-14-C-0155, and U.S. Army contract W81XWH-17-C-0166. The government has certain rights in the invention.

FIELD OF THE INVENTION

The invention is related to a chemiresistive semiconducting metal oxide sensor and methods for making and using the sensor for the detection and quantification of nongaseous, ions and molecules in a liquid sample.

GENERAL DESCRIPTION

U.S. patent application Ser. No. 15/372,343, titled "Methods For Detecting and Quantifying Analytes Using Ionic Species Diffusion", which was filed on Dec. 7, 2016 and published on Jun. 8, 2017 as Pub. No. US 2017/0160227 and which received a notice of allowance on Apr. 8, 2019, describes the use of a chemiresistive semiconducting metal oxide sensor for detecting molecules and ions in a liquid. U.S. patent application Ser. No. 15/372,343 is incorporated by reference herein in its entirety.

Detection and quantification of nongaseous molecules, including ions and molecules, are useful in numerous applications. Exemplary applications include monitoring the progress of a chemical reaction, monitoring reaction end-product yield during industrial chemical production and petrochemical refining, analysis of drinking water and wastewater for ions such as fluoride, phosphates, nitrates, sulfates, chlorides, and heavy metals to name a few, and monitoring chemical breakdown products, such as for example breakdown products of chemical and biological weapons for detection of terroristic threats and actions.

Current methods and instruments for detecting ions and molecules include photometric, chromatographic, continuous flow analysis, discrete analysis, mass spectrometry, ion-specific electrodes and potentiometric methods, and atomic absorption/emission spectroscopy. Generally, many methods currently in use require bulky and expensive instrumentation, are labor intensive and slow, and generate significant quantities of waste reagents. In addition, many ion sensors currently in use are selective for specific ions, are incapable of separating and detecting a broad array of different ionic species in a single sample, and have significantly limited detection sensitivities and response times.

Described herein are an apparatus and methods that solve many of the problems associated with currently available sensors and methods for detecting molecules and ions. Embodiments of the invention enable the detection, identification, and quantification of one or more types of nongaseous ions and/or nongaseous molecules in a liquid sample. Unlike currently used instruments and methods, embodiments of the ion and molecule sensor apparatus described herein are capable of rapidly separating and responding to a wide variety of ions and molecules in a liquid sample, thereby enabling detection, identification, and quantification of numerous types of molecules and ions in a single sample. Embodiments provide significant cost savings by eliminating the need for numerous different ion-selective electrodes and reference electrodes such as are used in some of the current sensing methods. Embodiments also enable increased sample throughput and reduce or eliminate the need for manual supervision of instruments as compared to currently used sensors and methods. Sensor apparatus embodiments described herein exhibit faster response times to molecules and ions than are observed with current instruments. Additionally, fabrication of the sensor apparatus described herein is rapid and cost-effective when compared to other sensors in current use, and the sensing apparatus described herein can be easily and readily miniaturized which is not possible with other sensor formats. Miniaturization enables the separation and detection of ions and molecules in novel applications that current methods and sensors are not capable of providing.

The embodiments are useful in a wide variety of applications that benefit from or require detection, identification, and quantification of a nongaseous ion or molecule in a liquid. Some exemplary uses include monitoring the progress or yield of a chemical reaction or a biochemical reaction, such as for example an in vitro chemical or biochemical reaction, analyzing and quantifying biomarkers, such as for example biomarkers present in a blood sample, a sweat sample, or other biological fluid sample. In some embodiments, detection and analysis of ionic and molecular species are useful in electrolyte analyses, by way of example only, for diagnosing dietary deficiencies, excessive nutrient loss, organ failure (e.g. kidney, heart and liver), and hormone production abnormalities. Additional exemplary uses include monitoring reaction end-product yield during industrial chemical production and petrochemical refining, analysis of water or wastewater for the presence or quantity of one or more ionic species, such as for example fluoride, phosphates, nitrates, sulfates, chlorides, and heavy metals to name a few and monitoring chemical breakdown products, such as for example breakdown products of chemical and biological weapons for detection of terroristic threats and actions. Some embodiments are especially useful for applications that require small measuring devices, such as for example a wearable device useful for detection and analysis of ionic and molecular species in sweat or other biological liquid samples that are indicative of mental or physical fatigue or other conditions or diseases and for example a miniaturized device for use within a human or animal body for monitoring any of a variety of types of biological molecules and/or ions.

Chemiresistive semiconducting metal oxide sensors for detecting gases in gaseous samples have been studied extensively (Miller 2007, Fine 2010, Sun 2012). However, chemiresistive semiconducting metal oxides sensors for use in the detection and quantification of ions and molecules in liquids have not been described by others.

In some embodiments, an apparatus for use in detecting molecules and ions comprises (1) a housing defining a chamber, the chamber having a liquid therein, (2) a sensor submerged in the liquid and comprising (i) a porous conductive film made of chemiresistive semiconducting metal oxide structures and positioned on a substrate, and (ii) an electrode pair operably connected to the porous conductive film for generating electric current in the film and for detecting a change in an electrical property of the film. In some embodiments, the chemiresistive semiconducting metal oxide structures comprise either or both of nanostructures and microstructures. In some embodiments, the liquid in which the sensor is submerged is an aqueous liquid, and the aqueous liquid can contain either or both of solvated ions and solvated molecules, which in some embodiments may be analytes. In some embodiments, either or both of the solvated ions and solvated molecules may be adsorbed to the porous conductive film. The sensor may be equilibrated in the submersion liquid.

In some aspects the aqueous liquid can comprise organic molecules. The organic molecules may be either or both of solvated molecules and solvated ions. In some embodiments, the aqueous liquid can be deionized water or can be a buffer solution comprising a mixture of a weak acid and its conjugate base. The apparatus in some aspects, can further comprise a semipermeable barrier positioned so as to divide the chamber into a plurality of subchambers, and the semipermeable barrier may or may not be in contact with the porous conductive film. In some aspects some of the solvated ions and/or molecules may bind to the semipermeable barrier.

The apparatus can optionally contain one or more inlet ports and/or outlet ports. The apparatus may also comprise a wicking material for causing a liquid sample and ions or molecules to move across electrode pairs, and in some embodiments, through the porous conductive film. The apparatus may comprise a semipermeable barrier and may be divided into a plurality of subchambers. Various modifications to the apparatus can be made to alter the diffusion rates of selected ions or molecules so as to enhance the separation of ions and molecules for detection and quantification. In some aspects, enhancing the separation of ions and molecules is accomplished by In some embodiments, the apparatus can be used for analyzing a liquid sample for the presence of and/or amount of one or more molecules and/or ions. In some aspects, the apparatus can be used for monitoring chemical reactions and such monitoring can include measuring the amounts of reaction products, by-products, or breakdown products that are molecules or ions. In some aspects, detection and quantification of molecules and/or ions in a chemical reaction can be used to correlate the presence of selected molecules or ions with the presence of another chemical or chemical compound, such as for example a nucleic acid, protein, or other metabolite. Such correlations can be used to determine the sequence of a nucleic acid or protein and to quantify the amount of an amplified nucleic acid.

The specification is most thoroughly understood in light of the teachings and references cited within the specification. It should be understood that the drawings, detailed description, and specific examples, while indicating specific embodiments of the invention, are given by way of illustration only, since various changes and modifications within the spirit and scope of the invention will become apparent from this detailed description to those skilled in the art.

Any section headings used herein are for organizational purposes only and are not to be construed as limiting the subject matter described. All documents, or portions of documents, cited in this application, including but not limited to patents, patent applications, articles, books, and treatises, are hereby expressly incorporated by reference herein in their entirety for any purpose. To the extent documents, publications, patents, or patent application publications incorporated by reference contradict the invention contained in the specification, the specification will supersede any contradictory material.

BRIEF DESCRIPTION OF THE FIGURES

The following drawings form part of the specification and are included to further demonstrate certain aspects of the invention. The invention may be better understood by reference to one or more of these drawings in combination with the detailed description of the specification embodiments presented herein.

DESCRIPTION OF CERTAIN EXEMPLARY EMBODIMENTS

Figure 1A:
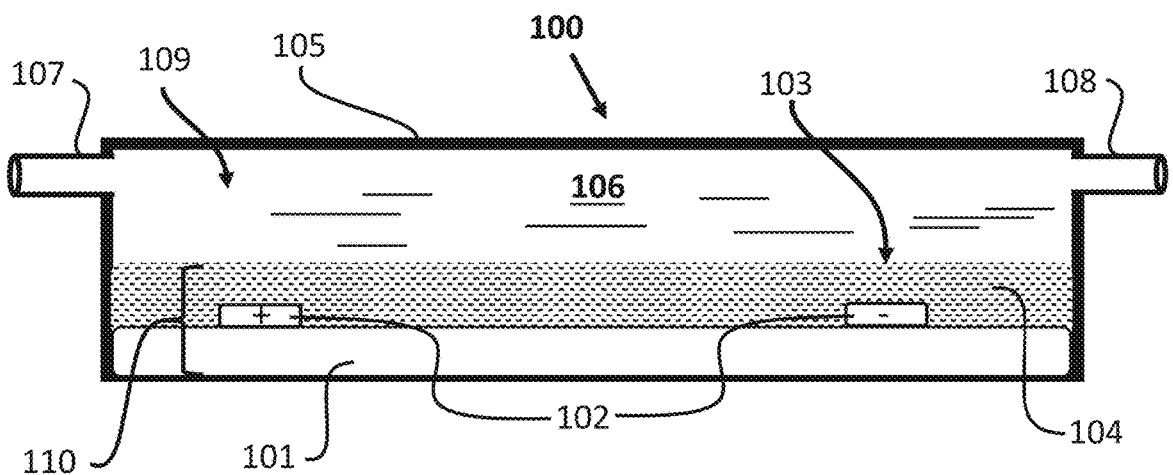
FIGS. 1A-1D illustrate a schematic side view of an exemplary embodiment of an apparatus and depict some aspects of apparatus and sensor operation and a graphical representation of a sensor response profile.
Figure 1B:
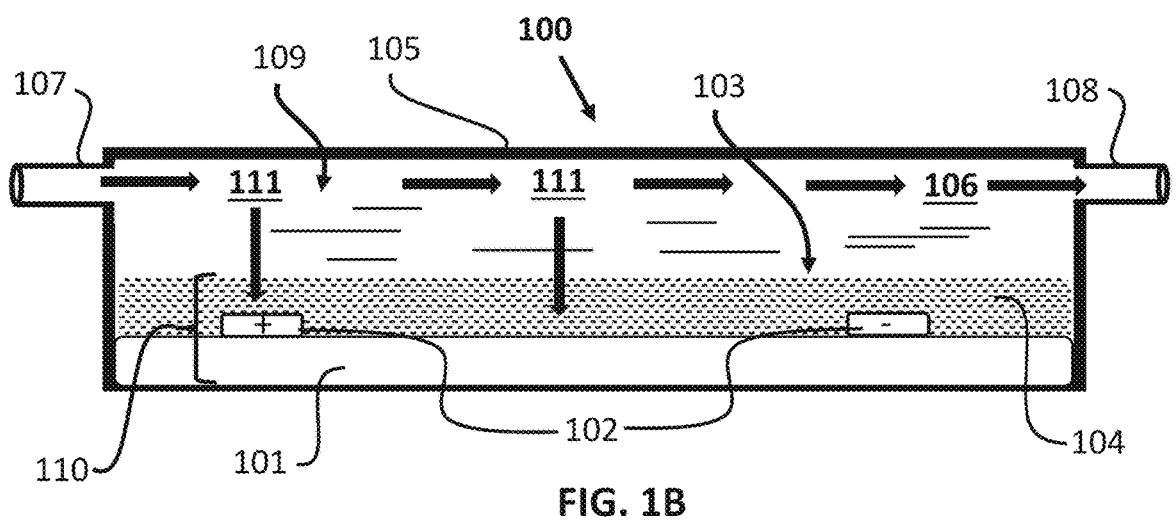

Reference will now be made in detail to certain exemplary embodiments of, some of which are illustrated in the accompanying drawings. To assist in understanding the disclosure, certain terms are first defined. Additional definitions are provided throughout the application.

The use of the word "a" or "an" when used in conjunction with the term "comprising" in the claims or the specification may mean "one," but it is also consistent with the meaning of "one or more," "at least one," and "one or more than one."

The use of the term "at least one" in the specification and claims is meant to include "one or more than one", and the use of the term "one or more than one" is meant to include "at least one".

Throughout this application, the term "about" is used to indicate that a value includes the standard deviation of error for the device or method being employed to determine the value.

The use of the term "or" in the specification may be used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In some aspects, embodiments that "comprise" elements and/or steps, may "consist essentially of," or "consist of" the elements and/or steps disclosed.

The terms "operably associated", "operably coupled", "operably connected", and "operably positioned" may be used interchangeably herein and refer to an operable association between two or more components or elements. For example, components of electrical circuits, devices, and systems are operably associated. Operable association, operable connection, operable coupling, and operable positioning do not necessarily require direct physical connection between specified components.

In some embodiments, the disclosure is related to an apparatus that can be configured for and used for detecting nongaseous ions and molecules in a liquid. In some embodiments the apparatus comprises (a) a housing defining a chamber, the chamber having a liquid therein, (b) a sensor submerged in the liquid and comprising (i) a porous conductive film made of or comprising chemiresistive semiconducting metal oxide ($MO_x$) structures and positioned on a substrate, and (ii) an electrode pair operably connected to the porous conductive film for generating electric current in the film and for detecting a change in an electrical property of the film.

As used herein, the terms "sensor", "ion sensor", and "molecule sensor" can be used interchangeably and refer to a sensor that can be configured and used for detecting either or both of ions or molecules in a liquid or in a sample of liquid. In some embodiments, the sensor can be placed or positioned in a housing that defines a chamber, the chamber having a liquid disposed therein, such that the sensor is submerged in the liquid. In some embodiments, the housing can be positioned over the sensor to define a chamber capable of holding the submersion liquid. In one exemplary embodiment, the housing may be positioned on the substrate, so as to enclose the sensor, and sealed to the substrate to define a leak-proof chamber such that liquid may be disposed within the chamber to submerge the sensor in the liquid.

In some embodiments, an electrical property of a porous conductive film, such as for example conductance or resistance of the film, can be affected by interaction between an ion or molecule present in the liquid disposed in the chamber and the surface of the porous conductive film. As used herein, the surface of a porous conductive film can also mean the surfaces of the $MO_x$ structures in the film, and a surface of an $MO_x$ structure can mean any region of the structure, present in a porous conductive film, that is accessible to interaction with a molecule or ion analyte in a liquid. As used herein, "binding", "adsorbing", and variants thereof refer to the interacting of an ion or molecule analyte with the surface of a $MO_x$ structure in a porous conductive film. In some embodiments, surfaces of $MO_x$ structures can have binding sites that are recognized by selected ions or molecules thereby mediating binding of the analytes to $MO_x$ structures in the film. In some embodiments, the amount or mass of an analyte that can bind to a selected amount or mass of $MO_x$ structures can represent the "binding capacity" of the selected amount of "$MO_x$ structures". In some embodiments, the "binding capacity" can correspond to the number of available binding sites on $MO_x$ structures, for a given analyte.

As used herein, in some aspects, "selected ion or molecule" can refer to a selected "type" or "species" of ion or molecule, and "selected ions or molecules" can refer to a plurality of selected different types or species of ions or molecules. In some aspects, "a plurality of known ion or molecule species" means at least two different types or species of known ions or molecules. In some aspects, "one or more known ion or molecule species" means at least one known species or type of ion or molecule but also can mean at least two types or species of known ion or molecule.

As used herein, an ion or molecule that is under investigation to determine the presence of, identity of, and/or quantity of the ion or molecule is referred to herein as an "ion or molecule analyte", an "analyte", "analyte species" or various combinations of these terms. An ion or molecule analyte may refer to a known species of ion or molecule, such as that which may be present in a control sample, or to a species of ion or molecule analyte whose identity is unknown. In some aspects an analyte may be an ion or molecule that is solvated in a liquid, such as the liquid in which the sensor is submerged (submersion liquid 106) or in a liquid sample that may be added to the chamber.

For brevity, "ion or molecule analyte" is used herein to mean either a molecule, an ion, or both a molecule and an ion and/or a molecule analyte. That is the term "ion or molecule analyte" includes either an ion analyte, or a molecule analyte, or both ion and molecule analytes. For brevity, "ion or molecule" and the plural "ions or molecules" may be used herein to mean an ion and/or a molecule. That is the term "ion or molecule" and the plural form refer to either ions, or molecules, or both ions and molecules.

FIGS. 1A-1D illustrate a schematic side view of an exemplary embodiment of an apparatus and depict some aspects of apparatus and sensor operation and a graphical representation of a sensor response profile during exposure of the sensor to a liquid sample having either or both of ions and molecules for detection. In this exemplary embodiment (FIG. 1A), apparatus 100 comprises porous conductive film 103 positioned on substrate 101, and operably connected to electrode pair 102. Sensor 110 comprises electrode pair 102 and porous conductive film 103 that is positioned on substrate 101 and comprises metal oxide ($MO_x$) structures 104. Porous conductive film 103 comprises $MO_x$ structures 104. In some embodiments, housing 105 can be fitted with an optional inlet port 107 and/or optional outlet port 108 that can provide for fluid communication with chamber 109 for addition and exchange of liquids. In some aspects, housing 105 may be fitted with a plurality of inlet ports 107 that provide for fluid communication with chamber 109. Inlet port 107 and outlet port 108 may be configured to have any of a variety of shapes, such as for example only circular, elliptical, oblong, square, rectangular, or other shape and can be any size useful for adding liquid to or expelling liquid from chamber 109. Here, sensor 110 is submerged in submersion liquid 106 disposed within chamber 109 that is defined by housing 105, and submersion liquid 106 fills the interstitial volume (open spaces) among $MO_x$ structures 104 of porous conductive film 103.

In many embodiments, submersion liquid 106 can be exchanged with a submersion liquid 106 that has a different chemical composition. In some embodiments, the composition of submersion liquid 106 can be selected to cause or enhance an interaction between ions or molecules in submersion liquid 106 with $MO_x$ structures 104 in porous conductive film 103. In some aspects, ions or molecules from submersion liquid 106 may adsorb to $MO_x$ structures 104, which may cause a change in an electrical property of porous conductive film 103. In an exemplary embodiment, adsorbed ions or molecules interact with $MO_x$ structures 104 by binding to available binding sites on $MO_x$ structures 104 thereby causing a change in an electrical property of porous conductive film 103. Similarly, ions or molecules in submersion liquid 106 can interact with $MO_x$ structures 104 by displacing adsorbed molecules or ions that are already interacting with $MO_x$ structures 104, which may cause a change in an electrical property of porous conductive film 103. In one exemplary embodiment, displacement of ions or molecules from binding sites on $MO_x$ structures 104 can be used to establish a baseline conductance in porous conductive film 103.

In some embodiments, ions or molecules are solvated in submersion liquid 106 and may occupy one or more binding sites on the surfaces of $MO_x$ structures 104 of porous conductive film 103. In some aspects, a solvated ion or molecule with a higher binding affinity for $MO_x$ structures 104 of porous conductive film 103 may outcompete one or more other solvated ions or molecules and adsorb to binding sites on the surfaces of $MO_x$ structures 104 of porous conductive film 103, thereby excluding solvated ions or molecules having a lower binding affinity for $MO_x$ structures 104 of porous conductive film 103. Displaced ions or molecules may then become solvated ions or molecules. In some embodiments an excluded or displaced ion or molecule may be moved to a different region of porous conductive film 103 by flow of submersion liquid 106 or by diffusion through submersion liquid 106 and may readsorb to $MO_x$ structures 104 in a different region of porous conductive film 103. In some aspects, an excluded or displaced ion or molecule may itself displace another ion or molecule having a lower binding affinity for $MO_x$ structures 104 in porous conductive film 103. In some embodiments, the composition of submersion liquid 106 can be selected to have ions or molecules that can competitively displace other selected ions or molecules causing ions, such as ions and molecules having a lower binding affinity for $MO_x$ structures 104 in porous conductive film 103.

In some aspects the amount of an ion or molecule adsorbed to $MO_x$ structures 104 in porous conductive film 103 may reflect the amount of available binding sites on the surface of porous conductive film 103. In some embodiments, the amount or mass of an analyte that can bind to a selected amount or mass of $MO_x$ structures can represent the "binding capacity" of the selected amount of $MO_x$ structures 104. In some embodiments, the "binding capacity" can correspond to the number of available binding sites for a given analyte on $MO_x$ structures. Binding capacity can be determined by techniques including, by way of example only, molecular difference titration and BET surface area determination. The mass of $MO_X$ particles with a known number of available binding sites can be used to determine the amount of adsorbed ions or molecules, which mass may then be correlated to the concentration of an ion or molecule analyte 112 in a test sample.

In some embodiments, a submersion liquid can be a liquid that may be used to wash sensor 110. In one exemplary embodiment, depicted schematically in FIG. 1B, submersion liquid 106 is replaced with wash liquid 111. In some aspects, submersion liquid 106 can be replaced or partially replaced with a wash liquid 111. In this exemplary embodiment, wash liquid 111 is introduced into chamber 109 through inlet port 107 causing submersion liquid 106 to be moved from chamber 109 through outlet port 108 (thick arrows represent direction of movement of liquids). In some embodiments, wash liquid 111 can combine with liquid 106 in the interstitial volume among $MO_X$ structures 104 such that ions or molecules in wash liquid 111 can move into liquid 106 by diffusion. In some embodiments, wash liquid 111 can diffuse throughout chamber 109 replacing submersion liquid 106 in the interstitial volume among $MO_X$ structures 104 of porous conductive film 103.

In some aspects, inlet port 107 can be an opening through which a liquid can be added to chamber 109, or inlet port 107 can be a membrane or a wicking fiber in chamber 109 that can enhance addition or attraction of a liquid sample to chamber 109. Useful fluid inlet ports such as for example drop reservoirs, luer lock, press lock, ferruled Swagelock®, well as other structures for fluid communication that may be used for inlet port 107 are known in the art.

Figure 1C:
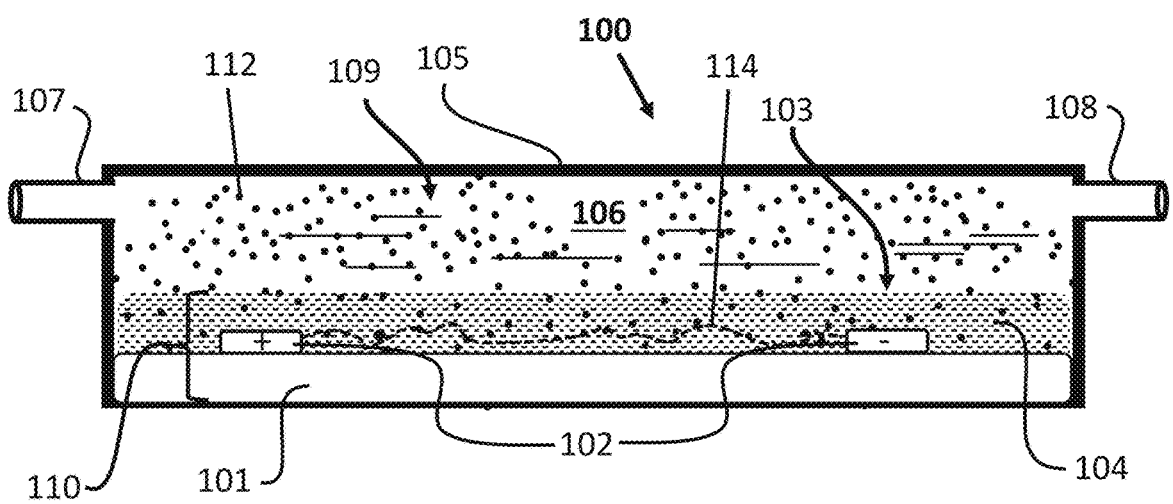

FIG. 1C schematically depicts an exemplary embodiment in which a liquid sample, having the same composition as submersion liquid 106 is added to chamber 109. In this example, ion or molecule analyte 112 is present in liquid 106.

In some embodiments, exposing sensor 110 to a liquid sample can comprise contacting the sensor with the sample by adding the sample to chamber 109 so as to allow for the liquid sample components and any ion or molecule analytes 112 in the liquid sample to diffuse throughout submersion liquid 106 in which sensor 110 is submerged and into the interstitial volume among $MO_X$ structures 104 in porous conductive film 103. In this exemplary embodiment, ion or molecule analyte 112 in the liquid sample is shown as having diffused throughout liquid 106 in chamber 109 and into the interstitial volume of liquid 106 surrounding $MO_X$ structures 104. During operation, a bias voltage is applied to one of the electrodes in electrode pair 102 so as to generate current 114 in porous conductive film 103 between electrodes in electrode pair 102. In some embodiments, as ion or molecule analyte 112 diffuses through liquid 106, interactions between ion or molecule analyte 112 and $MO_X$ structures 104 may involve physisorption and/or chemisorption to binding sites on $MO_X$ structures 104, which can cause a change in an electrical property of porous conductive film 103, resulting in a sensor response. In some aspects, a change in an electrical property can be a measurable change. In some embodiments, a sensor response to an ion or molecule analyte 112 can be affected by the diffusion rate of the ion or molecule analyte 112 in the liquid sample through submersion liquid 106 and throughout porous conductive film 103 and the interstitial volume of the liquid. In some embodiments, the adsorption and/or desorption rate (i.e., the rate at which an ion or molecules analyte adsorbs or desorbs to $MO_X$ structures 104) of ion or molecule analyte 112, may be affected by ion or molecule analytes 112 or by different ions or molecules that may be present in liquid 106. The adsorption and/or desorption rate of ion or molecule analyte 112, may also be affected by different ions or molecules (i.e., ions or molecules that are not analytes) already bound to binding sites on $MO_X$ structures 104. In some aspects, a sensor response to an ion or molecule analyte 112 can be affected by the diffusion rate of the ion or molecule analyte 112 to $MO_X$ structures 104. In some aspects, a sensor response to an ion or molecule analyte 112 can be affected by the Langmuir adsorption and desorption kinetics to $MO_X$ structures 104. In some embodiments, sensor 110 response to an ion or molecule analyte 112 can be affected by the Langmuir adsorption and desorption kinetics to the surface of $MO_X$ structures 104. In some aspects, a sensor response to an ion or molecule analyte 112 can be affected by the exchange rate between adsorbed ion or molecule analytes 112 on the surface of $MO_X$ structures 104 and charge carriers in $MO_X$ structures 104.

In some embodiments, exposing sensor 110 to a liquid sample means exposing porous conductive film 103 to a liquid sample or contacting porous conductive film 103 with a liquid sample. Exposing a sample to sensor 110 can also mean exposing sensor 110 to a sample.

Figure 1D:
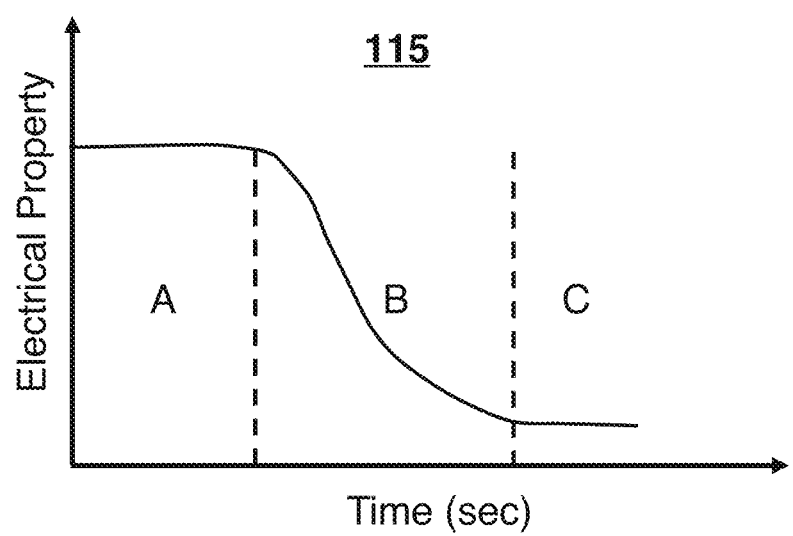

FIG. 1D shows an exemplary graphical plot of sensor response data, a sensor response profile 115, that can be acquired by measuring an electrical property of porous conductive film 103 during analysis of a liquid sample having molecule or ion analyte 112. As used herein, in some embodiments, measuring an electrical property (conductance or resistance) of porous conductive film 103 can also mean measuring or determining a sensor response. In some aspects, "sensor response profile", "sensor response", and "sensor response data" may be used interchangeably and can refer to one or more measurements of an electrical property (e.g., conductance or resistance) of porous conductive film 103 taken at a selected time or for a selected period of time ranging from before exposure of sensor 110 to a liquid sample to a selected period of time after exposure of sensor 110 to the liquid sample. Measurements of electrical properties such as conductance and resistance can be made by the use of devices known to those with skill in the art. In some aspects, sensor response data may be plotted as sensor response (y-axis in FIG. 1D) vs. time (x-axis in FIG. 1D). Sensor response data and graphically depicted sensor response data may also be referred to herein as a "sensor response profile" 115.

In some embodiments, sensor 110 may be equilibrated or substantially equilibrated in submersion liquid 106. In some aspects, sensor 110 that has equilibrated or substantially equilibrated in a liquid (also referred to herein as an "equilibrated sensor") may show no appreciable change over time in an electrical property of porous conductive film 103, i.e., the sensor 110 may show no appreciable change in sensor response 115 over time, such as the substantially unchanging sensor response 115 depicted in region A of sensor response profile 115. Here, region A of sensor response profile 115 corresponds to a time range before ion or molecule analyte 112 interacts with porous conductive film 103 or before sufficient numbers of ion or molecule analytes 112 interact with the film so as to elicit a measurable change in an electrical property of porous conductive film 103. As ion or molecule analyte 112 diffuses into porous conductive film 103, a decrease or increase in the measured electrical property is observed (region B). In time, ion or molecule analytes 112 reach a surface equilibrium concentration with porous conductive film 103 and sensor response 115 stabilizes (region C). In some embodiments, the time required for ion or molecule analytes 112 to reach a surface equilibrium concentration with porous conductive film 103 can be about 1 nanosecond, about 1 microsecond, about 0.00001 s, about 0.0001 s, about 0.001 s, about 0.01 s, about 0.1 s, about 1 s, about 10 s, about 100 s, about 15 minutes, about 2 hours, about 12 hours, or about 2 days. It is specifically contemplated that the amount of time required for an analyte to reach a surface equilibrium concentration with porous conductive film 103 can be any time from about 1 nanosecond to about 2 days, including any time point in that range.

In some embodiments, the time required to reach equilibrium concentration can be affected by one or more of the concentration of ion or molecule analyte 112 in the submersion liquid 106, the diffusion coefficient of ion or molecule analyte 112, the binding affinities of ion or molecule analytes 112 with porous conductive film 103, the composition of submersion liquid 106, the structure of porous conductive film 103, and the presence or absence of a diffusion matrix that may be coupled to $MO_x$ structures 104.

Sensor 110 may be exposed to any of numerous types of liquids or liquid samples for analysis. In some embodiments, a liquid or liquid sample is an aqueous liquid. In some aspects, a liquid sample can comprise deionized water, an aqueous buffer solution, or another type of liquid. In some embodiments, a liquid or liquid sample can be a liquid that is analyzed to determine the presence of, identity of, and/or amount of one or more selected ion or molecule analytes 112 in the liquid. In some embodiments, "determining the presence of" an ion or molecule or "detecting" an ion or molecule can comprise identifying the type or species of an ion or molecule analyte 112 and/or quantifying the amount or concentration of an ion or molecule analyte 112 in a liquid sample.

In some embodiments, a liquid sample can be a liquid "control sample", a "calibration sample", or a liquid "test sample". A control sample can be a liquid sample that may be chosen or prepared so as to lack selected types of ions or molecules or a liquid sample that may be chosen or prepared so as to have selected types of ions or molecules. A "test sample" can be a sample that can be analyzed for the presence and/or quantity of selected types of ion or molecule analytes 112 that may be present in the sample. In some embodiments, one or more known or "control" ion or molecule species in a liquid sample can be selected based on the ion or molecule species 112 to be detected on analysis of a test sample. For example, a known ion or molecule species analyte 112 in a control sample may have a structure or valence that is selected to be similar to, identical to, or specifically different from that of an ion or molecule species analyte 112 that is or is suspected of being in a test sample. In some aspects, a liquid sample being analyzed can comprise a known species of molecule or ion and can also be suspected of having a different species of ion or molecule. In some embodiments, the presence of, identity of, and/or quantity of a selected ion or molecule analyte 112 in a test sample may be unknown. In some aspects, a test sample can comprise a known species of ion or molecule or a known species of ion or molecule may be added to a test sample. In some aspects, a control sample and a test sample can be the same sample. By way of example only, a selected amount of a known ion or molecule may be added to a test sample and can serve as a control analyte. In some aspects, the concentration or amount of an ion or molecule in a liquid sample may be known.

In some embodiments, an ion can be part of an ionic compound, can be monatomic, diatomic, or polyatomic, and can be a cation or an anion. By way of example only, $H^+$, $Na^+$, $OH^-$, $CH_3COO^-$, and $Ca^{2+}$, are different ionic species, or ion types, and represent different chemical classes. In some embodiments, a molecule species can be a monatomic, diatomic, or polyatomic molecule, a molecular compound, or a covalent compound. In some embodiments, an ion or molecule analyte 112 can be an ionizable atom, compound, or molecule. In some aspects, an ion or molecule analyte 112 can be for example, a weak acid such as acetic acid, propionic acid, or butyric acid. In some aspects, an ion or molecule analyte 112 can be a molecule that is an oligomer such as for example an oligonucleotide or oligopeptide. In some aspects, an ionizable analyte 112 may be ionized before or after addition of the analyte 112 to chamber 109 having submerged sensor 110.

In some embodiments porous conductive film 103 can comprise or be made of chemiresistive semiconducting $MO_x$ structures 104. In some aspects, porous conductive film 103 can comprise chemiresistive semiconducting $MO_x$ structures 104 that can have nanoscale dimensions, that is the $MO_x$ structures 104 can be nanostructures. In some embodiments, $MO_x$ structures 104 can have microscale dimensions and can be referred to as microstructures. In some embodiments, materials useful for $MO_x$ structures 104 include, but are not limited to, tin (II) oxide (SnO), tin (IV) oxide ($SnO_2$), combinations of SnO and $SnO_2$ (represented as $SnO_x$), ZnO, $TiO_2$, CuO, $WO_3$, indium oxide ($In_2O_3$), and indium-tin oxide (ITO).

In some embodiments, the term "structure" when referring to a chemiresistive semiconducting metal oxide ($MO_x$) structure 104, can refer to structures that may be called "particles" by a person having ordinary skill in the art. In some embodiments, $MO_x$ structures 104 can have any of a variety of shapes including spherical, cylindrical, cuboidal, or random geometrical shape and structures such as for example, "tubes", "wires", "rods", "fibers", and "traces". $MO_x$ structures 104 may be synthesized by one or more processes available to a person having skill in the art. $MO_x$ structures 104 having various dimensions and various ranges of dimensions are also available commercially. In some embodiments, $MO_x$ structures 104 for use in porous conductive film 103 can have at least one cross sectional dimension that is from about 1 nm to about 100 microns, including any selected size range therebetween. It is specifically contemplated that in some embodiments, $MO_x$ structures 104 can have at least one cross sectional dimension, that is of any size from about 1 nm to about 100 microns. In some aspects, $MO_x$ structures 104 can be chosen to be within selected ranges in the size range so as to optimize detection and quantification of selected ion or molecule analytes 112. In some aspects, a range of sizes for $MO_x$ structures 104 can be chosen to be more suitable for analyzing smaller or larger ion or molecule analytes 112 or for analyzing selected types or species of ion or molecule analytes 112. In some aspects, a selected range of sizes for $MO_x$ structures 104 can be chosen to be suitable for or to enhance exchange of submersion liquid 106 within the interstitial volume surrounding $MO_x$ structures 104, such as during washing of sensor 110. In some aspects, a selected range of sizes for $MO_x$ structures 104 can be chosen to be suitable for or to enhance diffusion of ion or molecule analytes 112 or other ions or molecules within the interstitial volume of liquid surrounding $MO_x$ structures 104. In some aspects, the rate of diffusion of ion or molecule analytes 112 or other ions or molecules within the interstitial volume of liquid surrounding $MO_x$ structures 104 may affect the sensor response profile 115 or the time at which a an electrical property of porous conductive film 103 is detected after exchange of submersion liquid 106.

In some embodiments, sensor 110 can comprise $MO_x$ structures 104 having a cross-sectional dimension less than about 500 nm, less than about 250 nm, less than about 100 nm, less than about 50 nm, less than about 10 nm, or less than about 5 nm, to as small as about 1 nm. In some embodiments, $MO_x$ structures 104 can have a cross-sectional dimension from about 10 nm to about 500 nm, from about 20 nm to about 250 nm, or from about 50 nm to about 100 nm. In some embodiments, $MO_x$ structures 104 can have a cross-sectional dimension from about 1 micron to about 100 microns or any selected size range therebetween, from about 10 microns to about 75 microns, or from about 20 microns to about 50 microns. In some embodiments, porous conductive film 103 can comprise $MO_x$ structures 104 of many sizes. Porous conductive film 103 may comprise a mixture of structures 104 having different sizes and/or shapes. For example a porous conductive film 103 may comprise $MO_x$ structures 104 wherein some of the $MO_x$ structures 104 can have cross sectional dimensions of from about 20 nm to about 100 nm, some can have cross sectional dimensions of from about 50 nm to about 250 nm, some can have cross sectional dimensions of from about 250 nm to about 500, some can have cross sectional dimensions of from about 500 nm to about 10 microns, some can have cross sectional dimensions of from about 10 microns to about 50 microns, some can have cross sectional dimensions of from about 50 microns to about 100 microns, and some may have cross sectional dimensions of any size range between about 1 nm and about 100 microns In some embodiments of the disclosure, preparation of porous conductive film 103 comprises depositing $MO_x$ structures 104 onto substrate 101 then sintering the deposited $MO_x$ structures 104 to achieve a desired level of connectivity among the $MO_x$ structures 104 so as to achieve a desired level of conductivity of porous conductive film 103. $MO_x$ structures 104 can be deposited by any of a variety of methods including for example spotting, sputtering, screen printing, and casting (e.g., drop casting, spin casting, roll casting, spray casting, and dip casting). In some aspects, porous conductive film 103 prepared by sputter deposition can demonstrate higher conductance than a porous conductive film 103 deposited by other different methods. In some aspects, porous conductive film 103 prepared by casting methods can demonstrate higher sensitivities to ion or molecule analyte 112 interaction than does porous conductive film 103 prepared by other different methods. In some embodiments, sintering of $MO_x$ structures 104 can be caused by heating, such as for example in an oven or by rapid thermal annealing. In some aspects, pulsed light methods (photonic sintering, photosintering) can be used for sintering deposited $MO_x$ structures 104. In some embodiments, the electrical contact resistance between porous conductive film 103 and electrode pair 102 can be kept low. This can be achieved using annealing and the addition of low contact resistance material that is in contact with both a portion of porous conductive film 103 and electrode pair 102.

In some embodiments, substrate 101 can comprise an insulating wafer such as quartz, glass, undoped or doped semiconductors (e.g., n-doped or p-doped silicon) with an insulating oxide barrier layer, a polymer, or a polymer film. In some embodiments, electrodes can be made from gold, platinum, nickel, and copper or alloys thereof.

Figure 2A:
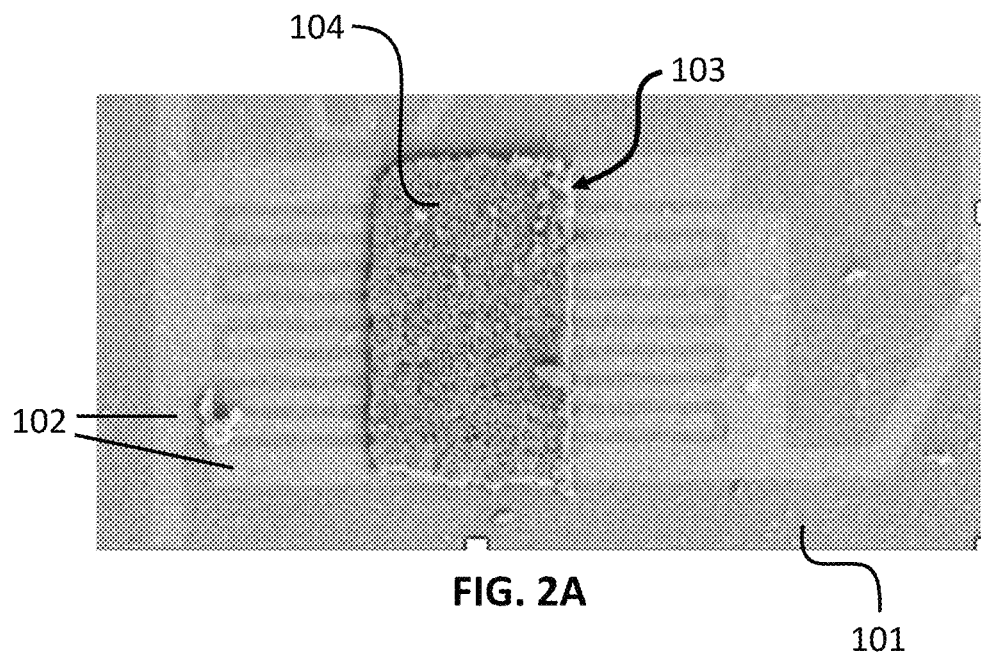
FIGS. 2A-2C are scanning electron micrographs (SEM) of an exemplary embodiment of a porous conductive film comprising $MO_x$ structures that are sintered tin oxide nanoparticles.
Figure 2B:
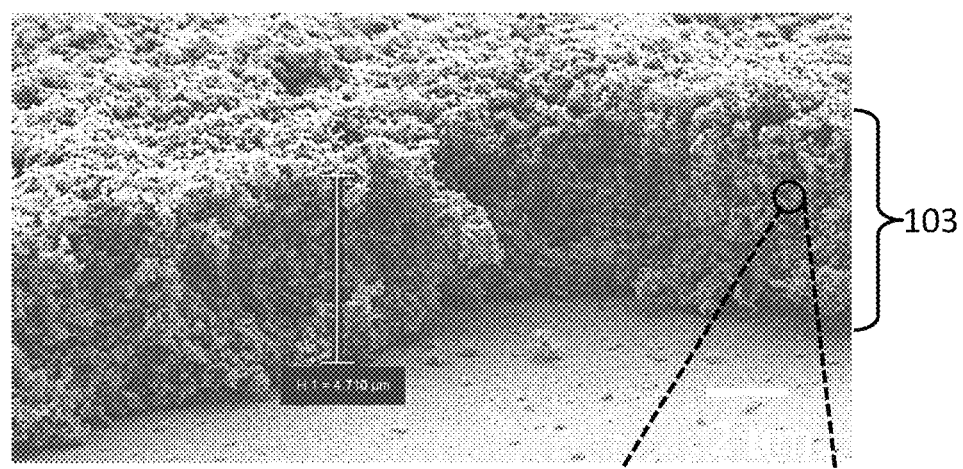
Figure 2C:
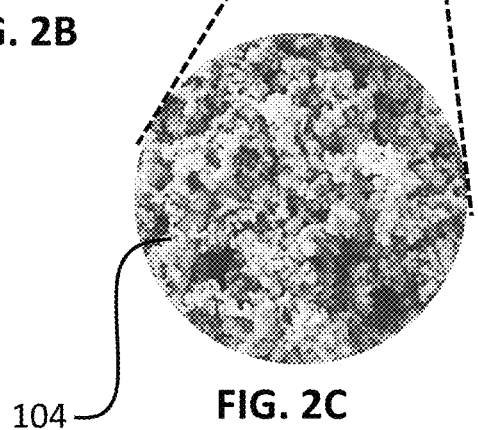

FIGS. 2A-2C are scanning electron micrographs (SEM) of an exemplary embodiment of porous conductive film 103 comprising $MO_x$ structures 104 that are sintered tin oxide nanoparticles. For this exemplary embodiment, ~50 nm $SnO_2$ particles (US Research Nanomaterials, Inc.; Houston, Tex., USA) were suspended in organic carrier fluid containing $SnCl_2$ and cast onto substrate 101. Cast particles were photosintered using a PulseForge® instrument (Novacentrix, Austin, Tex., USA) with multiple microsecond light pulses in the 500-900 V range and pulse duty cycle set between 5% and 70%.

FIG. 2A is an SEM showing a top down view of one exemplary embodiment of a porous conductive film 103 made from tin oxide nanoparticles that are $MO_x$ structures 104 deposited over a pair of interdigitated gold electrodes (electrode pair 102) positioned on substrate 101. FIG. 2B is an SEM showing an enlarged side view of a region of porous conductive film 103 comprising tin oxide $MO_x$ structures 104. FIG. 2C is an SEM showing an enlargement of a region of porous conductive film 103 comprising $MO_x$ structures 104 that are the tin oxide nanoparticles. After photonic sintering, carrier material (residual organic material) was decomposed (FIG. 2C), permitting electrical continuity between neighboring $MO_x$ structures 104. Electrical continuity may involve particle necking and fusion between neighboring grains. Conductance of cast porous conductive film 103 changed from an electrically insulative state (>20 MΩ nominal resistance) prior to sintering to a semiconductive state (50 kΩ-200 kΩ nominal resistance) following photosintering. In some aspects, nominal resistance of sintered porous conductive film 103 can be from about 5 k Ω to about 500 k Ω. In some aspects, nominal resistance of sintered porous conductive film 103 can be from about 1Ω to about $10^{15}$Ω. In some embodiments, selected photosintering or photonic sintering parameters for use in methods of the invention such as for example flash lamp pulse voltage, pulse repetition, and total pulse time can be adjusted to optimize necking between and among $MO_x$ structures 104. In some aspects, it may be preferred that $MO_x$ structures 104 not be sintered to form a bulk film. In some aspects, sintering to the state of a bulk film can result in higher conductivity but lower sensitivity.

In some embodiments, it can be useful to add binding agents to the carrier fluid used for casting particles. The use of binding agents can enhance mechanical stability of porous conductive film 103 and lower absolute film resistance. Binding agents can have compositions ranging from polymers to sol-gels. In the exemplary embodiment shown in FIG. 2A-2C, $SnCl_2$ was used as a binding agent. In some embodiments, varying the ratio of $SnCl_2/SnO_2$ in a casting fluid can enable adjusting the initial resistance of porous conductive film 103, thereby enabling the achievement of desired levels of resistance and sensitivity of sensor 110 for detection of a selected ions and molecules 112. It was also observed that in some embodiments, addition of $SnCl_2$ to the casting solution along with $SnO_2$ nanoparticles can provide deagglomeration of $SnO_2$ nanoparticles which resulted in homogenous cast films with little to no morphological variation across substrate 101. In some embodiments, gold or another noble metal surface catalyst, such as for example Pt, Ag, or Pd, can be deposited with $SnO_2$ to adjust conductance of porous conductive film 103 and sensitivity of detection of ions and molecules 112. Additional parameters and materials that can be adjusted, in some embodiments, to achieve desirable physical and functional properties of porous conductive film 103 include compaction of the film, stabilization agents, doping agent, and polymeric cofactors such as reducing agents and sequestering agents.

In some embodiments, any liquid in which sensor 110 is submerged can be referred to as a submersion liquid 106, and submersion liquid 106 can be changed for any suitable reason. The composition of submersion liquid 106 may be any suitable composition. For example only, in some embodiments submersion liquid 106 can be a liquid that is chosen because it is suitable for the intended use of apparatus 100 and sensor 110. For another example, in some embodiments, submersion liquid 106 can be a liquid that is chosen to provide for enhanced stability of sensor 110 over time. In some embodiments, submersion liquid 106 can comprise an aqueous liquid, an organic liquid, a liquid that is a mixture of an aqueous liquid and an organic liquid, a liquid ionic solution, an electrolytic solution, a molecular solution, deionized water, a buffer, or any combination of these. In some aspects, submersion liquid 106 can have a composition selected to enhance the binding affinity of certain ions or molecules in the liquid to $MO_x$ structures 104, which may be useful for establishing a baseline conductance of porous conductive film 103. Additional exemplary embodiments of submersion liquid 106 and liquid sample compositions are described throughout this disclosure. It is to be noted that the composition of submersion liquid 106 is not limited to the exemplary embodiments listed here. Submersion liquids 106 that are suitable for exemplary embodiments described herein and other embodiments will become apparent based on this disclosure.

In some embodiments, ions or molecules present in submersion liquid 106 can contribute to the conductance of electric current between electrodes in electrode pair 102 and can affect the responsivity of porous conductive film 103 to ion or molecule analytes 112. In some aspects, ions or molecules solvated in submersion liquid 106 may be physisorbed and/or chemisorbed to $MO_x$ structures 104 in porous conductive film 103. In some aspects, physisorption and/or chemisorption may occur in such a manner so as to create a monolayer isotherm whereby molecules and/or ions adsorb to $MO_x$ structures 104 in porous conductive film 103. In some aspects, adsorbed ions can attract or repel charge carriers in $MO_x$ structures 104 causing changes in the localized concentration of charge carriers and carrier mobility. In some aspects, surface molecular interactions between ions or molecules and $MO_x$ structures 104 may lead to charge accumulation or charge depletion in the space-charge layers of $MO_x$ structures 104 or across intergrain boundaries (i.e., the necked region between adjacent fused $MO_x$ structures 104), thereby affecting conductance or resistance of porous conductive film 103. As such, in some embodiments, the molecular and ionic composition of submersion liquid 106 can modulate the interaction of ion or molecule analytes 112 with porous conductive film 103 thereby modulating the effect that an ion or molecule analyte 112 can exert on electrical conductance during interaction of the ion or molecule analyte 112 with porous conductive film 103. In some embodiments, the number of surface binding sites on $MO_x$ structures 104 that are occupied by analyte 112 is proportional to the conductance or resistance of porous conductive film 103 and the number of surface sites occupied by analyte 112 is proportional to the concentration of analyte 112 in submersion liquid 106 at equilibrium. In some embodiments, by way of example, the composition of submersion liquid 106 in which a sensor 110 operates may be selected to enable increased detection sensitivity of sensor 110.

In some embodiments, one species of ion or molecule analyte 112 may have a higher binding affinity for $MO_x$ structures 104 than does another species of ion or molecule analyte 112. A first species of analyte 112 in submersion liquid 106 may compete with one or more different species of analytes 112 in submersion liquid 106 for binding with $MO_x$ structures 104 causing some or all of the one or more different species of analytes 112 that may already be bound to $MO_x$ structures 104 to be displaced into submersion liquid 106. Displacement of a selected species of analyte 112 by another species of analyte 112, from the surface of $MO_x$ structures 104, may result in a change in an electrical property of porous conductive film 103.

By way of additional example, in some embodiments, a submersion liquid 106 for sensor 110 operation can be selected for use with a sensor 110 having a selected type of $MO_x$ structure 104 (e.g., $MO_x$ structures 104 of a selected composition, architecture, and/or size, or a porous conductive film 103 having a selected thickness or porosity) so as to optimize an apparatus for use in detecting selected ion or molecule analytes 112. In many aspects, operation of apparatus 100 for detection, identification, and quantification of selected different species of ions and molecules 112 can be optimized by varying sensor 110 structure (e.g., $MO_x$ structure 104 composition, architecture, size, and shape, extent of sintering and porosity of a porous conductive film 103, and other structural parameters), submersion liquid 106 composition, sensor 110 operating parameters (e.g., applied voltage), chamber 109 volume, presence and/or type of diffusion matrices on $MO_x$ structures 104 (for modulating diffusion of ions and molecules), presence and/or type of ions or molecules bound to $MO_x$ structures 104, and presence and/or location of one or more semipermeable barriers 301 (for modulating diffusion of ions and molecules), to name several parameters.

By way of example, the number of binding sites (also referred to herein as surface interaction sites) on $MO_x$ structures 104 is proportional to the total surface area of $MO_x$ structures 104 in porous conductive film 103 as defined by the binding capacity. For example, the binding capacity of photosintered tin oxide structures 104 having cross-sectional dimensions of about 400 nm was measured by titrating a packed bed of tin oxide against a known concentration of acetic acid solution and found to be $2 \times 10^{-7}$ moles/gram of tin oxide. In some embodiments, the number of binding sites on $MO_x$ structures 104 in porous conductive film 103 can be adjusted by selecting an appropriate amount or mass of $MO_x$ structures 104 for use in the porous conductive film 103. In some aspects, for a given cross-sectional dimension of $MO_x$ structures 104, the binding or interaction capacity of $MO_x$ structures 104 can affect the concentration range over which an ion or molecule analyte 112 can be detected. For example, binding of an ion or molecule that is solvated in submersion liquid 106, to $MO_x$ structures 104 in porous conductive film 103, may result in a decrease in the concentration of the ion or molecule in submersion liquid 106. A porous conductive film 103 having a relatively higher binding capacity or a porous conductive film 103 having a greater mass of $MO_x$ structures can bind a larger number of ion or molecule analytes 112 than a porous conductive film 103 having a relatively lower binding capacity, or a porous conductive film 103 having less mass of $MO_x$ structures, thereby increasing the range of concentrations of ion or molecule analytes 112 that can be detected. In some aspects, the binding capacity of a given mass of $MO_x$ structures 104 in porous conductive film 103 may theoretically be sufficient to bind essentially all ion or molecule analytes 112 in submersion liquid 106, which could theoretically reduce the concentration of ion or molecule analytes 112 in submersion liquid 106 to essentially zero. In some aspects, the binding capacity of a given mass of $MO_x$ structures 104 in porous conductive film 103 may be such as to bind only a fraction of the total ion or molecule analytes 112 in submersion liquid 106. In these aspects, a different fraction of the total ion or molecule analytes 112 may remain solvated in submersion liquid 106 at equilibrium. In some instances, movement of ion or molecule analytes 112 from one region of porous conductive film 103 to a different region of porous conductive film 103 (e.g., by advection or convection of ions or molecules during flow of submersion liquid 106 or by diffusion of ion or molecule analytes 112 in submersion liquid 106) may lead to an increase in ion or molecule analytes 112 that are bound to porous conductive film 103 during re-equilibration. In some embodiments, adjusting the binding capacity and/or mass of $MO_x$ structures 104 in porous conductive film 103 can enable determination of the quantities and/or concentration of selected analytes 112 in a liquid sample. In some embodiments, sensor response profile 115 may be affected by the presence and/or concentration of ions or molecules in the submersion liquid 106. In some instances, a decrease in the concentration of an ion or molecule analyte 112 in submersion liquid 106 may cause a change in the electrical property of porous conductive film 103 that can be detected by selected sensors 110 in an array of sensors.

In some aspects, an ion or molecule analyte 112 interacting with a $MO_x$ structure 104 can be interacting with a molecule or ion that is present on the surface of a $MO_x$ structure 104, such as for example a solvated molecule from submersion liquid 106. In some aspects, an ion or molecule analyte 112 interacting with porous conductive film 103 can be interacting with charge carrier species in the space-charge layer of an $MO_x$ structure 104, such as for example an electron in the space-charge layer. In some aspects, an ion or molecule analyte 112 interacting with porous conductive film 103 may not be in physical contact with the surface of a $MO_x$ structure 104 but may be in close proximity to a structure so as to affect charge carrier movement in the space-charge layer.

In some embodiments, sensor 110 can be washed, by exposure to one or more liquid samples. In some embodiments, submersion liquid 106 can be changed before, during, or after use of the apparatus for detecting molecules or ions 112. By way of example only, apparatus 100 can be made to have sensor 110 submerged in a first submersion liquid, e.g. 106, that may be chosen for sensor 110 storage. In some aspects, for example during preparation of sensor 110 for ion or molecule analyte 112 sensing, the "storage" submersion liquid 106 may be replaced with a wash liquid 111, keeping the sensor submerged. Wash liquid 111 can be a submersion liquid 106 having a different composition from that of a "storage" submersion liquid 106.

In some embodiments, one or more washes can be performed prior to or after exposing sensor 110 to a liquid sample that is being analyzed for the presence and/or quantity of one or more selected ion or molecule analyte 112. In some aspects, sensor 110 may be washed with a liquid (e.g., 111) that is known to not comprise an ion or molecule analyte 112. In many aspects of the invention, aside from lacking a selected ion or molecule analyte 112 for detection, a wash liquid 111 can have the same composition as a test sample liquid. However, in some aspects, this is not a requirement. In some embodiments, sensor 110 can be washed with a wash liquid 111 having a different composition from that of a test sample. By way of example only, sensor 110 may be washed with a wash liquid 111 that is deionized water, prior to or after being exposed to a test sample that comprises a buffer solution. In some aspects, sensor 110 can be washed any suitable number of times and with any type of wash liquid 111 as may be suitable for a selected embodiment.

In some embodiments, washing of sensor 110 may be performed to purge ion or molecule analytes 112 from the surface of porous conductive film 103. In some aspects, purging can occur by diffusion of ions or molecules away from $MO_x$ structures 104 into wash solution 111 and in some embodiments can be assisted by repeated exchange of wash solutions 111 in chamber 109. In some aspects, purging may be accelerated by application of heat to sensor 110 or by using a heated wash solution 111. Purging may be caused by exposure of porous conductive film 103 to one or more selected species of ions or molecules, so as to displace molecules or ions already bound to $MO_x$ structures 104 in porous conductive film 103. The selected displacing species of molecules or ions may then be purged by washing of porous conductive film 103.

In some embodiments, apparatus 100 can comprise a plurality of sensors 110 submerged in a liquid 106 in chamber 109. In some aspects, the plurality of sensors 110 can be assembled as an array of sensors (also referred to herein as a "sensor array"). In some embodiments, a sensor array can comprise a single porous conductive film 103 having $MO_x$ structures 104 and being positioned on a substrate 101, porous conductive film 103 being operably connected to one or more electrode pairs 102 for generating electric current in one or more regions of the film and for detecting a change in an electrical property of the film in the selected regions. In some embodiments, a sensor array can comprise a plurality of porous conductive films 103, each film 103 having $MO_x$ structures 104 and being positioned on substrate 101 and each film 103 being operably connected to one or more electrode pairs 102 for generating electric current in porous conductive films 103 and for detecting a change in an electrical property of the porous conductive films 103.

In some embodiments, the number of sensors 110 in an array can range from one to hundreds, to thousands, to millions, depending on the application and device parameters. In some aspects, a sensor array can be a 3×3, 10×20, 40×60, 320×540, 640×480 VGA, 2056×1560 full size, 2592×3872 10 megapixel, or 3456×5184 18 megapixel array. A sensor array can be configured with an aspect ratio of, by way of example only 1×1, 1×2, 1×3, 1×4, 1×8, 1×32, 1×100, 1×500, 1×1000, 1×10,000, 2×3, 3×4, or 9×16, or an array can be configured with another aspect ratio. Sensors 110 can be grouped together in any of a variety of numbers and array sizes and shapes. For example, an array of sensors 110 can be circular or another shape and need not necessarily be in an ordered configuration, and sensors 110 may have electrode pairs 102 positioned in any of a variety of selected arrangements that may be useful for separating, detecting, identifying, and analyzing selected ion or molecule analytes 112. In some aspects, selected sensors 110 in an array can be employed as references and controls. In some embodiments, a sensor array can comprise one or more sensors 110 positioned on a CMOS read-out integrated circuit. In some aspects, a sensor array can comprise one or more sensors 110 positioned on a substrate 101 that is a printed circuit board and having lithographically-defined electrode pairs 102. A printed circuit board may be for example a glass-reinforced epoxy laminate material or a flexible circuit substrate comprising polyimide or other polymer. Such printed circuit boards are known in the art and are commercially available.

In some aspects, a sensor array can comprise one or more sensors 110 positioned on a test strip with printed and sintered electrode pairs 102.

In some embodiments, porous conductive film 103 can be cast as a continuous film over an array of electrode pairs 102 comprising a single pair or a plurality of electrode pairs 102. Porous conductive film 103 can be cast onto segregated individual pixels of a sensor array. In some embodiments, an array of electrode pairs 102 comprising a single pair or a plurality of electrode pairs 102 can be printed over porous conductive film 103. For example electrode pairs 102 may be printed on top of and in direct contact with porous conductive film 103. In some aspects of the disclosure, porous conductive film 103 can be patterned into segmented areas with corresponding electrode pairs 102 positioned to mitigate interference between segments.

In some embodiments, interaction of ion or molecule analytes 112 present in a liquid, with $MO_x$ structures 104 in porous conductive film 103 can be detected by determining a sensor response at one or more selected time points or continuously, during exposure of sensor 110 to a liquid sample. In some embodiments, response 115 of a sensor 110 to an ion or molecule analyte 112 may require interaction of the ion or molecule analyte 112 with a $MO_x$ structure 104. In many aspects, sensor response 115 can be determined and recorded as a measurement of an electrical property, such as for example a measurement of conductance or resistance of porous conductive film 103.

A sensor response 115 determined with a control sample may be referred to as a control sensor response or a control sensor response profile. Similarly, a sensor response 115 determined with a test sample may be referred to as a "test sample sensor response" or "test sample sensor response profile". As used herein, a "sensor response profile" or a "sensor response" can comprise sensor response data determined before, during, and/or after exposure of a sensor to a liquid sample. "Sensor response profile" (e.g., 115) may also mean a graphical representation or other representation of the determined sensor response data.

In some embodiments, for determining sensor response 115, a bias voltage is applied to one electrode of electrode pair 102 that is operably connected to porous conductive film 103, so as to cause current flow 114 between electrodes in electrode pair 102 across porous conductive film 103. For determining a response 115 of one or more sensors 110 in an array of sensors, bias voltage can be applied across porous conductive film 103 in the one or more sensors 110 in the array. In some aspects, sensor 110 can be equilibrated or substantially equilibrated in submersion liquid 106. Sensor equilibration refers to a condition in which no appreciable difference exists between adsorption and desorption of ions and molecules to and from $MO_x$ structures 104 of porous conductive film 103. An equilibrated or substantially equilibrated sensor 110 may show no appreciable change in an electrical property of porous conductive film 103 over time, i.e., sensor 110 may show no appreciable change in sensor response 115 over time. Sensor 110 equilibration can occur prior to or during voltage application. The period of time required for sensor 110 to reach equilibration may be about 1 nanosecond, about 10 nanoseconds, about 100 nanoseconds, about 1 microsecond, about 10 microseconds, about 100 microseconds, about 1 second, about 10 seconds, about 100 seconds, about 1 day, or about 1 year and any period of time between about 1 nanosecond and about 1 year. In some aspects, prior to exposure of sensor 110 to a test or control sample, a bias voltage can be applied for a duration of time that is sufficient to allow sensor 110 to equilibrate or stabilize to the environmental conditions (i.e., an equilibrated sensor 110 exhibits a substantially unchanging current or resistance value over a chosen time period). In many embodiments, sensor 110 can be equilibrated in submersion liquid 106 that is selected to be suitable for analysis of a test or control sample. By way of example only, sensor 110 may be equilibrated in submersion liquid 106 that is a liquid in which sensor is stored 110, in water or another aqueous solution, in a buffer solution, or in any aqueous liquid compatible with sensor operation.

Determination of sensor response data 115 can be initiated at any time after bias voltage is applied, either prior to or after sensor 110 equilibration. Prior to liquid sample exposure, an equilibrated sensor 110 may exhibit a relatively unchanging current or resistance value that, in some aspects, corresponds to a baseline sensor response 115. In some aspects, after a selected period of time of determining baseline sensor response data 115, sensor 110 may be exposed to a liquid sample, such as a test sample, a control sample, a wash sample 111, or other liquid sample. In some aspects, exposure of sensor 110 to a liquid sample is accomplished by moving some or all of submersion liquid 106 out of chamber 109 and replacing it with a submersion liquid 110 having a different composition or with a submersion liquid 106 having the same composition. In many embodiments, exposure of sensor 110 to a control liquid sample or a test liquid sample can be accomplished by addition of the liquid sample to submersion liquid 106 present in chamber 109, through inlet port 107. In some aspects, desorption of ions or molecules from a porous conductive film 103 can occur after stopping the addition of a liquid sample to chamber 109 or during washing of sensor 110 and determining a sensor response 115 during the desorption phase can be useful for detecting, identifying, and quantifying ion or molecule analytes 112 in a sample. In some aspects, determining a sensor response 115 during the displacement of a species of ion or molecule analyte 112 from porous conductive film 103, by a different species of ion or molecule analyte 112 can be useful for detecting, identifying, and quantifying ion or molecule analytes 112 in a sample.

In some embodiments, sensor exposure times to a liquid sample may range from a few milliseconds to hundreds or even thousands of seconds. By way of example only, exposure of a sensor to a liquid sample may for be about 0.001 sec, 0.01 sec, 0.1 sec, 0.2 sec, 0.5 sec, 1 sec, 2 sec, 5 sec, 10 sec, 20 sec, 30 sec, 60 sec, 120 sec, 300 sec, 400 sec, 500 sec, 1,000 sec or any specific selected duration between about 0.001 sec and about 1,000 sec or more inclusive. In some embodiments, there may be no limit on the selected time period for sensor response determination. Any exposure duration time may be used in combination with any number of replicates performed with the same or different liquid samples.

Sensor response data can be determined for a duration of time that can be from a selected start time to a chosen time point after application of a bias voltage. In some embodiments, data determination periods can be in the range of from about 1 nanosecond, 1 microsecond, 0.00001 s, 0.0001 s, 0.001 sec, 0.01 sec, 0.1 sec, 0.2 sec, 0.5 sec, 1 sec, 2 sec, 5 sec, 10 sec, 20 sec, 30 sec, 60 sec, 120 sec, 300 sec, 400 sec, 500 sec, 1,000 sec or more, and specifically includes any range of time between about 1 nanosecond and about 1,000 sec. In some embodiments sensor response data can be determined for hours or days. It is specifically contemplated that in some aspects there is no limit on the time period for data determination. In some embodiments, determining sensor response data (i.e., determining a sensor response profile) can comprise recording or storing the data.

In some aspects, sensor response measurements can also be made during exchange of liquid samples, such as for example when molecules and ions in a liquid are in a non-equilibrium state. In some aspects, desorption of ions or molecules from porous conductive film 103 may occur during exchange of submersion liquid 106 or during washing of sensor 110, and determining a sensor response 115 during the non-equilibrium desorption phase can be useful for detecting, identifying, and quantifying ion or molecule analytes 112 in a sample. For example, sensor response data can be measured while a sensor is incubating in a first liquid (e.g., submersion liquid 106), during exchange of the first liquid with a second liquid such as for example a test sample that may comprise an analyte of interest, during washing of sensor 110 with any of a variety of liquid samples, and/or during any combination of liquid exchanges. In some embodiments, sensor response data can be determined during manipulation of liquid in chamber 109. For example, in some aspects, sensor response data can be determined during addition of a control or test sample liquid to chamber 109 in which sensor 110 is submerged.

In some embodiments, one or more determinations of sensor response profiles with the same liquid sample may be made. For example, an array of sensors may be simultaneously exposed to a liquid sample and response data for each sensor collected. In some embodiments, aliquots of a single liquid sample may be diluted to have different concentrations of sample components, and a sensor response may be determined with one or more of these diluted aliquots. In some aspects, dilution of a sample can provide a means to increase the dynamic range of quantitation of one or more analytes 112 in a test sample. In some aspects, multiple sensor response profiles may be determined in succession, such as for example when sensor responses to multiple liquid sample exposures are determined. In some aspects, multiple sensor response profiles may be measured in parallel from a sensor array comprising a plurality of sensors 110 in the same housing 105.

In some embodiments, a control sensor response profile can be determined using the same sensor as that used for determining a test sample sensor response profile, either prior to or following the determination of the sensor response profile with the test sample. In some embodiments, multiple sensor response profiles can be determined with a single test sample or a portion of the same test sample.

In some aspects, sensor response data can be determined simultaneously for a plurality of sensors that are present in a sensor array, using ROICs, such as for example, ROICs comprising silicon CMOS logic. Cross comparison of sensor response profile data from multiple sensors in a sensor array can be useful for identifying or quantifying molecules and/or ions.

In some aspects a sensor response may be sensitive to temperature. Sensor response can be determined at a temperature that is approximately 25° C. or at another temperature (or temperatures) that can be lower or higher than 25° C. and that are suitable for experimental conditions. In some aspects, an apparatus 100 may further comprise a heater or a means for heating porous conductive film 103, such as for example a heating strip or thermoelectric device. In some aspects, a heater can be a resistive heater comprising planar platinum wires that can be deposited under porous conductive film 103. A heater can be resistive heating tape applied to the backside of substrate 101. In some aspects, heating of porous conductive film 103 can be achieved by illumination of the film with an optical or infrared light source. In some aspects a heating means can comprise a liquid, in which porous conductive film 103 is submerged, that is heated to a suitable temperature. In some aspects, an apparatus 100 may further comprise a cooler or a means for cooling porous conductive film 103. A cooler can be one or more thermoelectric coolers applied to the backside of substrate 101 or housing 105, or submersion liquid 106 may be cooled to a suitable temperature.

In some embodiments, a sensor response to an ion or molecule analyte 112 can be affected by the diffusion rate of ions or molecules in a liquid sample through submersion liquid 106 and throughout porous conductive film 103 and the interstitial liquid among the $MO_x$ structures 104. In some aspects, differences in the diffusion rates of ion and molecule analytes 112 can result in temporal separation of analytes interacting with the surface of porous conductive film 103, which may result in a sensor response profile that can improve the detection, identification, and quantification of analytes in a liquid sample. In some aspects, diffusion of different species of ion or molecule analytes 112 in submersion liquid 106 may result in physical separation of analytes over time such that different species of ion or molecule analyte 112 may interact with binding sites on $MO_x$ structures 104 in different regions of porous conductive film 103. In some aspects, the detection and quantification of a plurality of selected analytes can be made more accurately by using an apparatus that is designed to enhance separation of ion or molecule analytes 112 by enhancing differential diffusion of ion or molecule analytes 112.

Figure 3A:
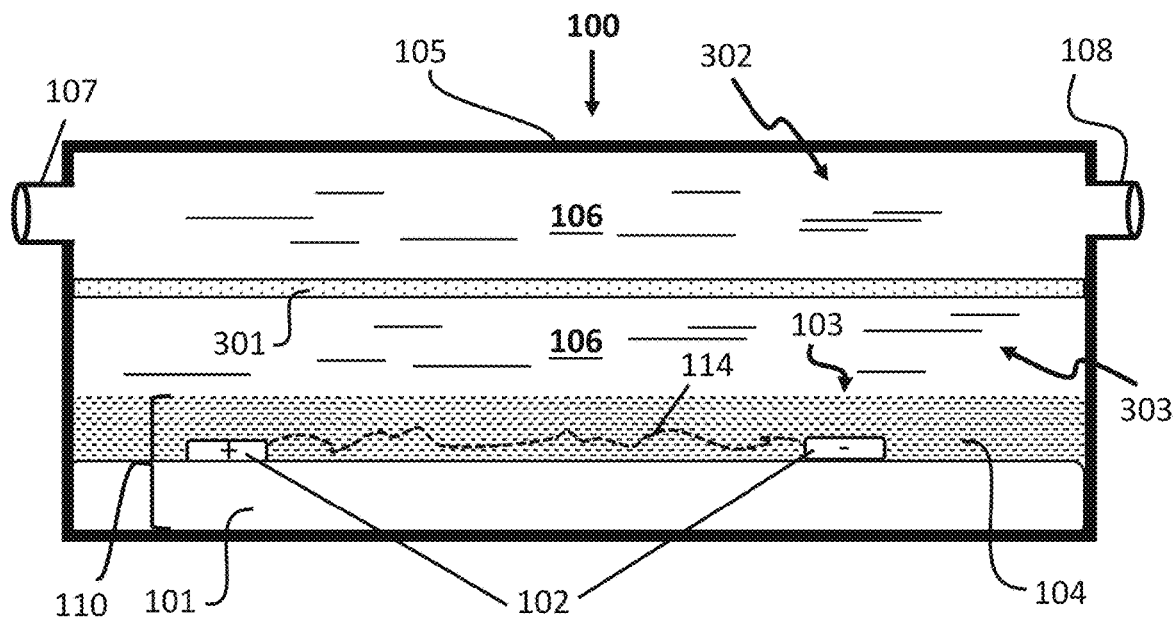
FIGS. 3A-3B illustrate a schematic depiction of an exemplary embodiment of an apparatus modified to enhance differential diffusion of two selected analytes present in liquid sample.
Figure 3B:
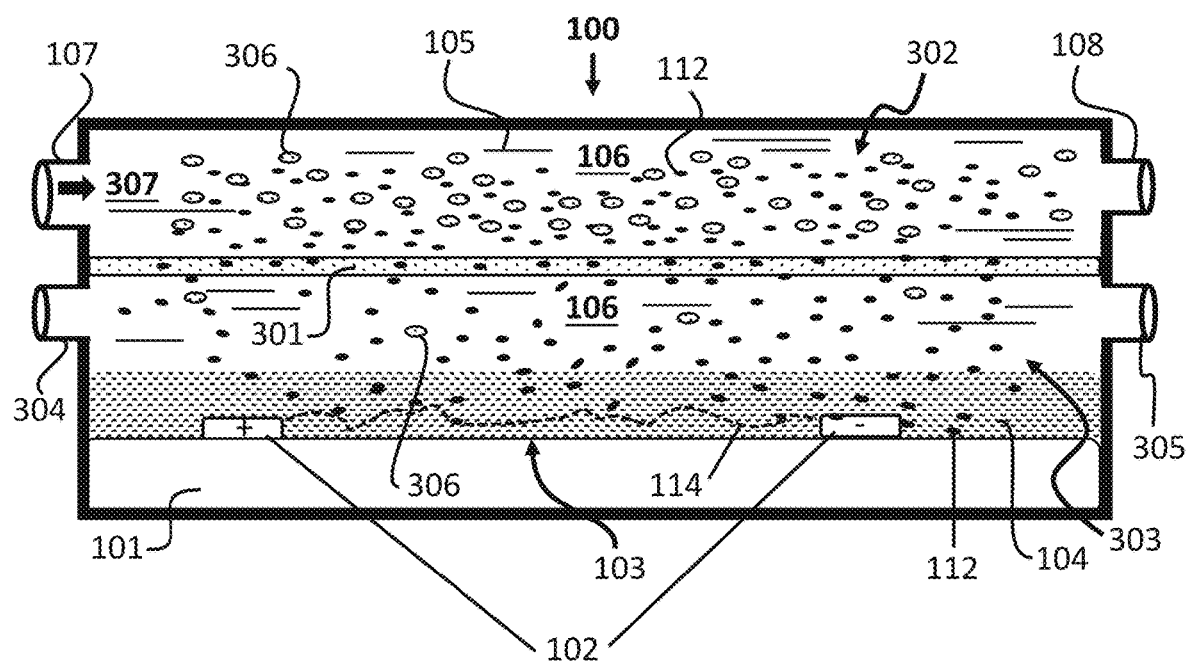

FIGS. 3A-3B illustrate a schematic depiction of an exemplary embodiment of an apparatus designed to enhance differential diffusion of two selected species of analytes 112 and 306 present in liquid sample 307. FIG. 3A illustrates apparatus 100 that comprises a semipermeable barrier 301 positioned within housing 105, thereby defining first subchamber 303 and second subchamber 302, wherein sensor 110 is positioned in first subchamber 303 and submerged in liquid 106. In some embodiments, semipermeable barrier 301 can modify or prevent the diffusion of selected species of ion or molecule analytes 112 to $MO_x$ structures 104 in porous conductive film 103.

In some embodiments, liquid 106 in subchambers 302 and 303 can be the same liquid, as illustrated here. Liquid 106 in subchamber 303 is also a submersion liquid 106. In some embodiments the liquids in subchambers 302 and 303 can have different compositions. As shown in FIG. 3B, liquid sample 307 having analytes 112 and 306 is introduced into subchamber 302 for analysis. Here, liquid sample 307 is added directly to liquid 106 present in subchamber 302. Semipermeable barrier 301 is depicted as modifying the diffusion rate of selected analytes 112 and 306. In this example, analyte 112 can readily cross semipermeable barrier 301, whereas analyte 306 crosses semipermeable barrier 301 at a much slower rate. In some embodiments, semipermeable barrier 301 can completely block passage of a selected species of analyte while allowing a different selected species of analyte to cross the barrier. In some aspects semipermeable barrier 301 can be positioned so as to be in contact with porous conductive film 103. In some aspects, semipermeable barrier 301 can be positioned at any selected distance from porous conductive film 103.

In some embodiments such as that illustrated in FIG. 3B, housing 105 can comprise a second inlet port 304 that can provide for fluid communication with first subchamber 303 and optionally a second outlet port 305 that can provide for fluid communication with first subchamber 303, and the ports may permit liquid exchange and flow into and out of subchamber 303. In some aspects, ports 304 and 305 can be used for exchanging submersion liquid 106. In some embodiments, exchange of liquid in one or both of the subchambers can assist in removal of a liquid sample and in washing semipermeable barrier 301, for example to purge analytes 112 that may be bound to semipermeable barrier 301 and/or porous conductive film 103 or that may be present in interstitial liquid present in porous conductive film 103 or in semipermeable barrier 301.

In some embodiments, diffusability of selected ion or molecule analytes across semipermeable barrier 301 can be dependent on the size (e.g., molecular weight) and/or structure of the selected analytes 112. For example, semipermeable barrier 301 may prevent the passage of selected molecules (e.g., 306) that are too large or otherwise structurally incompatible with crossing semipermeable barrier 301. In some aspects, diffusability of ion or molecule analytes 112 across semipermeable barrier 301 can be dependent on other factors such as by way of example only, the interaction of an ion or molecule analyte 112 with another molecule or ion in semipermeable barrier 301 or another molecule or ion attached to semipermeable barrier 301 or the affinity of an ion or molecule analyte 112 for semipermeable barrier 301. Introduction of submersion liquid 106 to chamber 105 may occur in the region of a sensor, such as for example a region that is above porous conductive film 103 or may occur in a region that is adjacent to but not over a porous conductive film 103.

In some aspects, semipermeable barrier 301 may be a membrane having pores that allow for diffusion of selected ion or molecule analytes 112 across semipermeable barrier 301. In some aspects, semipermeable barrier 301 can be a membrane made of, for example, regenerated cellulose or cellulose ester, polysulfone, polyethersulfone (PES), etched polycarbonate, or collagen to name only a few materials. Pores in semipermeable membrane barrier 301 can have any selected size or range that is suitable for a specific embodiment. By way of example only, pores in semipermeable barrier 301 may be of a size that allows diffusion across the barrier of ion or molecule analytes having a molecular weight or physical dimensions that can reduce the rate of or prevent diffusion across the barrier of the ion or molecule analytes 112. In some aspects, exemplary pores may have any selected size or range that is suitable for a specific embodiment of the invention. In some aspects, semipermeable barrier 301 may comprise a plurality of semipermeable barriers, such as for example a plurality of semipermeable membranes, which may be made of the same material or made of different materials and which may have pores of any selected size or size range. In some aspects, a plurality of semipermeable barriers 301 may be positioned such that diffusion of ion or molecule analytes may occur in series during movement of submersion liquid 106 across a sensor.

Some apparatus embodiments, such as those depicted in FIGS. 3A-3B, can be used for analyzing ion or molecule analytes 112 that are products or by-products that may be produced during the progress of a chemical reaction or for analyzing other molecules or ions present in a chemical reaction. For example, progress of a chemical reaction taking place in subchamber 302 may be monitored by detection of reaction products or by-products that are ion or molecule analytes 112, which can diffuse across semipermeable barrier 301 for detection by sensor 110.

In some embodiments, the thickness and/or composition of semipermeable barrier 301 can affect the amount of an analyte 112 reaching porous conductive film 103, and the diffusion rate of an analyte 112 to porous conductive film 103, thereby impacting a sensor response, such as by altering the onset of detection of a change in an electrical property of porous conductive film 103, by altering the rate of change of an electrical property of porous conductive film 103, or by altering the magnitude of the change of an electrical property of porous conductive film 103.

Figure 4:
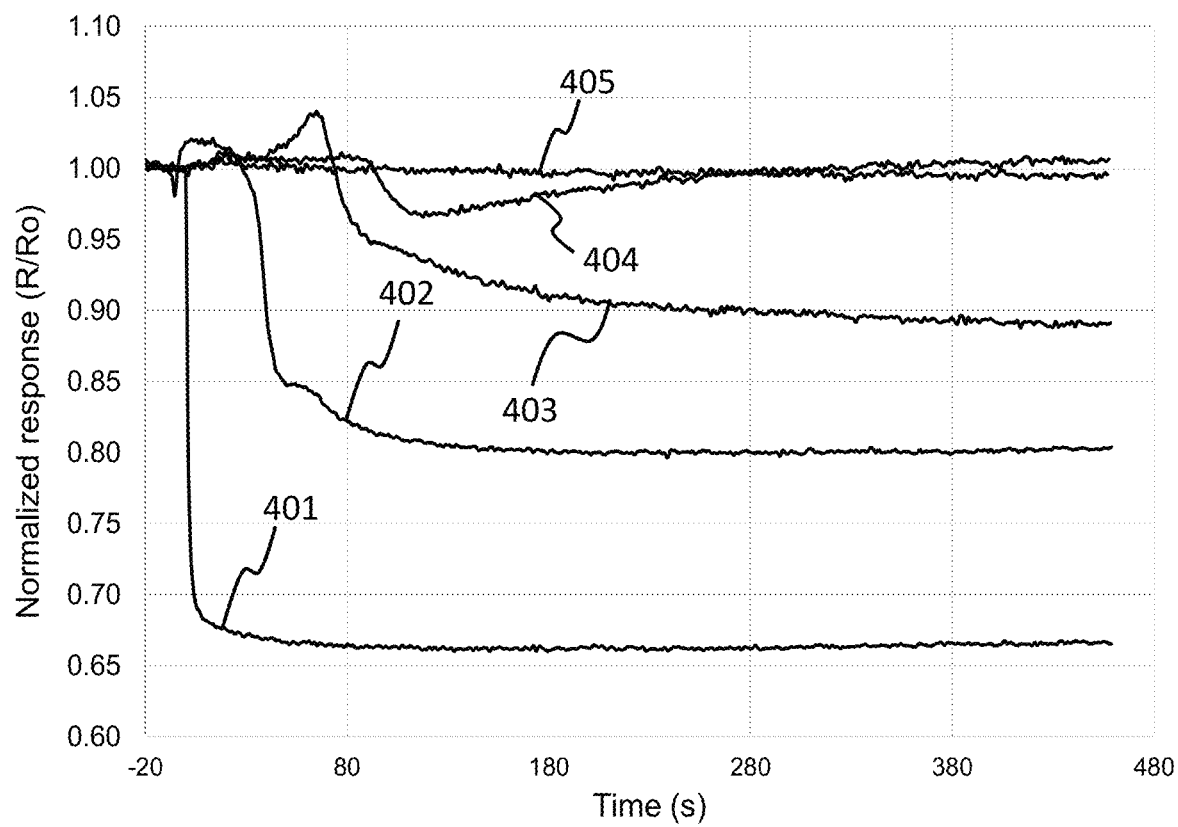
FIG. 4 shows sensor response profiles determined with liquid samples of 100 mM NaCl in the presence of different embodiments of a semipermeable barrier, in the absence of a semipermeable barrier, and in the presence of an impermeable barrier.

FIG. 4 shows sensor response profiles determined with liquid samples of 100 mM NaCl in the presence of different embodiments of a semipermeable barrier 301, in the absence of a semipermeable barrier 301, and in the presence of an impermeable barrier. In this example, each 100 mM NaCl liquid sample was introduced into submersion liquid 106 through inlet port 107 of apparatus 100 and conductivity of porous conductive film 103 was measured over time. Sensor response data were normalized and plotted as $R/R_o$ (measured resistance divided by initial resistance). Sensor response 401 was determined with a NaCl sample in the absence of a semipermeable membrane barrier 301. Sensor response 402 was determined with a NaCl sample in the presence of a single layer of a semipermeable barrier 301 that was a membrane. In this example, semipermeable barrier 301 was a dialysis membrane made of regenerated cellulose (Spectrum Laboratories; Rancho Dominguez, Calif.) having a MW cutoff of approximately 3,500 Daltons, approximate pore sizes of 1-3 nm, and an approximate wet thickness of 51 microns. The presence of a single layer of semipermeable membrane barrier 301 positioned between subchambers 302 and 303 delayed the appearance of a detectable change in the conductivity of the porous conductive film 103. Sensor response 403 was determined with a NaCl sample in the presence of two layers of the semipermeable membrane barrier 301, and sensor response 404 was determined with an NaCl sample in the presence of four layers of the semipermeable membrane barrier 301. Sensor response profile 405 was determined using an impermeable plastic membrane positioned between subchamber 302 and subchamber 303 in place of a semipermeable barrier 301. A progressively increasing temporal delay in the appearance of a detectable change in the conductivity of the porous conductive film 103 correlated with increasing thickness of semipermeable barrier 301. Similarly, a progressively decreasing magnitude of change in the equilibrium conductance of porous conductive film 103 may correlate with fewer ion or molecule analytes 112 binding to porous conductive film 103. Using various types and thicknesses of a semipermeable barrier 301 during analysis of liquid samples may alter the diffusion rates of different species of ion or molecule analytes 112 in a different manner, and in some embodiments can enhance discrimination among different ion or molecule species analytes 112 during detection and quantification of analytes. In some aspects, a semipermeable barrier may prevent passage of one or more species of ion or molecule analytes to porous conductive film 103, by binding to some or all of the molecules or ions in a liquid sample.

In some embodiments, a diffusion matrix comprising molecules that may interact with ion or molecule analytes 112 may be applied to semipermeable barrier 301 by covalent chemical coupling, chemisorption, or physisorption. A diffusion matrix may prevent passage of or alter the rate of diffusion of one or more species of ion or molecule analytes 112 to porous conductive film 103, by non-specifically interacting with some or all of the ion or molecule analytes 112 in a liquid samples. In some embodiments, molecules that interact specifically with some or all of ion or molecule analytes 112 in a liquid sample may be affixed to semipermeable barrier 301 and may affect diffusion of ion or molecule analytes 112 to porous conductive film 103.

In some embodiments, a liquid sample can be a biological sample or an extract of a biological sample and can be from or may comprise blood, serum, plasma, tissue, organs, semen, vaginal fluid, saliva, breath, tears, sputum, feces, urine, sweat, a bodily fluid, hair follicles, skin, or any sample containing or constituting biological cells. In some embodiments a liquid biological sample can be from an organism, such as for example a patient. In some embodiments, a sample can be from a patient that has tested positive for a disease, a patient undergoing treatment, a patient with a tumor or known mutation that results in the production of a specific disease-associated analyte, or a patient suspected of having a disease or condition. A biological sample can comprise one or more ion or molecule species that may be indicative of the presence of a pathogen, a virus, a prion, a fungus, a bacterium, or another organism. In some aspects a liquid sample can be a biological sample or an extract of a biological sample from an animal or plant. In some aspects, a liquid sample may be collected from an animal or plant extract for evaluating the health of the animal or plant or for evaluating the suitability of the animal or plant as a food source. In some embodiments, a liquid sample may not be a biological sample.

In some embodiments, a biological sample may be exposed to sensor 110 in situ, that is an apparatus 100 comprising sensor 110 or an array of sensors 110 may be positioned for example at a location at which an ion or molecule analyte 112 may be present. For example, apparatus 100 may be affixed to a tooth and may be used for detecting an ion or molecule analyte 112 in a liquid sample that is saliva, blood, or other bodily fluid that may come in contact with sensor 110. In another exemplary embodiment, apparatus 100 may be introduced or placed into a living subject, such as for example in a tissue, an organ, or a body cavity for analysis of biological liquids in the subject. In some embodiments, apparatus 100 may be positioned in a capsule that can be swallowed or otherwise placed into the digestive tract of a patient or other human subject and may be used in situ for detecting and analyzing an ion or molecule analyte 112 such as for example an analyte 112 in a liquid sample that may be present in a tissue, an organ, or a body cavity (e.g., stomach fluid, intestinal fluid, and lymph to name a few examples).

In some aspects, a liquid sample can be a chemical mixture such as for example a chemical reaction or a portion thereof, an environmental sample such as for example an aqueous environmental sample, an extract of an environmental sample such as for example a soil extract or an extract of an aqueous sample. In some aspects, an environmental sample can comprise a toxicant or a biological toxin. In some aspects, a liquid sample can comprise a synthetically prepared biological or chemical entity, which can be for example a precursor or product of a biological, chemical, pharmaceutical, or industrial manufacturing process or reaction.

In some embodiments, the presence of and/or the amount of one or more selected ion or molecule analytes 112 in a sample may be indicative of a disease or condition, may correlate with the severity of a disease or condition, may be used to evaluate the response of a patient to a treatment, or may be used to optimize treatment of a patient. The presence or amount of an ion or molecule analyte 112 in a biological sample can be examined to evaluate or correlate the analyte with pharmacokinetics or to adjust the treatment of a patient such as with a compound or a drug. In some aspects, an ion or molecule analyte 112 can be a metabolic by-product or breakdown product of a treatment compound or a drug.

In some embodiments, the presence or amount of an ion or molecule analyte 112 in a biological sample can be examined to evaluate or correlate the presence or amount of the analyte with diet or to recommend adjustments to the dietary intake of a person or patient. Exemplary analytes 112 that may be detected and quantified in these embodiments include proteins, carbohydrates, salts, metabolic products including breakdown products of foodstuffs. Exemplary liquid samples for use in these embodiments include saliva and digestive tract liquids or solid extracts, for example from the stomach, small intestine, large intestine, and/or rectum.

In some embodiments, a liquid sample may be from a commercially available product comprising a liquid designed for human consumption such as a liquid beverage (e.g., water, milk, juice, soda, alcoholic beverages) or from other liquids such as raw meat juices, vegetable juices, or liquids used for cooking (e.g., oils, purees, extracts). In some aspects, a liquid sample may be from a commercial product not designed for human consumption such as liquids used for cleaning, bleaches, soaps, perfumes, colognes, oils (e.g., suntan and massage oils), and liquids used for lubrication or moisturizing.

In some aspects, a liquid sample can be prepared using methods for isolating or purifying an analyte of interest. In some aspects, methods for extracting, isolating, or purifying molecules or ions from numerous types of samples, including biological, environmental, chemical reaction, petroleum refining, and industrial or pharmaceutical manufacturing samples, are available in the art or can be developed by one of skill in the art. In some aspects, a liquid sample is not purified or extracted.

Figure 5:
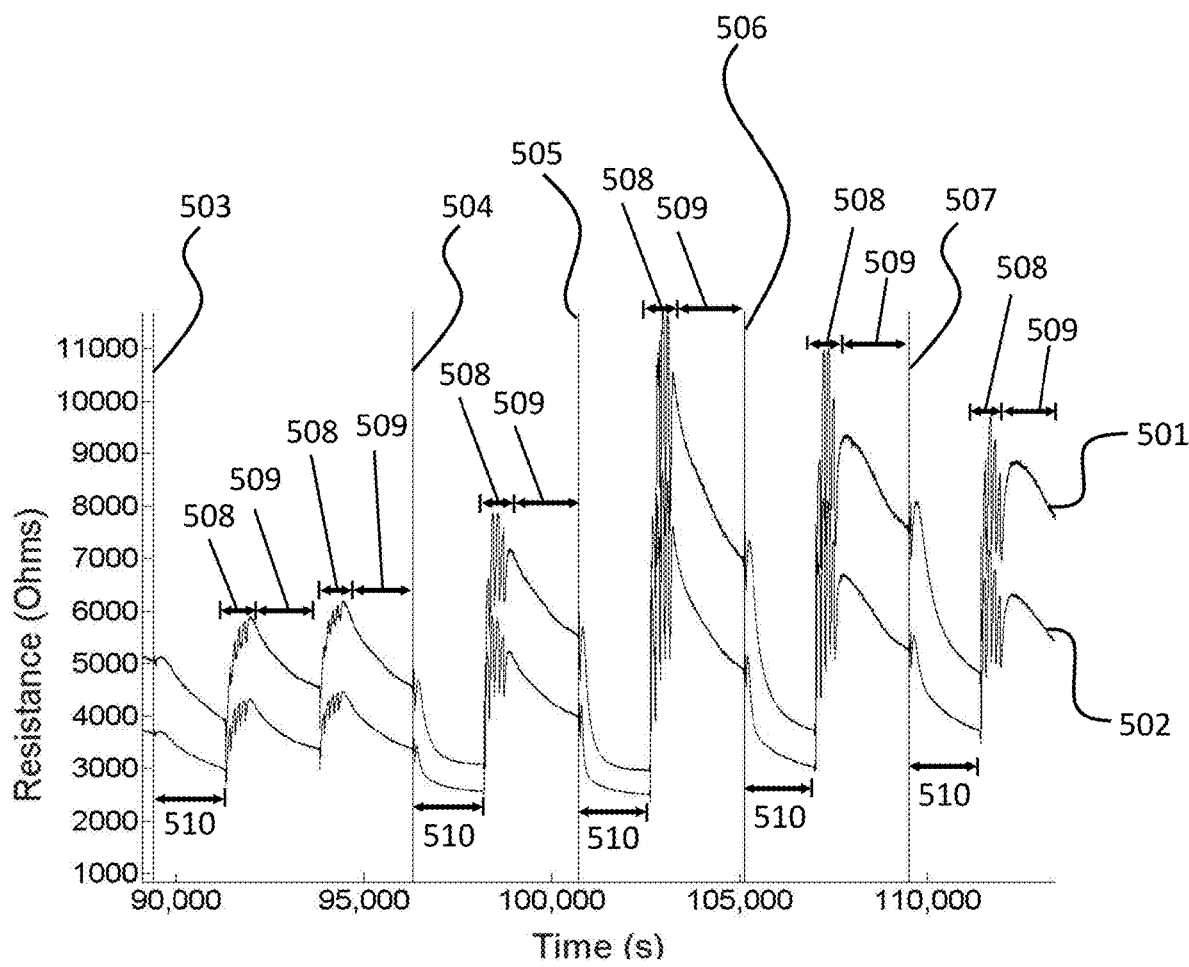
FIG. 5 illustrates sensor response profiles determined during analysis of liquid samples having different ions or molecules and during analysis of samples having the same ion or molecule species but at different concentrations.

FIG. 5 illustrates sensor response profiles determined during analysis of liquid samples having different ions or molecules and during analysis of samples having the same ion or molecule species but at different concentrations. In this exemplary embodiment, apparatus 100 comprised semi-permeable barrier 301, and test samples were added to subchamber 302. Sensor response profiles 501 and 502 were determined using two different sensors 110 in an apparatus 100. Each sensor was exposed, at different times, to the same succession of test sample liquids each test sample liquid having a different species of analyte 112 or a different concentration of an analyte 112. Electrical response of porous conductive film 103 in each sensor 110 was determined throughout the entire series of test sample liquid additions and incubations. Vertical lines (503-507) represent the time of addition, to chamber 109, of a liquid test sample having 10 mM glucose 503, 10 mM KCl 504, 50 mM NaCl 505, 25 mM NaCl 506, and 10 mM NaCl 507. After each test sample addition, the electrical response was measured for a selected period of time 510 in the presence of the test sample. Following test sample exposure, a series of washes were performed during wash period 508 by introducing and exchanging wash liquids in each subchamber 302 and 303. Subchambers were filled with the last wash in the series and allowed to rest for a dwell period 509 prior to addition of the following test sample. In this example, for the analysis of glucose (503), two consecutive wash series were performed during wash period 508, with each series of washes being followed by dwell period 509. The data illustrate that the interaction of different species of analytes 112 with porous conductive film 103 altered film conductivity in a different manner, as represented here by different shapes of the graphically depicted sensor response profiles. The data also illustrate that, in test samples having the same ionic species but at different concentrations, interaction of analytes 112 with porous conductive film 103 altered film conductivity in a different manner. As evidenced in sensor response profiles 501 and 502, the electrical response of porous conductive film 103 changed at a much faster rate during selected period of time 510 after sensor 110 was exposed to a test sample comprising 50 mM NaCl, 505, compared to the electrical response change of porous conductive film 103 when sensor 110 was exposed to a test sample comprising 25 mM NaCl, 506. Similarly, the electrical response of porous conductive film 103 changed at a much faster rate during selected period of time 510 after sensor 110 was exposed to a test sample comprising 25 mM NaCl, 506, compared to the electrical response change of porous conductive film 103 when sensor 110 was exposed to a test sample comprising 10 mM NaCl, 507. The faster change in resistance that was observed after exposure to 25 mM NaCl is believed to be due to a higher concentration gradient of molecules and ions in submersion liquid 106 (for the 25 mM sample) that increased the rate of diffusion of analytes 112 to porous conductive film 103 and the rate of adsorption to and desorption from $MO_x$ structures 104, of analytes 112, as can be predicted by a product of Fickian diffusion, Langmuir isotherm formation, and charge carrier exchange rates with $MO_x$ structures 104.

Throughout the specification, most graphical depictions of sensor response measurements show response data that have been converted to resistance and that are plotted as $R/R_o$ (measured resistance divided by initial resistance). In many aspects, a higher ratio $R/R_o$ correlates to lower conductivity of porous conductive film 103, and a lower ratio $R/R_o$ correlates with higher conductivity of porous conductive film 103. Increases and decreases in the $R/R_o$ ratio correlate with increased charge carrier (e.g., electron) accumulation or depletion in the space-charge layers of the $MO_x$ structures, which is specific to the species of molecule or ion that is interacting with an $MO_x$ structure and the ability of the molecules or ions in solution to partially stabilize excess or donated charge on the adsorbed molecules or ions. By way of example, exposure to a chloride solution caused a decrease in resistance of porous conductive film 103, which correlates with a donation of electron carriers (charge carriers) from adsorbed chloride ($Cl^-$) ions to the space charge layer of $MO_x$ structures 104. It is believed that donation of electron carriers to the $MO_x$ structures is possible because the dipoles of the submersion liquid 106 can stabilize the chloride species after donation, as was observed after exposure period 510. During wash period 508, chloride ions may desorb from $MO_x$ structures 104 due to entropic equilibration as the $R/R_o$ ratio returned to its original baseline after dwell period 509.

Figure 6A:
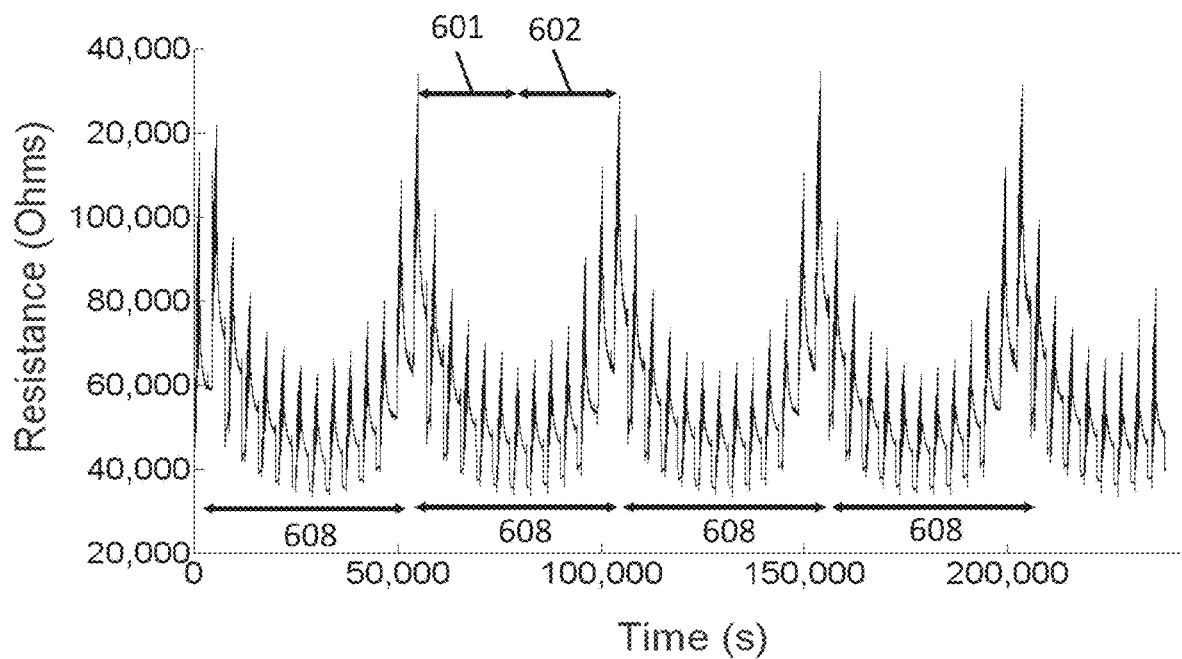
FIGS. 6A-6C illustrate sensor response profiles determined during analysis of liquid samples having the same analyte species but at different concentrations, sensor responses to samples having different pH values, and a plot of peak sensor responses to liquid samples having different pH values.
Figure 6B:
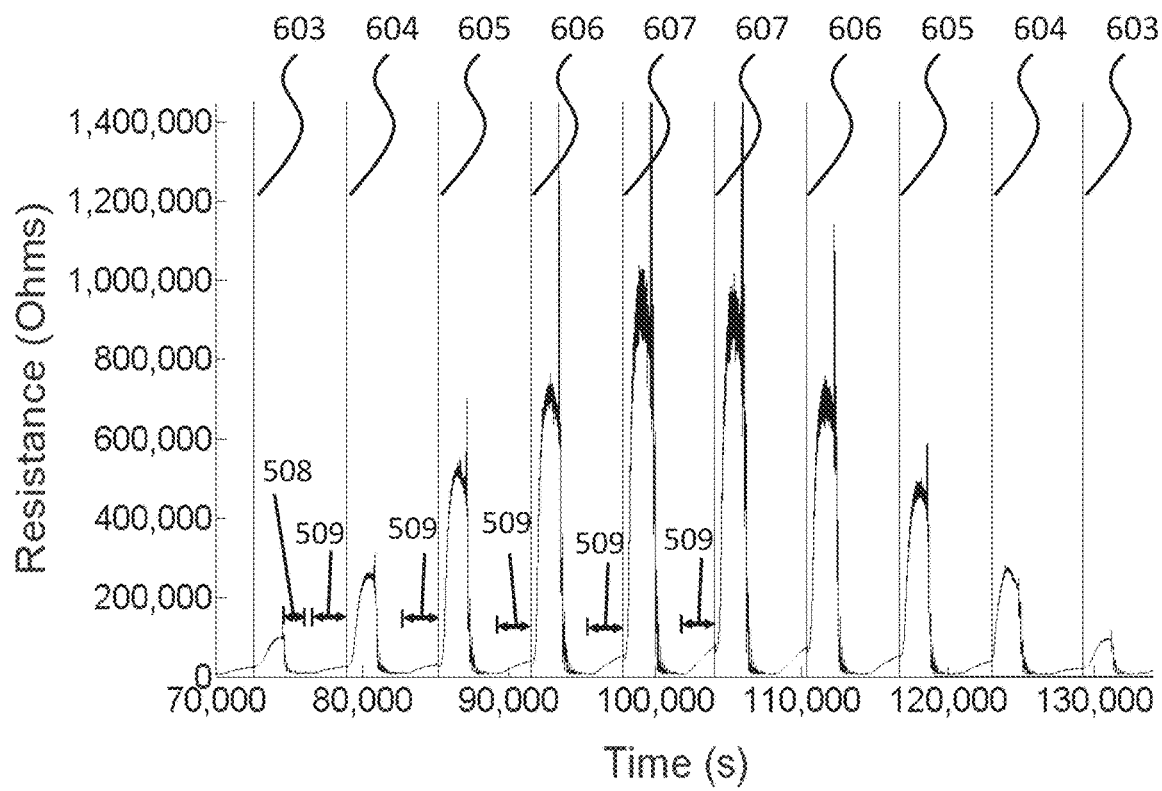
Figure 6C:
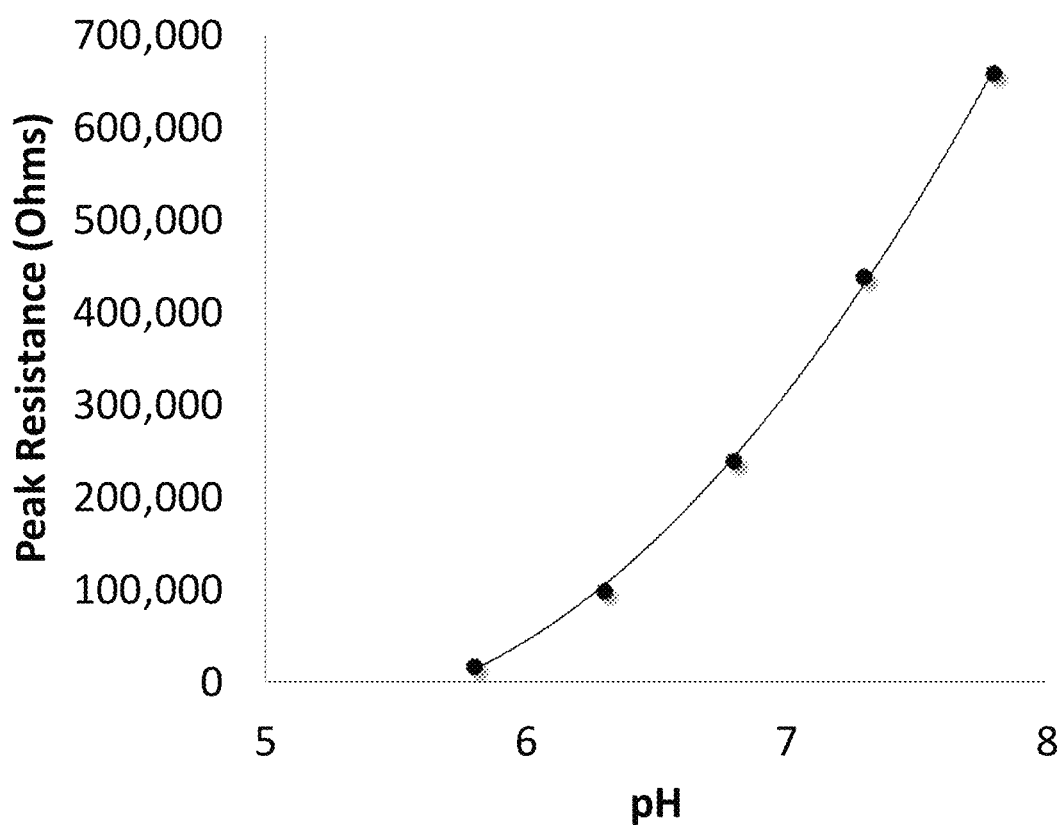

FIGS. 6A-6C illustrate sensor response profiles determined during analysis of liquid samples having the same analyte species 112 but at different concentrations, sensor responses to samples having different pH values, and a plot of peak sensor responses to liquid samples having different pH values. FIG. 6A illustrates sensor responses determined during analysis of liquid samples having the same analyte species 112 but at different concentrations. In some embodiments, different concentrations of the same species of ion or molecule analyte can affect the conductivity of porous conductive film 103 of a single sensor 110 in essentially the same manner. In this exemplary embodiment, apparatus 100 comprised semipermeable barrier 301, and test samples were added to subchamber 302. FIG. 6A illustrates the responses of the single sensor to four repeated exposures 608 of a series of liquid samples having different concentrations of the short chain fatty acid molecule propionic acid in deionized water. The repeated exposures 608 included exposure to liquid samples of increasing concentrations (region 601) of propionic acid (0 mM, 10 mM, 25 mM, 50 mM, 75 mM, and 100 mM) followed by exposure to liquid samples of decreasing concentrations (region 602) of propionic acid (100 mM, 75 mM, 50 mM, 25 mM, 10 mM, 0 mM). After each sample exposure, sensor 110 was washed as described for FIG. 5 using a wash period 508 and dwell period 509. The shapes of the graphically depicted sensor response profiles determined with each concentration of propionic acid exhibited a similar, repeatable trend. Also, for the series of diluted analyte samples, the electrical conductivity of porous conductive film 103 was affected in a similar manner upon repeated exposures to the same wash liquids during wash period 608.

FIG. 6B illustrates the effect of different buffered pH solutions (over a pH range of 5.8-7.8) on porous conductive film 103 of a single sensor 110. In this exemplary embodiment, apparatus 100 comprised semipermeable barrier 301, and test samples were added to subchamber 302. Here, the concentration of $H^+$ ions was varied by changing the relative ratios of $NaH_2PO_4$ and $Na_2HPO_4$ in a buffer system. The response profiles of the sensor were first determined for liquid samples of increasing pH—5.8, 603; 6.3, 604; 6.8, 605; 7.3, 606; 7.8, 607. Response profiles were next determined for the liquid samples in order of decreasing pH. Vertical lines 603-607 represent the time of addition of each liquid sample to subchamber 302. After each sample exposure, sensor 110 was washed as described for FIG. 5 using a wash period 508 and dwell period 509. In this example, the ion analytes 112 in the liquid test samples, interacting with porous conductive film 103, caused an increase in resistance of porous conductive film 103. Whereas, sensor washing during wash period 508 and sensor dwell during dwell period 509 after liquid sample exposure caused a decrease in the resistance of porous conductive film 103 prior to exposure of the sensor to the next test sample.

In this experimental example, although wash period 508 included exchanges of wash solution in both subchambers 302 and 303, small increases in resistance of porous conductive film 103 were observed during dwell period 509. Without being bound by theory, one explanation for this phenomenon is that some test sample liquid (with analyte) may be retained in semipermeable barrier 301 (here a dialysis membrane) throughout the wash regimen and can subsequently diffuse out of the membrane or can subsequently be diluted when additional liquid is added to subchamber 303. The new, lower concentration of analyte 112 in the final wash sample could be responsible for the measured increase in resistance of porous conductive film 103 observed while resting in the dwell period 509. As illustrated in FIG. 6B, the phenomenon was evident with all test liquid samples of different pH values. However, the sensor response during dwell period 509 differed depending on the pH of the test sample and may be influenced by the relative concentrations of $H^+$, $H_2PO_4^-$, and $HPO_4^{2-}$ ions in equilibrium with porous conductive film 103.

In some embodiments, factors that can affect the conductivity of porous conductive film 103 (i.e., affect the sensor response) during liquid sample analysis include the rates of diffusion of ions and molecules to the surface of porous conductive film 103, rates of adsorption to and desorption from the surface of porous conductive film 103 of each ion or molecule species in the liquid sample, the effect of each ion or molecule species on charge carriers in the $MO_x$ structures (i.e., electron withdrawal or electron donation), exchange state dielectric stabilization (i.e., water dipole coordination), competition for exchange sites on the surfaces of $MO_x$ structures 104, ionic and molecular species orientation and rate of change of orientation, and the amount of solvated ion or molecule species in the liquid which may determine the concentration gradient.

In some aspects, such as for example during analysis of large biomolecules, diffusion through interstitial liquid among $MO_x$ structures 104 of the large biomolecule analytes 112 may be significantly affected by one or more of liquid solution sample diffusion, liquid sample convection, and liquid sample advection, which may also affect electrical conductivity of porous conductive film 103. Changes in the electrical conductivity of porous conductive film 103 during interaction of the large biomolecule analytes 112 with the film 103 may also be influenced by one or more of adsorption and desorption rates during binding of the biomolecule analytes 112 to $MO_x$ structures 104, the orientation of chemical functional groups (e.g., carboxylate or amine groups) on the large biomolecule analytes 112 with the surfaces of $MO_x$ structures 104, and the net carrier exchange quantity and rate between bound biomolecule analytes 112 and porous conductive film 103.

FIG. 6C illustrates an example of the peak resistance value reached by porous conductive film 103 when exposed to solutions having different pH values in which a polynomial fit can be used as an empirical tool to extrapolate unknown pH of a solution. The dependence on pH follows a second order polynomial trend with pH over this pH range.

Figure 7:
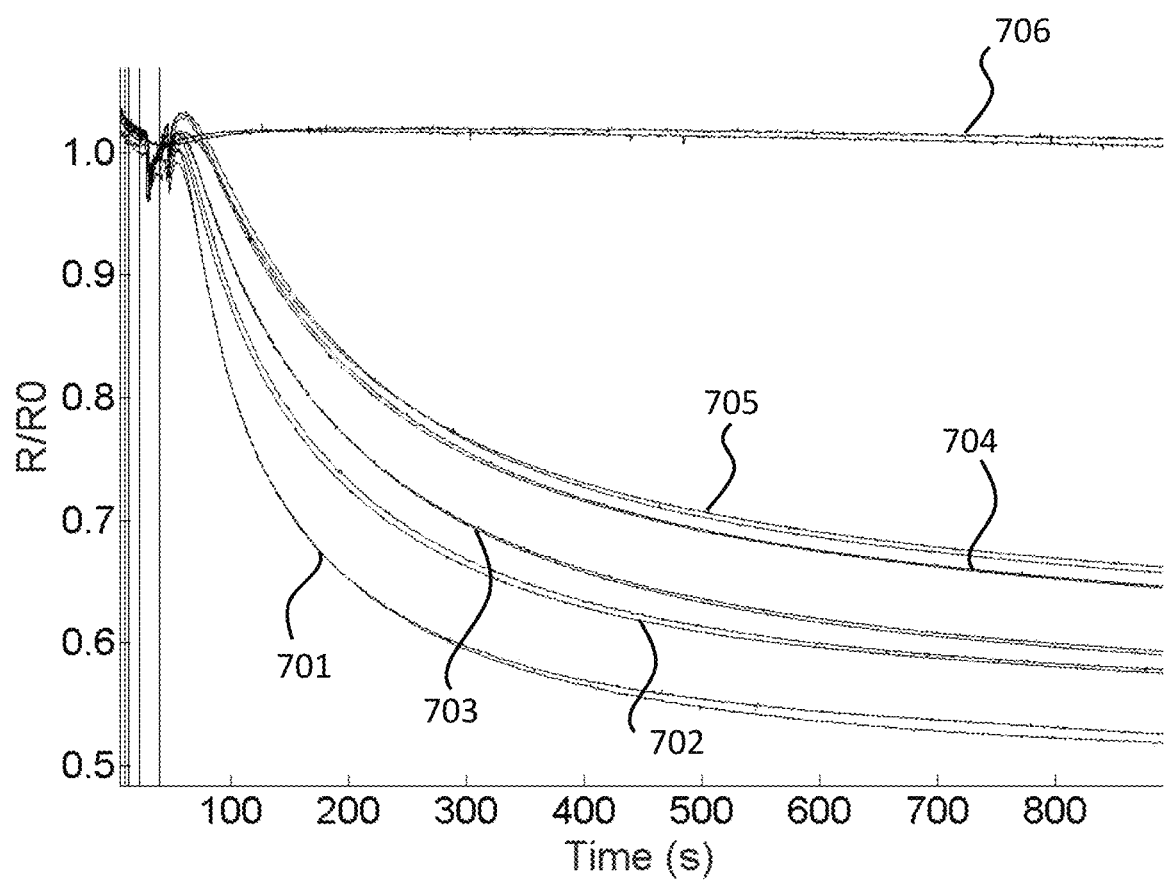
FIG. 7 illustrates normalized sensor responses for liquid test samples comprising various concentrations of butyric acid in deionized water.

FIG. 7 illustrates normalized sensor responses for liquid test samples comprising various concentrations of butyric acid in deionized water. In this example, electrical responses to the various liquid test samples were determined in a randomized order. Evaluation of sensor response to replicate test samples provided in a randomized order demonstrated that duplicate samples having the same concentration of analyte affected conductivity of porous conductive film 103 in the same manner. Butyric acid samples included 10 mM, 701; 25 mM, 702; 50 mM, 703; 75 mM, 704; and 100 mM, 705. Sensor response profiles for deionized water 706 are also shown and were determined between analyses of different concentrations of butyric acid followed by consecutive sensor washes. The normalized sensor response to water 706 remained unity since the fluid exchange did not lead to changes in solvated molecule or ion concentrations.

Figure 8:
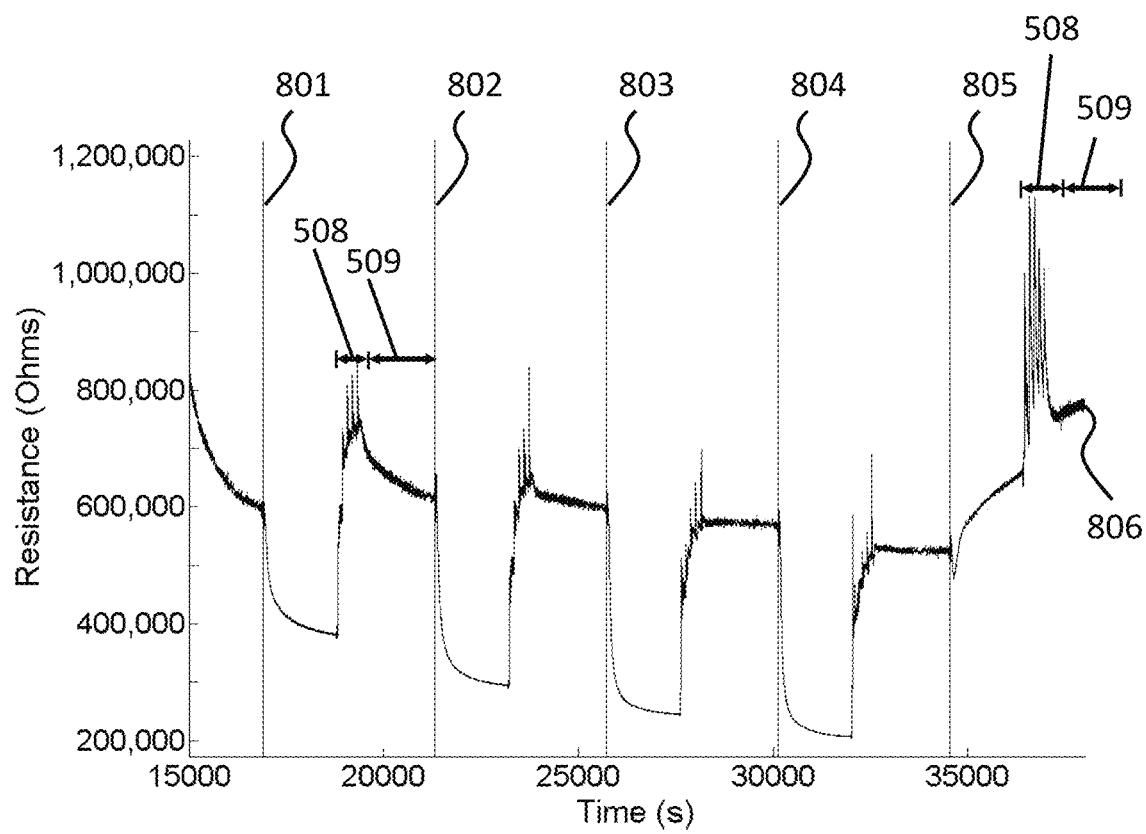
FIG. 8 illustrates resistance of a porous conductive film measured during exposure to a liquid sample comprising a divalent salt, magnesium acetate, and to liquid samples comprising various concentrations of the monovalent salt, sodium chloride.

FIG. 8 illustrates resistance of a porous conductive film 103 measured during exposure to a liquid sample comprising a divalent salt, magnesium acetate, and to liquid samples comprising various concentrations of the monovalent salt, sodium chloride. Shown in the figure is the response 806 of a single sensor 110 after addition of liquid test samples. Vertical lines indicate the time of addition of liquid samples comprising 0 mM NaCl, 801; 25 mM NaCl, 802; 50 mM NaCl, 803; 100 mM NaCl, 804; and 25 mM magnesium acetate ($Mg(CH_3COO)_2$), 805. Sensor 110 response observed with sodium chloride samples are similar to those shown in FIG. 5. The observed sensor response on exposure to magnesium acetate displays a different trend from the response observed for sodium chloride including differences during wash period 508 and dwell period 509. The magnesium acetate solution affected resistance of porous conductive film 103 differently than did the sodium chloride solutions. NaCl caused a resistance decrease, which may be the result of charge carrier donation from NaCl, or more specifically solvated chloride ion ($Cl^-$) to $MO_x$ structures 104. Conversely, the divalent cation $Mg^{2+}$ and organic anion $CH_3COO^-$ caused a resistance increase, which may be the result of charge carrier extraction from $MO_x$ structures to the adsorbed ions or molecules.

Figure 9:
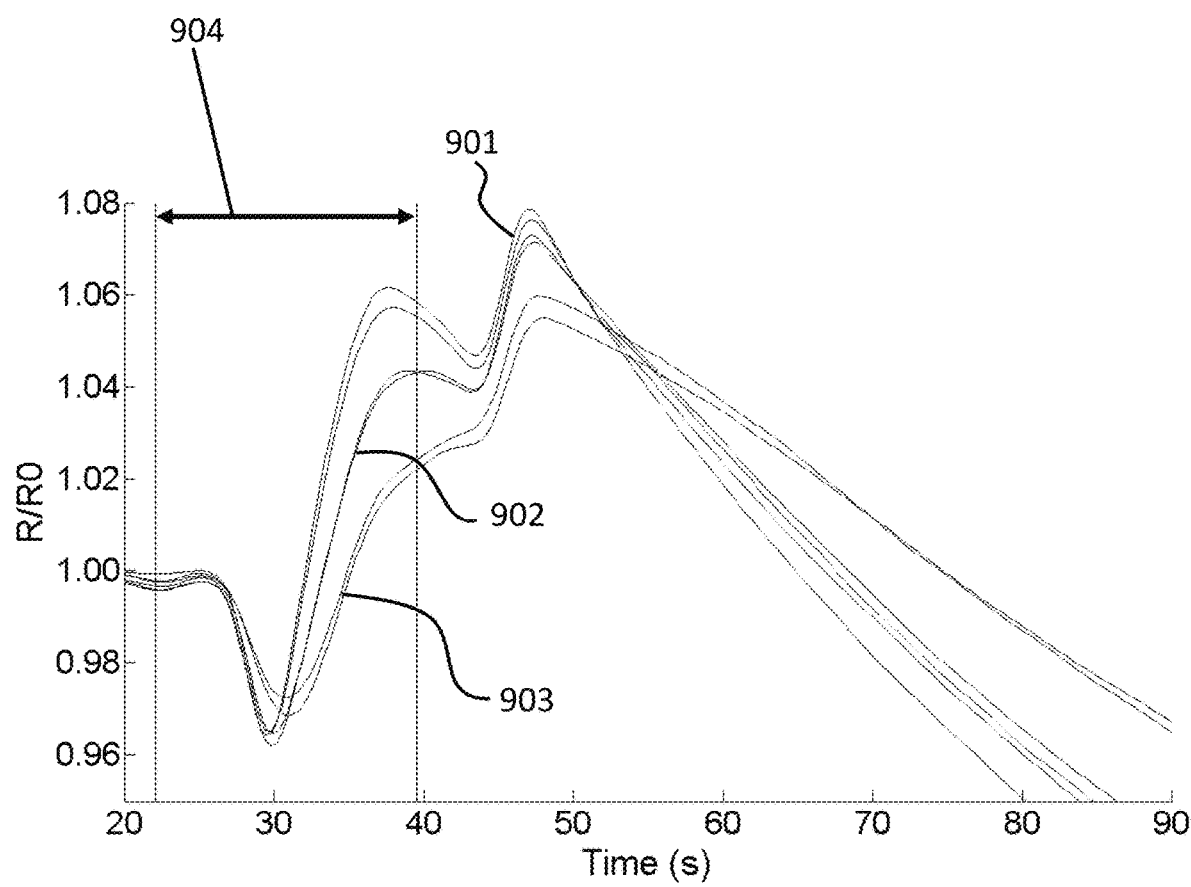
FIG. 9 illustrates a series of six sensor response profiles, which includes two replicates each for liquid samples comprising the same concentrations of different short chain fatty acid molecules.

In some embodiments, chemically similar analytes 112 may cause distinct changes in the electrical conductivity of porous conductive film 103, during liquid sample analysis. FIG. 9 illustrates a series of six sensor response profiles, which includes two replicate profiles each for liquid samples comprising 901, 100 mM acetic acid, a weak acid in equilibrium with conjugate base acetate; 902, 100 mM propionic acid, a weak acid in equilibrium with conjugate base propionate; or 903 100 mM butyric acid, a weak acid in equilibrium with conjugate base butyrate. Liquid samples were analyzed with the same sensor 110 and were normalized and offset in time to create the overlay view. Porous conductive film 103 responded similarly to separate test samples of the same analytes 112 and responded differently to the different molecular species analytes 112 of short chain fatty acids. In some embodiments, liquid samples were pumped into subchamber 302 over a selected period of time. In this example, the period of time corresponding to sample addition 904 has been enlarged. Here, test samples were added to subchamber 302 during the time period 904. At the beginning of period 904, the sensor response profiles were similar for the different test samples. As a test sample liquid entered and exchanged with liquid in subchambers 302 and 303 the sensor response to the different analytes 112 changed. Different test samples displayed differences in sensor response (901 vs. 902 vs. 903) during this time period, indicating that the conductivity of porous conductive film 103 was affected differently by the different short chain fatty acids and their respective conjugate bases.

Figure 10:
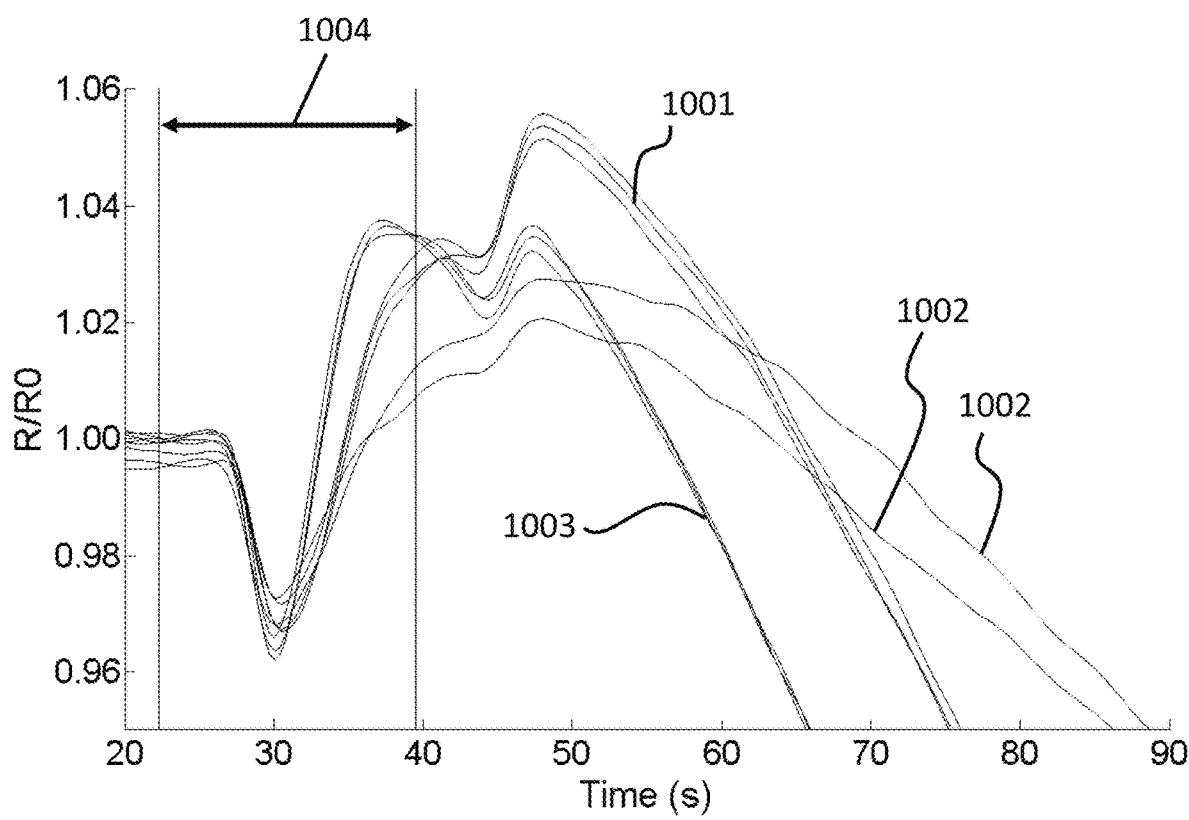
FIG. 10 illustrates a series of eight sensor response profiles, which includes replicate profiles for liquid samples comprising the same concentrations of molecules, all molecules having three carbon atoms but having different oxidation states of the central carbon side chain.

FIG. 10 illustrates a series of eight sensor response profiles, which includes replicate profiles for liquid samples comprising the same concentrations of ion molecule analytes 112, all analytes 112 having three carbon atoms but having different oxidation states of the central carbon side chain. Three replicate sensor response profiles are shown for 100 mM propionic acid 1001, which is a three-carbon organic acid having two hydrogen (H) atoms bound to the central carbon atom and in equilibrium with its conjugate base, propionate. Two replicate sensor response profiles are shown for 100 mM lactic acid 1002, which is a three-carbon organic acid having an alcohol (—OH) group and a H atom bound to the central carbon and in equilibrium with its conjugate base, lactate. Three replicate sensor response profiles are shown for 100 mM pyruvic acid 1003 which is a three-carbon organic acid having a carbonyl oxygen (=O) bound to the central carbon and in equilibrium with its conjugate base, pyruvate. Liquid samples were analyzed with the same sensor 110 and were normalized and offset in time to create the overlay view. Porous conductive film 103 responded similarly to separate test samples of the same analyte species 112 and responded differently to the different ionic or molecular species analytes 112. In this example, the period of time corresponding to sample addition 1004 has been enlarged. At the beginning of period 1004, the sensor response profiles were similar for the different test samples. As a test sample liquid entered and exchanged with liquid in subchambers 302 and 303 the sensor response to the different analytes changed. The different test samples displayed different sensor responses during this time period, indicating that the conductivity of porous conductive film 103 was affected differently by the different three-carbon molecules (1001 vs. 1002 vs. 1003).

Figure 11:
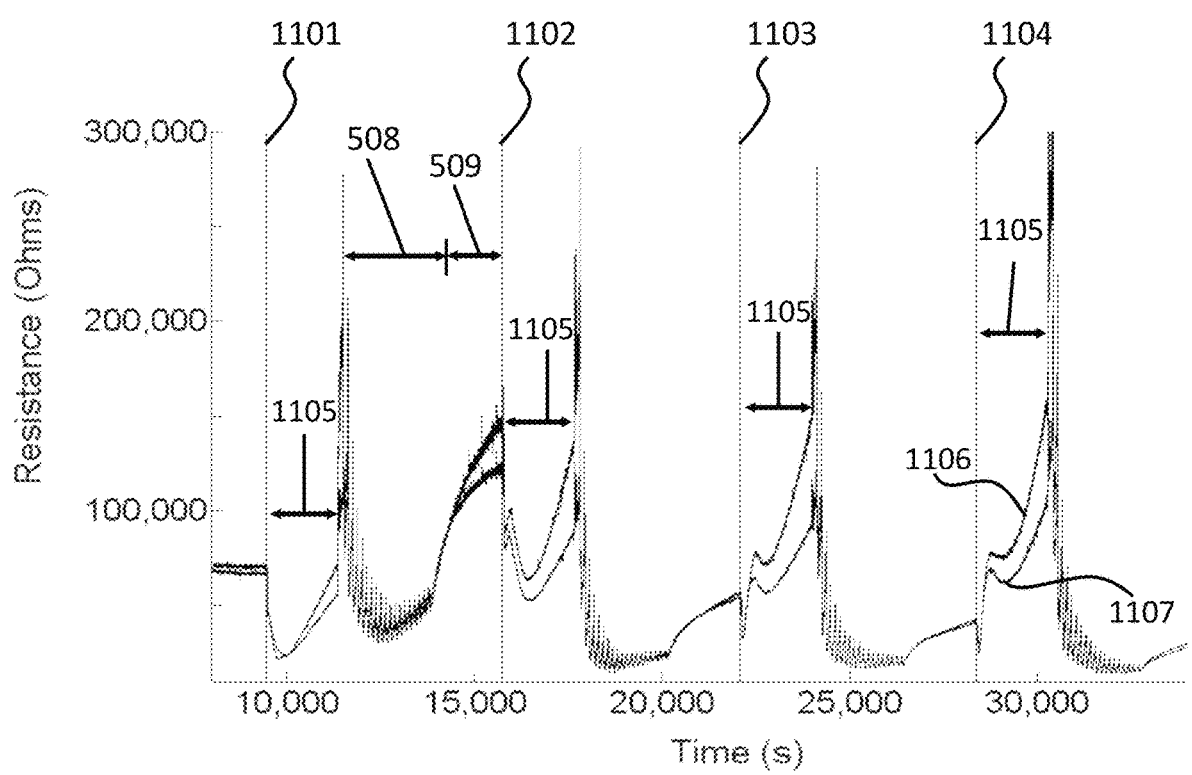
FIG. 11 illustrates sensor response profiles determined during consecutive exposure of two different sensors to liquid test samples comprising one of four deoxynucleotide triphosphates.

In another exemplary embodiment, sensor response profiles from the analysis of liquid samples comprising selected biomolecules were observed to be distinct. FIG. 11 illustrates sensor response profiles 1106 and 1107 determined during consecutive exposure of two different sensors 110 to liquid test samples comprising one of four deoxyribonucleoside triphosphates (dNTPs). Sensor response profiles were determined with 10 mM deoxythymidine triphosphate 1101, 10 mM deoxyguanosine triphosphate 1102, 10 mM deoxyadenosine triphosphate 1103, and 10 mM deoxycytidine triphosphate 1104. Vertical lines represent the time of addition of each liquid test sample. After each test sample addition, the electrical response of porous conductive film 103 was measured for a selected period of time 1105 in the presence of the test sample. Each test sample exposure was followed by an extended wash period 508 and dwell period 509. In some embodiments, distinguishing nucleotide molecules and/or other reaction products or by-products of nucleic acid synthesis can be useful in embodiments for monitoring the progress of a nucleic acid polymerization reaction, such as for example when determining the sequence of a nucleic acid.

Figure 12A:
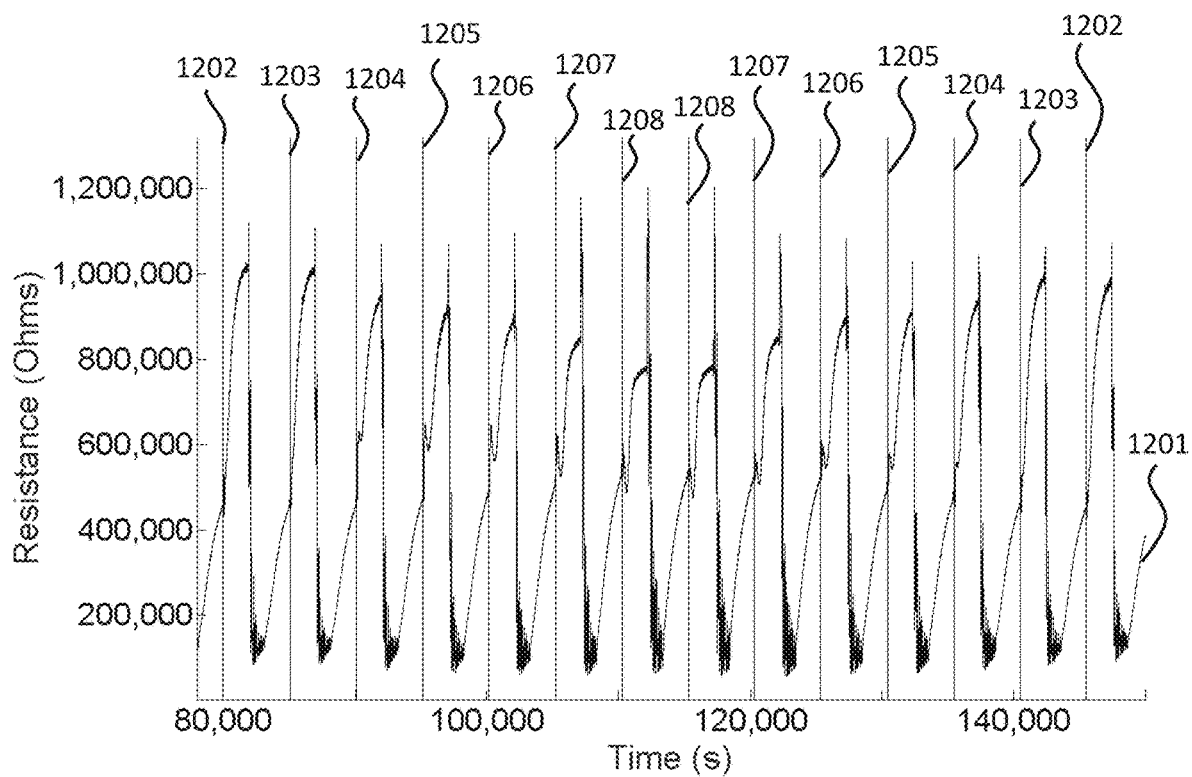
FIGS. 12A-12B illustrate the measured resistance of a porous conductive film in a single sensor during consecutive exposures to phosphate buffered saline liquid test samples having different concentrations of NaCl and an enlarged view of selected sensor response profiles.
Figure 12B:
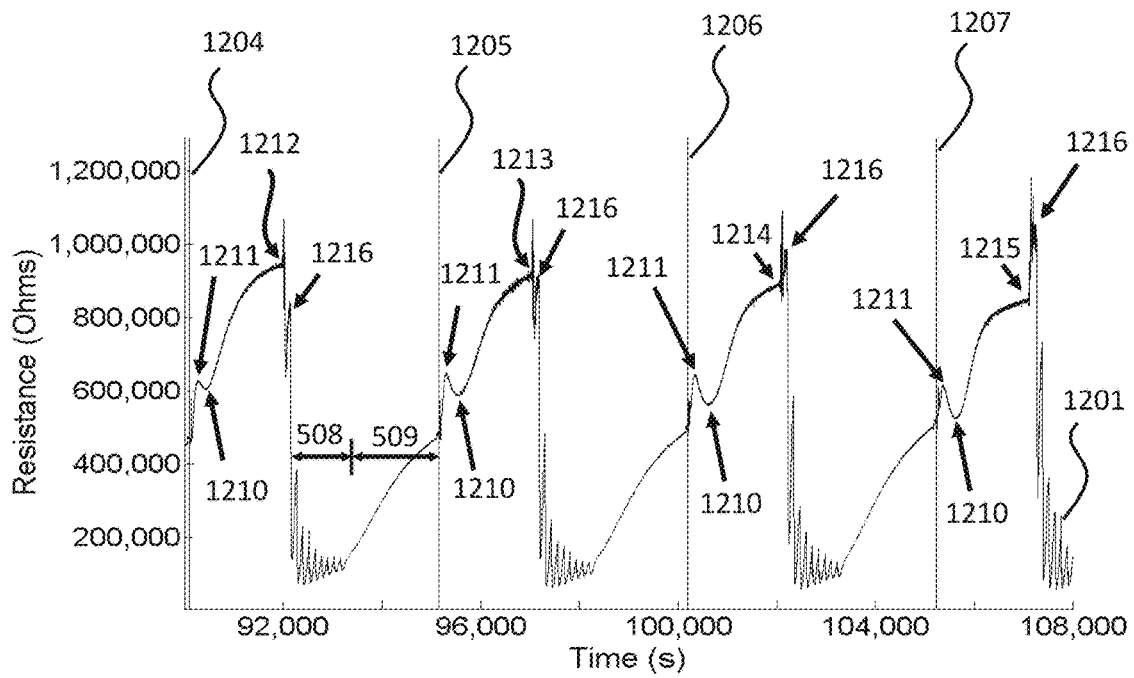

In some embodiments, sensor response profile analysis of a composite mixture, comprising a plurality of different analyte species 112 that may represent different chemical classes, can be useful for identifying a plurality of ion or molecule analytes 112. In some aspects, sensor response profile data can be deconvoluted. In some aspects, identification of different analyte species 112 may be based on the relative differences in diffusion rates of the different analytes to the surfaces of $MO_x$ structures 104. FIGS. 12A-12B illustrate the measured resistance of a porous conductive film 103 in a single sensor 110 during consecutive exposures to phosphate buffered saline liquid test samples having different concentrations of NaCl and an enlarged view of selected sensor response profiles. FIG. 12A illustrates sensor response profile 1201 that depicts the measured resistance of porous conductive film 103 in the single sensor during consecutive exposures to phosphate buffered saline liquid test samples having different concentrations of NaCl. Vertical lines 1202-1208 represent the time of addition of each test sample to subchamber 302 Test samples were phosphate buffered saline solutions comprising 0.01 mM NaCl, 1202; 1 mM NaCl, 1203; 10 mM NaCl, 1204; 25 mM NaCl, 1205; 50 mM NaCl, 1206; 100 mM NaCl, 1207; and 200 mM NaCl, 1208. Test samples were consecutively analyzed in order of increasing NaCl concentration then in order of decreasing NaCl concentration. After addition of each test sample liquid, porous conductive film 103 exhibited an initial decrease in resistance, and the magnitude of the decrease in resistance became more prominent as the concentration of NaCl increased, illustrating the effect of a single analyte in an analyte mixture.

FIG. 12B illustrates an enlarged view of a portion of sensor response profile 1201 (shown in FIG. 12A) from the analysis of liquid samples 1204-1207. In this enlarged view, after each sample addition a slight increase in resistance 1211 was observed followed by a resistance decrease 1210, which occurred at a fixed time after increase 1211. Resistance decrease 1210 was likely due to the NaCl in the test sample liquid, as the magnitude of resistance decrease 1210 corresponded to the concentration of NaCl. A maximum observed resistance (1212, 1213, 1214, 1215) occurred after each sample addition and after sensor equilibration with phosphate buffer, just prior to the first wash. With increasing concentrations of NaCl in the test samples, the magnitude of maximum resistances (1212-1215) decreased. This trend was observed for all test samples 1202-1208. Without being bound by theory, this may have resulted from solvated Cl⁻ ions diffusing rapidly to surface sites on $MO_x$ structures 104, followed by a less rapid diffusion of phosphate ion to the surface sites. Competition for surface sites between bound Cl⁻ and phosphate buffer led to displacement of chloride ions from surface sites on $MO_x$ structures 104 due to the phosphate ions having a stronger binding affinity for surface sites on $MO_x$ structures 104. Phosphate ions subsequently interacted with the space charge layers of $MO_x$ structures 104 until the phosphate coordination reached equilibrium. The shape of the sensor response profile over time and the overall change in the sensor response magnitude at equilibrium was likely influenced by the NaCl concentration. Sensor response data in FIG. 12B also suggested that the concentration of sodium chloride impacted the sensor response that was observed during wash period 508. (For ease of viewing 508 and 509 are only depicted for test sample 1204.) Higher concentrations of NaCl in the phosphate buffer resulted in a progressively higher "resistance spike" 1216 at the beginning of the first wash during wash period 508. FIGS. 12A-12B demonstrate numerous aspects of a sensor response profile that can be used for determining the chemical composition and concentrations of ion or molecule analytes 112 in liquid samples.

Figure 13:
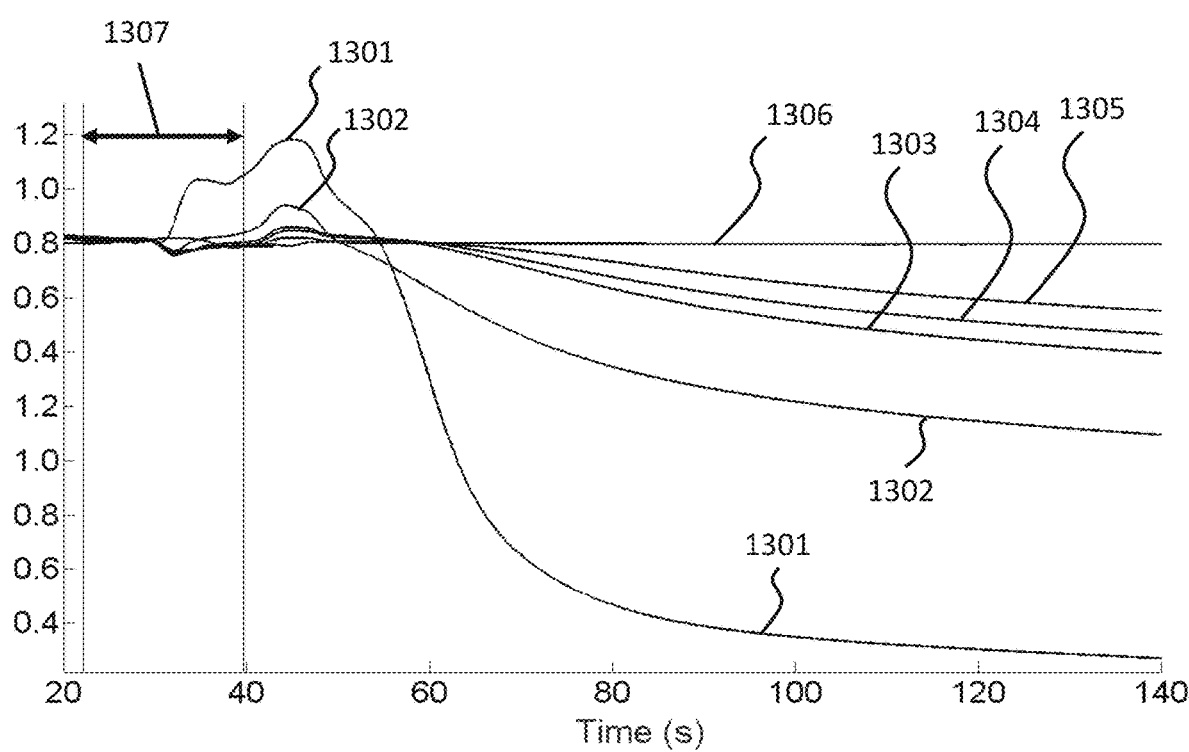
FIG. 13 illustrates sensor response profiles determined during the analysis of liquid samples comprising mixtures of acetic acid and butyric acid and their conjugate bases.

FIG. 13 illustrates sensor response profiles determined during the analysis of liquid samples comprising mixtures of acetic acid and butyric acid and their respective conjugate bases acetate and butyrate. The sensor response profiles are normalized and offset in time to create an overlay plot. The samples analyzed included 100% 100 mM acetic acid, 1301; 75% 100 mM acetic acid:25% 100 mM butyric acid, 1302; 50% 100 mM acetic acid:50% 100 mM butyric acid, 1303; 25% 100 mM acetic acid:75% 100 mM butyric acid, 1304; 100% 100 mM butyric acid, 1305; and deionized water, 1306. Graphically depicted sensor response profiles of liquid samples comprising mixtures of the two molecular compounds were observably distinct from each other and from sensor response profiles determined with unmixed samples. Here, test samples were added to subchamber 302 during the time period 1307. At the beginning of period 1307, the sensor response profiles were similar for the different test samples. As a test sample liquid entered and diffused through subchamber 303 the sensor response to an analyte changed. Different test samples displayed differences in sensor response during the latter part of time period 1307, and differences in sensor response to the different mixtures persisted at later time points on the sensor response profile, indicating that the conductivity of porous conductive film 103 was affected differently by the different mixtures of the two chemical compounds.

Figure 14A:
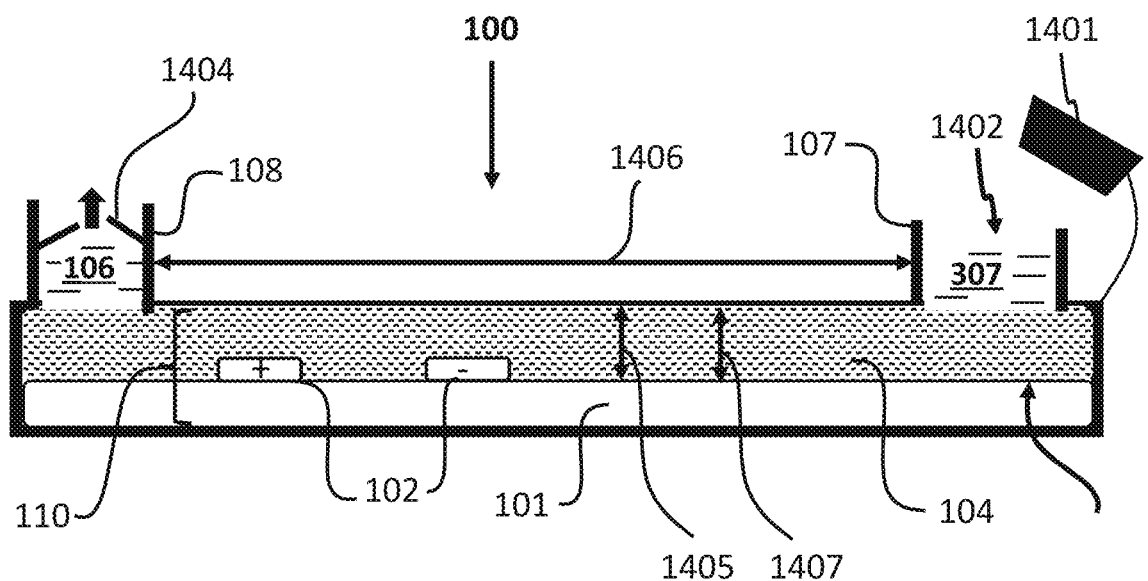
FIGS. 14A-14C illustrate a schematic depiction of an exemplary embodiment of an apparatus configured for lateral sample flow, a top view of a porous conductive film, and a top view of a porous conductive film having a narrow width.
Figure 14B:
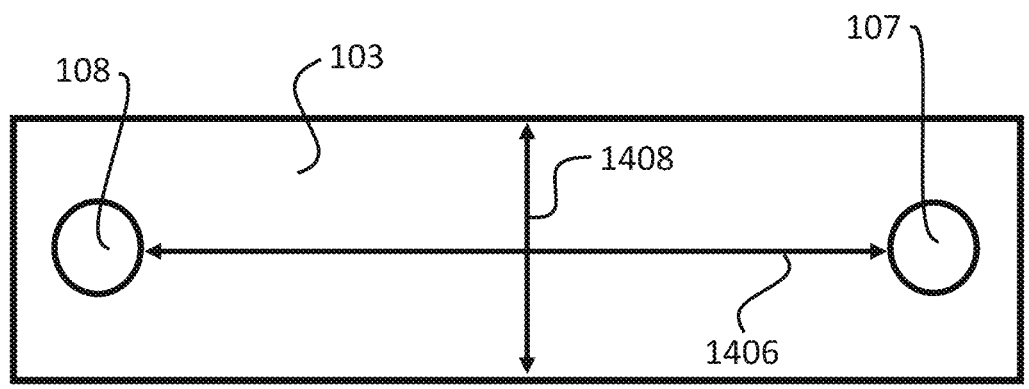
Figure 14C:
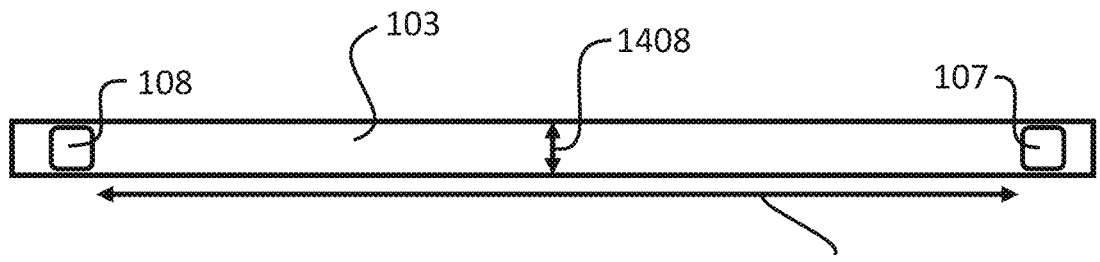

FIGS. 14A-14C illustrate a schematic depiction of an exemplary embodiment of an apparatus 100 configured for lateral sample flow, a top view of porous conductive film 103, and a top view of porous conductive film 103 having a narrow width.

In some embodiment, lateral flow of a liquid sample through chamber 109 may be enhanced by using an apparatus 100 having selected dimensions for selected element. In some aspects, lateral flow of a liquid sample can be enhanced when the ratio of the submersion liquid height 1405 of submersion liquid 106 present in chamber 109 to the porous conductive film length 1406 is greater than or equal to about ¹⁄₁,₀₀₀,₀₀₀ and less than or equal to about ½. Ratio 1405/1406 may have any value therebetween. For an apparatus 100 configured for lateral sample flow, submersion liquid height 1405 is defined as the distance from the surface of substrate 101 on which porous conductive film 103 is positioned to the furthest extent of submersion liquid 106 and is measured perpendicularly from the surface of substrate 101. Porous conductive film length 1406 is defined as the length of porous conductive film extending between inlet port 107 and outlet port 108. In some exemplary aspects, submersion liquid height 1405 can range from about 1 mm to about 3 mm and porous conductive film length 1406 can range from about 3 cm to about 10 cm, such that ratio 1405/1406 is from about 1/100 to about 1/10. Porous conductive film thickness 1407 as used herein represents the vertical span of porous conductive film 103, typically from the surface of substrate 101 on which porous conductive film 103 is positioned to the furthest extent of porous conductive film 103 and is measured perpendicularly from the surface of substrate 101. In aspects where porous conductive film fills housing 105, submersion liquid height 1405 will generally be the same as porous conductive film thickness 1407.

In some embodiments for use of apparatus 100 in a lateral flow format, liquid sample 307 can be introduced to chamber 109 through inlet port 107 into sample reservoir region 1402. Submersion liquid 106 in chamber 109 would be expelled from outlet port 108 by way of check valve 1404. In some aspects, the volume of liquid sample 307 added to chamber 109 can be chosen so as to have a selected amount of a known ion or molecule or to have an amount of an unknown ion or molecule analyte 112 that is to be determined. In some aspects, the volume of liquid sample 307 may be chosen based on an expected concentration range of an unknown ion or molecule analyte 112 in liquid sample 307 that is a test sample. The volume of liquid sample 307 that is added to chamber 109 may be low, such as for example >0% and <0.01% of the volume of submersion liquid 106 chamber 109, or the volume of liquid sample 307 may be chosen so as to completely replace the volume of submersion liquid 106 in chamber 109, or the volume of liquid sample 307 may be any volume that is between those exemplary amounts.

In some embodiments, a sensor response profile may be determined during the flow of liquid sample 307 from sample reservoir region 1402 through outlet port 108. In some aspects, a sensor response profile may be determined during a period of time in which liquid sample 307 is exposed to sensor 110 and moving laterally from a first end of porous conductive film 103 near sample reservoir region 1402 to a second end of porous conductive film 103 distal to sample reservoir region 1402 and near outlet port 108. In some aspects, a sensor response profile may be determined during a time period that is after liquid sample 307 has replaced submersion liquid 106.

In some embodiments, solvated ions or molecules may interact with porous conductive film 103 during flow of liquid sample 307. In these aspects, the volume of liquid sample 307 can be such that liquid sample 307 flows through porous conductive film 103 and across one or more electrode pairs 102. In some embodiments the volume of liquid sample 307 may not be sufficient to cause ion or molecule analytes 112 to interact with porous conductive film 103. In these aspects, solvated ions or molecules may diffuse across one or more electrode pairs 102 of sensors 110 in a serial manner, whereby each interaction of solvated ions or molecules with sensor 110 occurs one after another along the porous conductive film 103 in housing 105. In some lateral flow embodiments, solvated ions and molecules interact with one or more sensors 110 along porous conductive film 103 during flow of test sample liquid 307. In these embodiments, the volume of test sample liquid exchanged with submersion liquid 106 is sufficiently large so that test sample liquid 307 flows across one or more electrode pairs 102 of sensors 110. In some lateral flow embodiments, the volume of test sample liquid 307 exchanged with submersion liquid 106 is initially insufficient for solvated molecules and ions to contact sensors 110 directly. As solvated molecules and ions diffuse throughout submersion liquid 106 they can diffuse across one or more electrode pairs 102 of sensors 110 in a serial manner, such that each interaction of solvated ions or molecules with sensor 110 occurs sequentially along porous conductive film 103 in housing 105.

In some embodiments of apparatus 100 configured for lateral sample flow, multiple electrode pairs 102 can be positioned along porous conductive film 103 thereby forming an array of sensors configured to measure an electrical property of porous conductive film 103 during diffusion of a liquid sample from a sample reservoir region 1402 of chamber 109 through the interstitial volume of liquid in porous conductive film 103 to outlet port 108. In some aspects, check value 1404 can be figured to block liquid flow until a flow rate threshold is reached, either by buildup of pressure in chamber 109 or by application of suction to outlet port 108. The apparatus 100 embodiment shown in FIG. 14A further comprises sealing mechanism 1401, which can be a stopper, screw cap, press fit cap, septum, stopcock, manual or electronic valve, multi-way valve, or any of numerous other closure devices.

FIG. 14B is a top down view of porous conductive film 103 showing the locations of inlet port 107 and outlet port 108 in housing 105. In some embodiments, porous conductive film width 1408 may span the width of housing 105 and may be from about 10 µm to about 100 cm. In some embodiments, as in FIG. 14B, a porous conductive film 103 in a lateral flow apparatus 100 having a relatively larger width 1408, for example a width greater than or equal to about 1 mm, may sometimes be referred to as a strip, film, paper or plate. FIG. 14C is a top down view of porous conductive film 103 configured with a relatively narrower porous conductive film width 1408. In some embodiments, a porous conductive film 103 in a lateral flow apparatus 100 and having a narrower width, such as for example a width ranging from about 10 µm to about 1 mm may sometimes be referred to as a channel, a microchannel, a capillary, or a microcapillary.

In some embodiments of apparatus 100 configured for lateral flow, porous conductive film length 1406 can be from about 1 µm to about 1 km and can be of any length therebetween. Porous conductive film 103 may have any length 1406 that is suitable for analysis of ion or molecule analytes 112 in a liquid sample 307 according to methods described herein. In some embodiments, housing 105 can be shaped as a long thin channel (similar to the shape of a thin glass capillary tube) or can be configured as a length of flexible material such as for example a flexible plastic tube wherein the tube length could range from about 10 cm to about several meters. Some examples of flexible plastic tubing include columns used in techniques such as column chromatography and high performance liquid chromatography or HPLC.

Figure 15A:
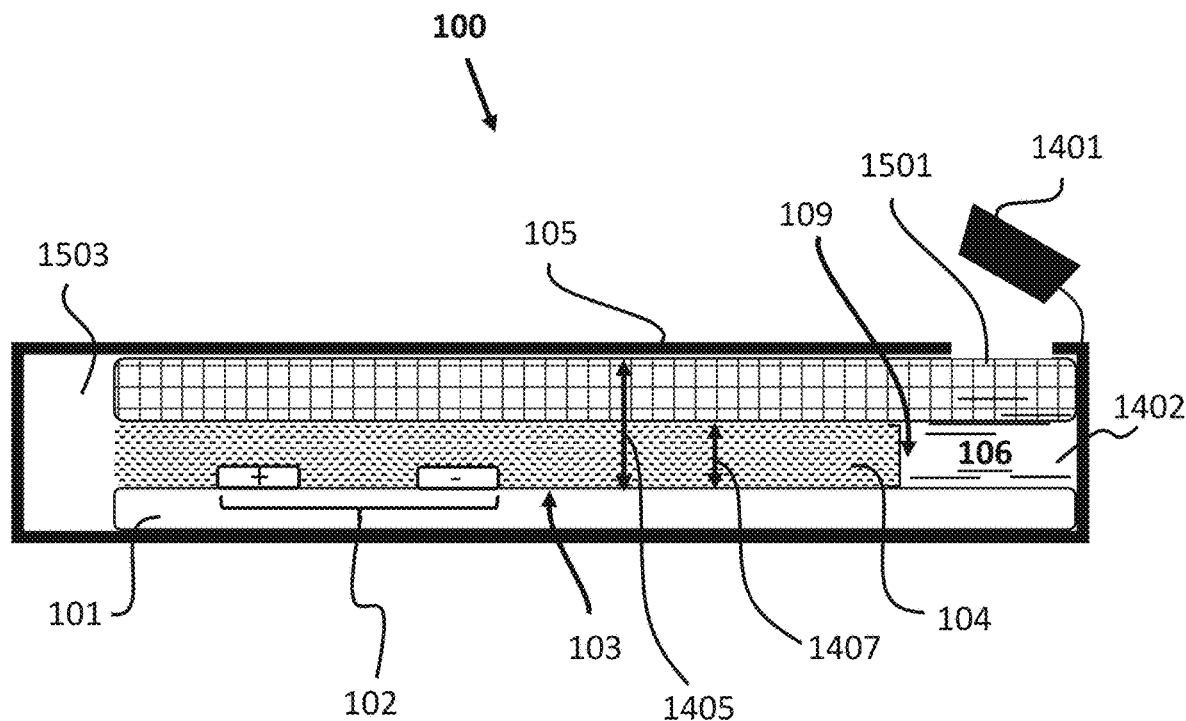
FIGS. 15A-15B is a schematic illustration of an embodiment of an apparatus configured for lateral sample flow and for use in a lateral flow test strip format and an exemplary method for manufacturing an apparatus comprising a sensor configured in a lateral flow test strip format.
Figure 15B:
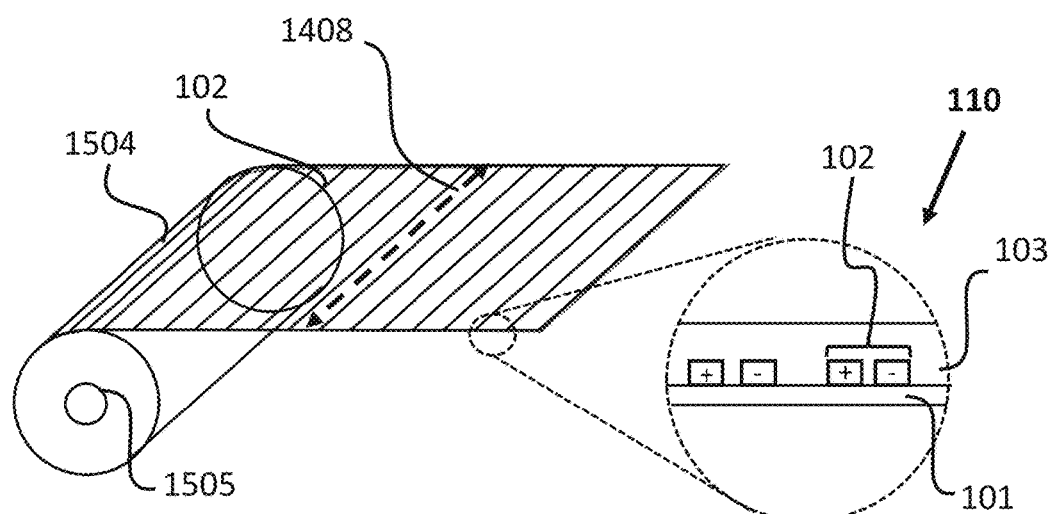

FIGS. 15A-15B is a schematic illustration of an embodiment of apparatus 100 configured for lateral sample flow and for use in a lateral flow test strip format and an exemplary method for manufacturing an apparatus comprising a sensor configured in a lateral flow test strip format. In some embodiments, apparatus 100 may further comprise a semipermeable barrier 301 positioned to be on top of and in contact with porous conductive film 103 and semipermeable barrier 301 may be a wicking material 1501. In some aspects, wicking material 1501 is positioned to be in contact with porous conductive film 103. In some aspects, wicking material 1501 may be a membrane or fiber. In some embodiments, wicking material 1501 can be in fluid communication with chamber 109. Apparatus 100 can comprise a wicking material 1501 that is a lateral flow membrane, which can be configured to be in fluid contact with test sample reservoir 1402. In the exemplary embodiment depicted in FIG. 15A, wicking material 1501 is depicted as being in contact with porous conductive film 103 and in some aspects can be selected to have a higher wicking rate than does porous conductive film 103 so as to be functional for controlling the wicking rate of liquid sample 307 across porous conductive film 103 toward liquid receptacle 1503. In some embodiments, wicking material 1501 is selected to have a high binding affinity for ion or molecule analytes 112 which may act to increase the dynamic range of detection of ion or molecule analytes. In some aspects, binding of solvated ions or molecules present in liquid sample 307 to semipermeable membrane 301 or wicking material 1501 may cause a decrease in the concentration of solvated ions or molecules in liquid sample 307. Binding of solvated ions or molecules to semipermeable barrier 301 or to wicking material 1501 may affect the sensor response profile. Ions or molecules bound to semipermeable barrier 301 or wicking material 1501 may not cause a measurable change in an electrical property of porous conductive film 103. Rather, in some aspects, a decrease in the concentration of solvated ions or molecules in liquid sample 307 may be measured as a change in concentration of an ion or molecule analyte 112 in liquid sample 307. This property of semipermeable barrier 301 or wicking material 1501 may be used to increase the dynamic range of measurable concentrations of ion or molecule analytes 112 in a test sample. The binding capacity of semipermeable barrier 301 or wicking material 1501 can be determined using techniques described herein above for determining the binding capacity of porous conductive film 103. The concentration of an ion or molecule analyte 112 in a test sample may be determined using calibration curves that compensate for the amount of ions or molecules that bind to semipermeable barrier 301 or wicking material 1501 in a given embodiment of apparatus 100.

In some aspects, wicking material 1501 can be a lateral flow membrane that is made of nitrocellulose, acrylamide gel, porous glasses or ceramics, or composite mixtures comprising particles and binder so as to increase mechanical integrity of wicking material 1501, or may be made of any of numerous other materials useful for liquid wicking. In some aspects apparatus 100 may further comprise a wicking material or "pad" that has a high affinity for a test sample solution. Wicking material 1501 can be selected to cause the transport of ions or molecules across porous conductive film 103 and across one or more electrode pairs in sensor 110.

In some embodiments apparatus 100 can comprise a sensor having a plurality of electrode pairs 102 positioned at different locations along porous conductive film 103. In some aspects, a sensor response profile can be determined using one or ore of the plurality of electrode pairs 102. In some aspects, a plurality of sensor response profiles determined using a plurality of electrode pairs 102 may be used to determine the rate of diffusion of an ion or molecule analyte 112, or the amount or concentration of an ion or molecule analyte based on the binding capacity of $MO_x$ structures 104 for the ion or molecule analytes 112. Diffusion rates, analyte 112 identity, and analyte 112 quantity or concentration may be determined by analyzing sensor response data determined with the plurality of electrode pairs 102.

FIG. 15B illustrates an exemplary method for manufacturing sensor 110 configured in a lateral test strip format. In some embodiments, sensor 110 configured for use in a lateral test strip format and comprising porous conductive film 103 and electrode pair 102 on substrate 101 may be cut from a sheet 1504 which can be rolled onto spool 1505 during selected manufacturing process methods. In some embodiments, sheet 1504 can comprise substrate 101 that is a polymeric film. A polymeric film substrate 101 may be made of, by way of example only, polyethylene terephthalate, polystyrene, or polyimide. In some embodiments, exemplary useful methods for applying thin $MO_x$ structure 104 films to polymeric membrane substrate 101 include doctor blade, spin casting, and dip casting. Other useful methods will become apparent from this disclosure to a person having skill in the art. In some aspects, electrode pair 102 may be deposited onto porous conductive film 103 using for example vacuum deposition or electroless plating. In the exemplary embodiment schematically depicted in FIG. 15B, electrodes can be printed in a selected pattern using metal inks. In some aspects, printed electrodes can be sintered using methods such as pulsed light sintering or photonic sintering. In the embodiment depicted in FIG. 15B, porous conductive film 103 is present on substrate 101 and electrode pairs 102 are positioned on and operably connected to porous conductive film 103, for generating electric current in the film between the electrode pairs 102 and for detecting a change in an electrical property of the film.

In some embodiments, porous conductive film 103 may be applied to a substrate 101 made of a porous fiberglass matrix wherein porous conductive film 103 conformally coats the fiberglass matrix material that may be in the form of a fiberglass paper, mat, sheet, or roll and is configured to be operably connected to electrode pairs 102. Fiberglass paper, mat, sheet, or rolls are available commercially. The porosity of a fiberglass matrix material can be selected to allow submersion liquid 106 to flow into submerged porous conductive film 103 conformally coated onto the fiberglass matrix substrate 101. In some aspects, porous conductive film 103 may be applied to a substrate 101 made of flexible printed circuit board and can be configured to be operably connected to electrode pairs 102. In some aspects, sheet 1504 may comprise a bilayer sheet of a porous fiberglass support matrix and substrate 101 can comprise a flexible printed circuit board or printed and sintered electronics.

In some aspects, sensor 110 comprising a plurality of electrode pairs 102 positioned at different locations along porous conductive film 103, can be an array of sensors 110 or a sensor array. Sensors 110 in this embodiment of a sensor array comprise a pair of electrodes 102 operably connected to a region of porous conductive film 103 for generating electric current in the film region between electrodes of electrode pairs 102 and for detecting a change in an electrical property of porous conductive film 103 with the associated film region.

Figure 16A:
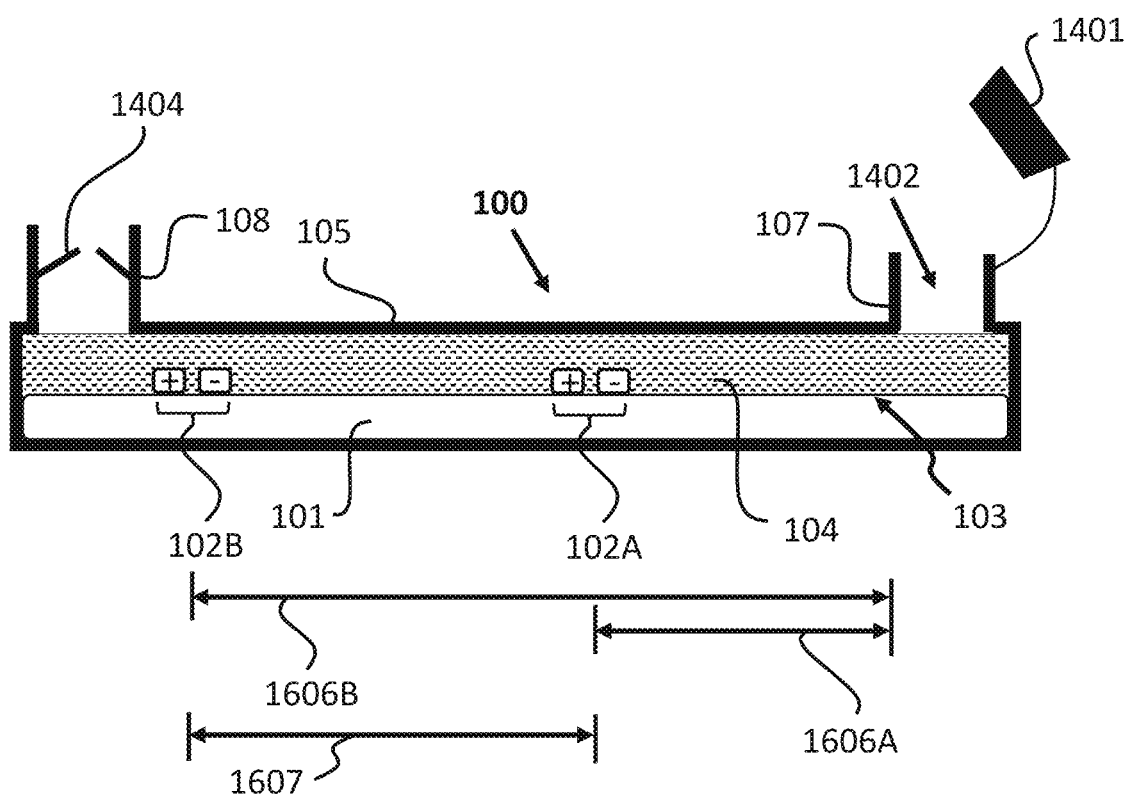
FIGS. 16A-16B illustrate a schematic depiction of an embodiment of an apparatus having two electrode pairs operably connected to a porous conductive film and configured for lateral sample flow and exemplary sensor response profiles that may be determined with a sensor comprising two electrode pairs.
Figure 16B:
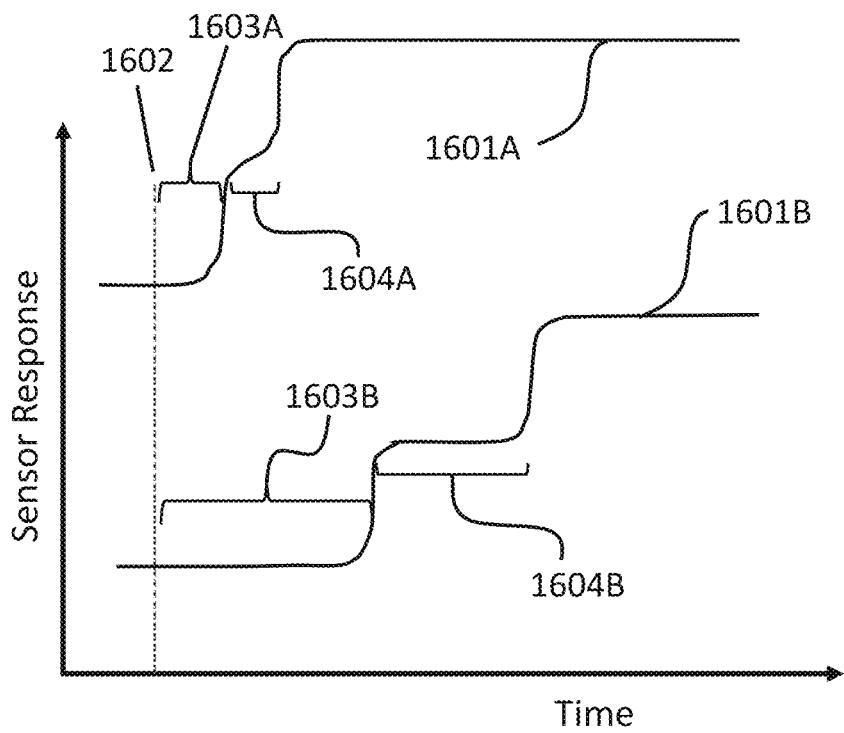

FIGS. 16A-16B illustrate a schematic depiction of an embodiment of an apparatus 100 having two electrode pairs 102 operably connected to a porous conductive film 103 and configured for lateral sample flow and for use in a lateral flow test strip format and exemplary sensor response profiles that may be determined with a sensor comprising two electrode pairs (102A, 102B). FIG. 16A illustrates a schematic depiction of an embodiment of an apparatus 100 having two pairs of electrodes operably connected to porous conductive film 103 and configured for lateral sample flow. In this embodiment, apparatus 100 comprises a sensor having two electrode pairs, including 102A positioned at distance 1606A from inlet port 107, and 102B positioned at distance 1606B from inlet port 107. Electrode pairs 102A and 102B are in contact with porous conductive film 103. As described above, an embodiment of apparatus 100 in which a plurality of electrode pairs 102 are configured in this manner with porous conductive film 103, corresponds to an embodiment comprising a plurality of sensors 110.

FIG. 16B illustrates exemplary sensor response profiles 1601A and 1601B which can be determined using electrode pairs 102A and 102B respectively, and the exemplary apparatus depicted in FIG. 16A. In this exemplary embodiment, sensor response data collection can begin at time point to represented by vertical line 1602. Test sample liquid added to reservoir 1402 can diffuse through porous conductive film 103 traversing electrode pairs 102A and 102B at different times following sample addition. Sensor response, determined with electrode pair 102A, to the interaction of a first species of ion or molecule with porous conductive film 103 initially increases after time period 1603A. Sensor response, determined with electrode pair 102B, to the interaction of the first species of ion or molecule with porous conductive film 103 initially increases after a longer period of time 1603B. Similarly, a second increase in sensor response, determined with electrode pair 102A, to a second species of molecule or ion in a test sample may occur after a second time period 1604A. Sensor response, determined with electrode pair 102B, to the interaction of the second species of ion or molecule with porous conductive film 103 may occur after a second, longer period of time 1604B. In some embodiments, such as the exemplary embodiment depicted here, sensor responses determined by electrode pairs 102A and 102B may be different based on differences in the diffusion rates of ion or molecule analytes 112 through porous conductive film 103 to outlet port 108.

In some embodiments the spacing 1607 between electrodes 102A and 102B can be chosen to provide sufficient time to determine differences in diffusion of solvated ions or molecules based on a change in the electrical property of porous conductive film 103. In other embodiments, the length of porous conducting film 103 can be increased to increase the total binding capacity along the length of porous conductive film 103. Increasing the length 1406 of porous conductive film 103 may increase the total mass of porous conductive film 103 and thereby increase the binding capacity. The number and spacing of electrode pairs 102 can be selected to increase the ability to measure a larger dynamic range of ions or molecules in a test sample, and may also provide higher resolution, or sensitivity of the concentration as measured by the change in an electrical property of porous conductive film 103. The width and height of housing 105 can also be designed for a specific mass of porous conductive film 103 per unit length and this property can be used to increase sensitivity and provide a lower limit of detection for ions or molecules in a test sample. In some embodiments, the distance between sample reservoir 1402 and the first electrode pair 102 in an array of sensors can be selected to have a specific time delay based on known diffusion times of ions or molecules in a test sample liquid.

Figure 17A:
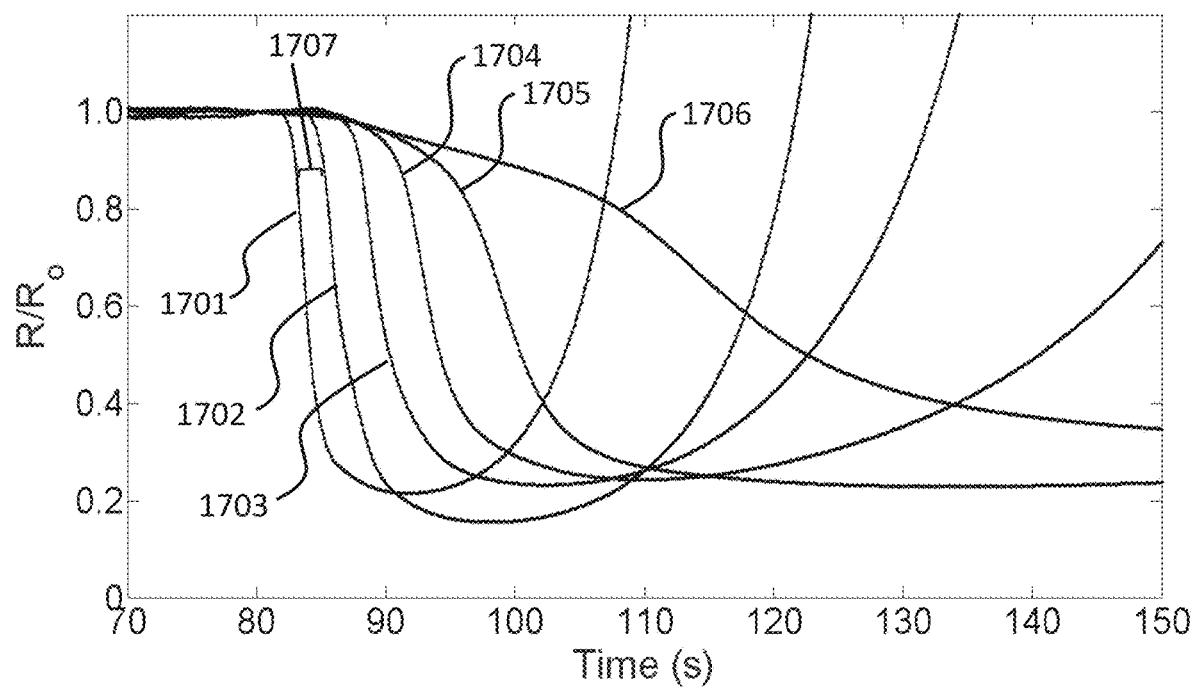
FIGS. 17A-17B illustrates six sensor response profiles determined with a liquid test sample of 10 mM $K_2HPO_4$, using an apparatus (FIG. 17B) having a sensor with six electrode pairs positioned at selected spaced-apart locations along a porous conductive film.
Figure 17B:
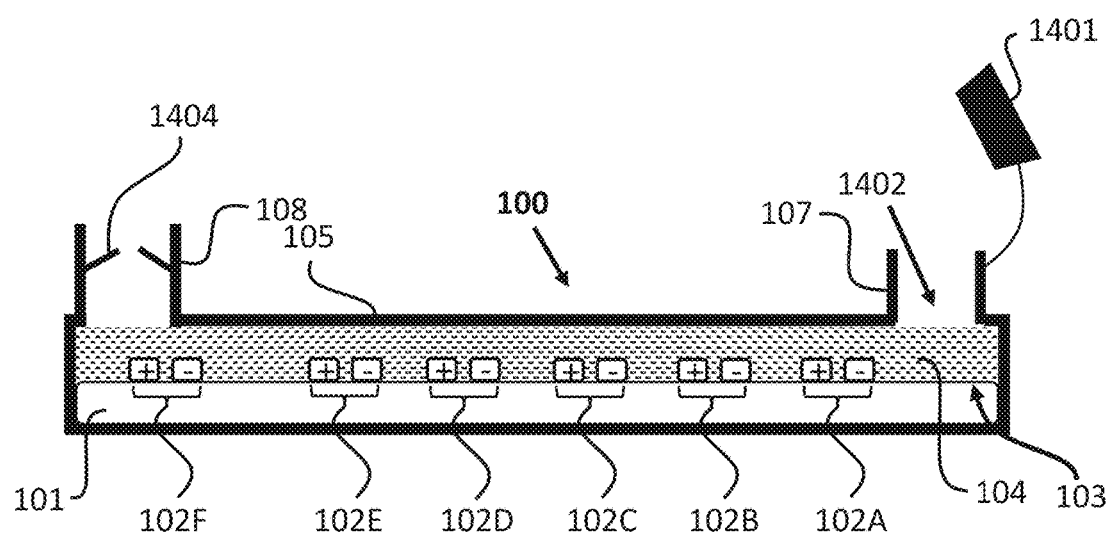

FIG. 17A shows six sensor response profiles determined with a liquid test sample of 10 mM $K_2HPO_4$, using an apparatus 100 (depicted schematically in FIG. 17B) having a sensor with six electrode pairs 102A-102F positioned at selected spaced-apart locations along porous conductive film 103. In this exemplary embodiment, normalized sensor response $R/R_0$ was plotted. Sensor response profile 1701 was determined using a first electrode pair 102A positioned closest to reservoir 1402 to which the test sample was added. Sensor response profile 1702 was determined using a second electrode pair 102B positioned downstream and next to electrode pair 102A with a distance of 1 mm between the sensors. Offset time 1707 represents the additional time required for the analyte from the test sample to diffuse to the second electrode pair 102B. Similar offset times were observed for each of the sensor response profiles determined with the remaining electrode pairs. Specifically, sensor response profile 1703 was determined with electrode pair 102C positioned 2 mm from electrode pair 102A, sensor response profile 1704 was determined with electrode pair 102D positioned 3 mm from electrode pair 102A, sensor response profile 1705 was determined with electrode pair 102E positioned 4 mm from electrode pair 102A, and sensor response profile 1706 was determined with electrode pair 102F positioned 6 mm from electrode pair 102A. In addition to the observed temporal offset 1707, the sensor response profiles determined by the different electrode pairs are different, which may possibly be due to changes in the local concentration of solvated ion or molecule analytes 112 during diffusion from sample reservoir 1402 to outlet port 108 and down porous conductive film 103 and as the solvated ion or molecule analytes 112 encounter available binding sites on the surface of different regions of porous conductive film 103, or which may possibly be due to one or more of the factors previously described herein that can affect sensor response to an analyte 112.

In some embodiments, porous conductive film 103 can be made or modified to cause differential diffusion rates of selected ions or molecules present in a liquid so as to enhance the separation, detection, and/or identification of the selected analyte. In some aspects, temporal and spatial separation of molecules and ions during diffusion to $MO_x$ structure surfaces 104 and interaction with the $MO_x$ structures 104 can enhance and improve the detection and identification of selected ion or molecule analytes 112. In some aspects, selected structural features of porous conductive film 103 can contribute to the differential diffusion of different molecules and ions to the surfaces of $MO_x$ structures 104 for detection and to regions of highest current density that may exist near substrate 101 between electrodes of electrode pair 102. Differential diffusion among ions and molecules throughout porous conductive film 103 can be used to enable and enhance the accuracy of detection, identification, and quantification of one or more selected ions or molecules in a liquid sample.

In some embodiments, a porous conductive film 103 may be made from $MO_x$ structures 104 of various selected sizes, shapes, and/or compositions. In some aspects, the thickness and/or porosity of porous conductive film 103 may be adjusted during the making process to affect the diffusion rates of selected molecules and ions. In some aspects, a sintering method and/or sintering parameters may be selected so as to make a porous conductive film 103 having suitable characteristics (e.g., $MO_x$ structure dimensions, porosity, thickness, extent of necking among structures, to name a few) effecting temporal and spatial separation during diffusion of selected ions and molecules.

In some embodiments, a porous conductive film 103 can comprise $MO_x$ structures 104 that are modified or "derivatized" with a diffusion matrix (i.e., conductive film 103 is a derivatized conductive film and the $MO_x$ structures 104 are derivatized structures). A diffusion matrix on $MO_x$ structures 104 can affect temporal and spatial separation of selected ions and molecules during diffusion to and through porous conductive film 103 and enhance the separation, detection, and/or identification of different ion or molecule analytes 112 in liquid sample 307. In some embodiments, a diffusion matrix can alter the rate at which an ion or molecule diffuses away from a porous conductive film 103 after interaction of an ion or molecule with $MO_x$ structure 104 in the film. In some aspects, different types of diffusion matrices may alter, in a different manner, the rate at which an ion or molecule diffuses to a $MO_x$ structure as compared to the rate at which a molecule or ion diffuses away from of a $MO_x$ structure.

In some aspects, a diffusion matrix can participate in a transient, non-specific chemical or electrostatic interaction with an ion or molecule in a liquid or with a plurality of different ion or molecule species in a liquid. Non-specific chemical interactions can be any of several different interactions that cause attraction or repulsion between a molecule in a diffusion matrix and an ion or molecule analyte 112. In some aspects, an electrostatic interaction can be attraction or repulsion between an electrically charged molecule or an ion present on a molecule in a diffusion matrix and an electrically charged ion or analyte. In some embodiments, ionic and molecular species, or specific compounds that are used to make a diffusion matrix are an ion or molecule that is being detected or quantified in a liquid sample. In some aspects, a chemical interaction can be a bonding interaction, such as a hydrogen-bond or dipole-dipole interaction between a molecule or an ion present on a molecule in a diffusion matrix and an ion or molecule analyte 112. In some aspects, a non-specific chemical interaction can be a hydrophilic or hydrophobic interaction such as, a polar or non-polar interaction between an ion or molecule present on a molecule in a diffusion matrix and an ion or molecule analyte 112.

In some aspects, a diffusion matrix can comprise a molecule, a molecular compound (covalent compound), a biomolecule, an ion, an ionic compound or mixtures thereof that are coupled to $MO_x$ structures 104. In other aspects, a diffusion matrix can comprise a molecule, a molecular compound (covalent compound), a biomolecule, an ion, an ionic compound or mixtures thereof that are chemisorbed or physisorbed to $MO_x$ structures 104. Different types of diffusion matrices can comprise different ions or molecules, different combinations of ions and molecules, and/or different amounts of ions or molecules.

In some embodiments, one or more sensors in an array can each comprise a porous conductive film 103 derivatized with the same selected type of diffusion matrix. In some embodiments a plurality of sensors in an array can each comprise a porous conductive film 103 derivatized with a diffusion matrix that is different from the diffusion matrix on other sensors 110. In some aspects, multiple sensors derivatized with the same type of diffusion matrix may be grouped together on a selected region of an array. In some embodiments, an array of sensors can comprise multiple groups of sensors, each group derivatized with a different, selected type of diffusion matrix.

In some embodiments, a sensor having a derivatized porous conductive film 103 can respond differently to an ion or molecule in a liquid sample, as compared to a sensor having an underivatized porous conductive film 103 (i.e., a film having no diffusion matrix) or as compared to a sensor having a conductive film that is derivatized with a different diffusion matrix. In some embodiments, diffusion matrix properties or the properties of molecules used for making a diffusion matrix can influence the rate of diffusion of an ion or molecule throughout the porous conductive film 103 and to the surfaces of $MO_x$ structures 104. Exemplary properties include molecular weight, size, and identity of ions, molecules, or compounds in a diffusion matrix. In some aspects, thickness or other structural characteristics of a diffusion matrix, such as porosity, may affect ion or molecule diffusion.

In some embodiments, a diffusion matrix can be present on or coupled to $MO_x$ structures in a conductive film or can be synthesized on an $MO_x$ structure such as for example only by using covalent coupling chemistry. Exemplary methods that can be used in some embodiments for coupling a diffusion matrix to $MO_x$ structures include synthesizing, spotting, drop-casting, or printing molecules on $MO_x$ structures. In some aspects, linkers may be used for attaching diffusion matrix components to $MO_x$ structure. Heterobifunctional linkers useful for covalent attachment of chemical and biological structures to surfaces are known and commercially available (e.g., from Sigma-Aldrich Co. LLC, St. Louis, Mo., USA). Exemplary linkers include silanes, glutaraldehydes, succinimides, carboxylates, epoxies and phosphonates to name a few.

In some embodiments, a diffusion matrix can comprise small molecules, ions, ionic compounds, polymers, or molecules that are biomolecules and may be referred to as a biomolecular diffusion matrix. In some embodiments, a biomolecular diffusion matrix can participate in a non-specific chemical or electrostatic interaction with an ion or molecule species in a liquid sample. The type of biomolecular diffusion matrix is determined by the biomolecule or biomolecules that make up the diffusion matrix. In some embodiments, different types of biomolecular diffusion matrices can comprise different biomolecules, different combinations of biomolecules, and/or different amounts of biomolecules.

As used herein, in some embodiments "biomolecule" and "biomolecular" can refer to a molecule that is produced or capable of being produced in or produced by a living organism. In some embodiments, a biomolecule for use in a diffusion matrix can be an organic molecule, a protein, peptide, polypeptide, oligopeptide, amino acid, polysaccharide, nucleic acid, DNA, RNA, small molecule, cytokine, hormone, lipid, antibody, sugar, acid, base, or other chemical or chemical compound. In some aspects, a biomolecule for use in a diffusion matrix can be a primary or secondary metabolite, aptamer, or receptor. In some aspects, a biomolecule can be an organic or inorganic breakdown product of a biomolecule.

In some embodiments, a biomolecule can be isolated from an organism or can be synthetically prepared in vitro. In some aspects, a biomolecule can be a fragment of a cell or a cell structure, such as for example a region of a cell membrane, a fragment of a cell membrane, a liposome, or a cellular organelle such as a mitochondrion, a nucleus, a Golgi apparatus, or another subcellular structure. In some embodiments, a biomolecule can be purified or partially purified during or following isolation from an organism. Methods for isolating and purifying biomolecules are known to those of skill in the art. It is also contemplated that novel purification methods not yet known in the art may be used for purifying a biomolecule for use in some embodiments. In some embodiments, in vitro synthesis of biomolecules can be used to make for example small molecules, antibodies, peptides, nucleic acids, cell membranes, membrane mimics, liposomes, and other biological structures.

In some embodiments, a biomolecular diffusion matrix can be synthesized in situ on $MO_x$ structures 104. In some aspects, a biomolecular diffusion matrix can comprise a peptide or a nucleic acid that can be synthesized in situ on $MO_x$ structures 104. Peptides synthesized on $MO_x$ structures may comprise, at least 2, 3, 4, 5, 6, 7, 8, 9, 10, 15, 20, 25, 30, 35, 40, 45, 50, 60, 70, 80, 90, or 100 amino acids or any number therebetween and inclusive of the smaller and larger sizes listed. In some aspects, peptide length may be any length that retains functionality as a biomolecular diffusion matrix and that can be synthesized on, or attached to, $MO_x$ structures. Nucleic acids synthesized on $MO_x$ structures may comprise, at least 2, 3, 4, 5, 6, 7, 8, 9, 10, 15, 20, 25, 30, 35, 40, 45, 50, 60, 70, 80, 90, or 100 nucleotides or any number therebetween and inclusive of the smaller and larger sizes listed. In other aspects, nucleic acid length may be any length that retains functionality as a biomolecular diffusion matrix and that can be synthesized on, or attached to, $MO_x$ structures. Representative methods for synthesizing peptides and nucleic acids on surfaces can be found in Gao et al., (Proteomics, (2003) 3:2135-2141), and Gao et al, (U.S. Pat. No. 6,426,184), both of which are incorporated by reference herein in their entirety. Other methods that may be used for synthesizing peptides and nucleic acids in some embodiments are known to those with skill in the art.

Computer modeling revealed that changes in the diffusion rates of ions or molecules in a liquid may occur in a predictable manner. A sensor response to ions and molecules can be affected by the diffusion rate according to Fick's law, the adsorption rate of ions or molecules onto the surfaces of $MO_x$ structures 104, the desorption rate of the ions or molecules from the surfaces of the structures, and the overall effect of the surface-adsorbed ions or molecules on the charge carrier concentration and mobility (i.e., electric current) in the $MO_x$ structures 104.

Figure 18A:
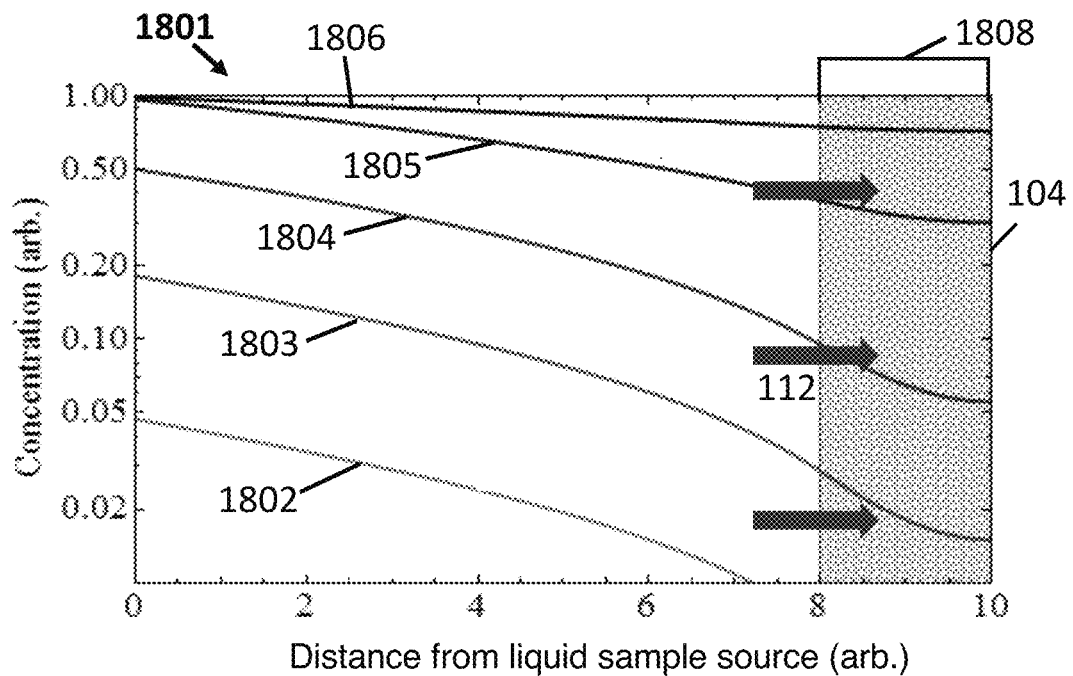
FIGS. 18A-18B illustrate concentration profile curves representing the concentration distribution of ion or molecule analytes between a liquid sample or wash liquid source and $MO_x$ structures derivatized with a diffusion matrix.
Figure 18B:
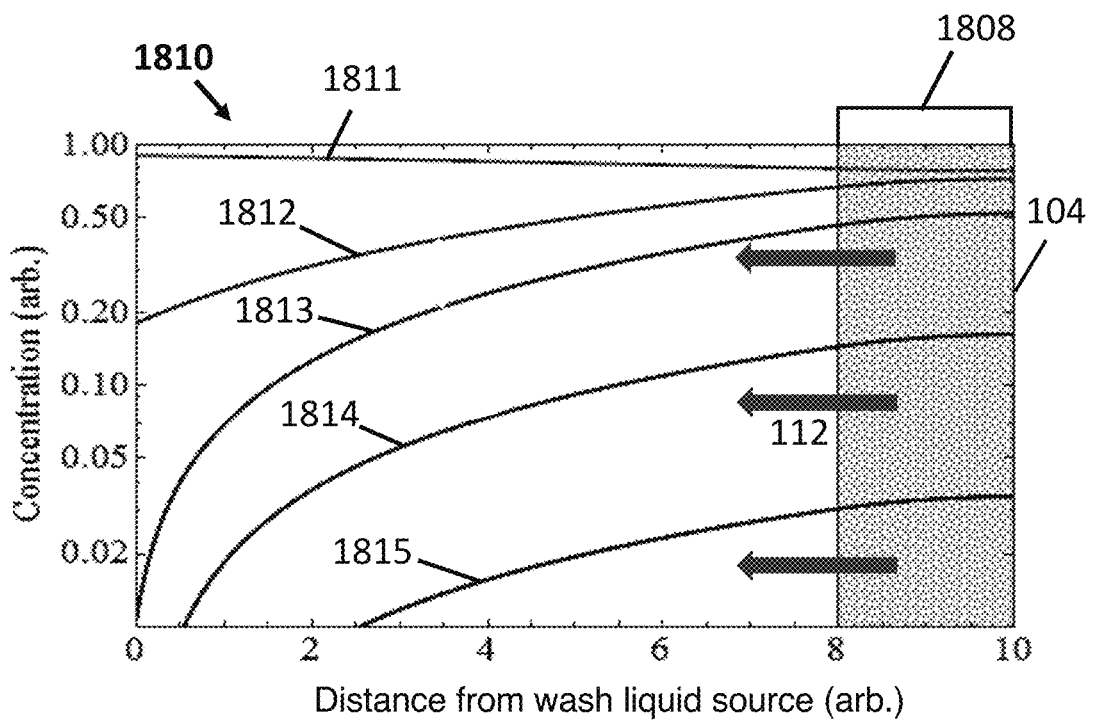

FIGS. 18A-18B illustrate concentration profile curves representing the concentration distribution of ion or molecule analytes 112 between a liquid sample or wash liquid source and $MO_x$ structures 104 derivatized with a diffusion matrix. FIG. 18A depicts analyte concentration distribution during liquid sample exposure and diffusion of ion or molecule analytes to the surfaces of $MO_x$ structures 104 in porous conductive film 103, and FIG. 18B depicts analyte concentration distribution after addition of wash liquid 111 and during diffusion of ion or molecule analytes 112 away from the surfaces of $MO_x$ structures 104 in a porous conductive film. In FIG. 18A and FIG. 18B, for ease of viewing, diffusion matrix 1808 is represented with shaded rectangles, and the direction of movement of ion or molecule analyte 112 is represented with horizontal arrows. Concentration is represented as the log concentration of the ion or molecule analyte in arbitrary units (arb.) (y-axis) as a function of the distance from liquid source in arbitrary units (x-axis).

FIG. 18A illustrates a one-dimensional concentration profile simulation 1801 for ion or molecule analyte 112, at different times during sample exposure and diffusion of ion or molecule analytes to $MO_x$ structures 104 on a selected region of a porous conductive film 103 at a fixed distance from a liquid sample source. In this example, $MO_x$ structures 104 are derivatized with diffusion matrix 1808. In FIG. 18A, each concentration profile curve (1802, 1803, 1804, 1805, 1806) represents the concentration of the ion or molecule analyte 112 at positions between the liquid sample source and the surfaces of $MO_x$ structures 104 at a specific time during liquid sample exposure when ion or molecule analyte 112 is diffusing through diffusion matrix 1808 and being adsorbed to binding sites on the surfaces of $MO_x$ structures 104. An exemplary, sample exposure duration may be 30 sec, and concentration profile curves 1802-1806 may represent ion concentration profiles determined at, for example, 1 sec, 5 sec, 10 sec, 15 sec, and 30 sec, respectively, following initiation of test sample liquid exposure. Ion or molecule analyte 112 concentration at the surfaces of $MO_x$ structures 104 increases with increasing time of exposure to a liquid sample containing the ion or molecule analyte, e.g., curve 1806 representing the longest time after initiation of liquid sample exposure. The simulation is primarily based on Fick's diffusion law, treating the diffusion matrix 1808 with a diffusion coefficient distinct from the region between the outermost surface of diffusion matrix 1808 on $MO_x$ structures 104 and the liquid sample source (at position 0 on the x-axis). The simulation takes into account diffusion parameters and the adsorption and desorption rates of the ion or molecule analyte on the surfaces of $MO_x$ structures 104.

FIG. 18B illustrates a one-dimensional concentration profile simulation 1810 for ion or molecule analyte 112, at specific times after exposure to a wash liquid 111, expressed as the log concentration of the ion or molecule analyte 112 in arbitrary units (arb.) (y-axis) as a function of the distance from wash liquid (x-axis). In this period, the wash liquid 111 does not contain ion or molecule analyte 112. As such, some ion or molecule analytes 112 desorb from the surfaces of $MO_x$ structures 104 and diffuse away into the wash liquid through diffusion matrix 1808. The concentration profile curves (1811, 1812, 1813, 1814, 1815) represent ion or molecule concentrations at progressively longer times, at positions between the wash liquid source and the outermost surface of diffusion matrix 1808, during wash liquid exposure and during dwell period 509. Ion or molecule concentration at the surfaces of $MO_x$ structures 104 is highest at the shortest time point after introduction of wash liquid, represented by curve 1811 and is lowest at the longest time point after exposure to wash liquid, represented by curve 1815.

Figure 19:
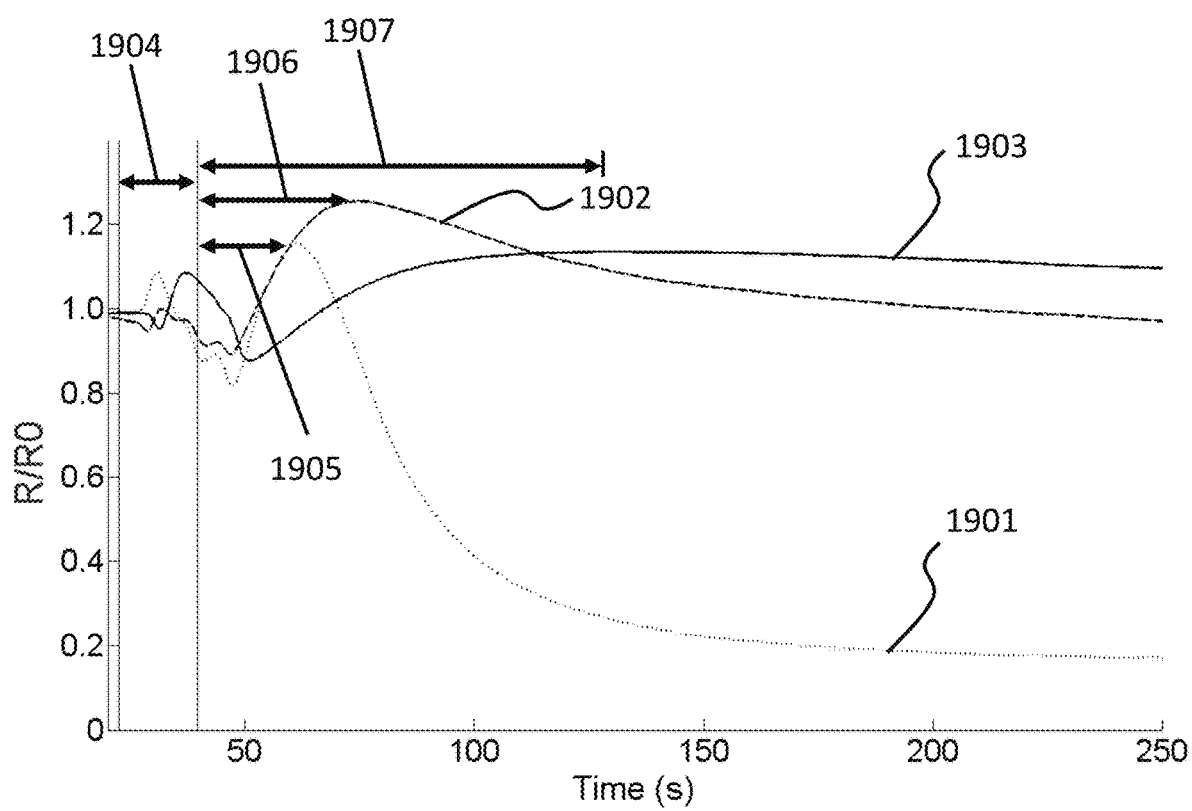
FIG. 19 illustrates sensor response profiles, normalized and offset in time to create an overlay view, that were determined using the same sensor having a porous conductive film comprising three different diffusion matrices for a test sample comprising 10 mM NaCl.

FIG. 19 illustrates sensor response profiles 1901-1903, normalized and offset in time to create the overlay view, that were determined using the same sensor having a porous conductive film comprising three different diffusion matrices for a test sample comprising 10 mM NaCl. Sensor response profile 1901 was determined using a sensor having an underivatized porous conductive film 103. The same sensor was used to determine sensor response profile 1902 after a goat anti-rabbit antibody was coupled as a diffusion matrix to $MO_x$ structures 104. An additional response profile 1903 was determined with the same sensor 110 after further binding a rabbit anti-goat IgG to the anti-rabbit antibody previously bound to $MO_x$ structures 104. Derivatization of porous conductive film 103 with biomolecules imparted a clear distinction between the sensor response profiles determined for the same analyte, NaCl. In addition to the sensor profile shape differences which began as early as the liquid test sample addition period 1904, the time delay imparted by the different biomolecular diffusion matrices can be seen. The shortest time delay 1905 occurs for the underivatized sensor. The coupling of goat anti-rabbit antibody results in longer time delay 1906, presumably due to the longer time needed for the analyte 112 to diffuse through the diffusion matrix comprising goat anti-rabbit antibody. Time delay 1907 further represents the extended period needed for analyte to diffuse through diffusion matrix 1808 comprising rabbit anti-goat antibody bound to goat anti-rabbit antibody on $MO_x$ structures 104. Derivatization methods may be used to make porous conductive film 103 that can be used to differentiate ions or molecules based on the differences in diffusion time through a diffusion matrix.

Figure 20A:
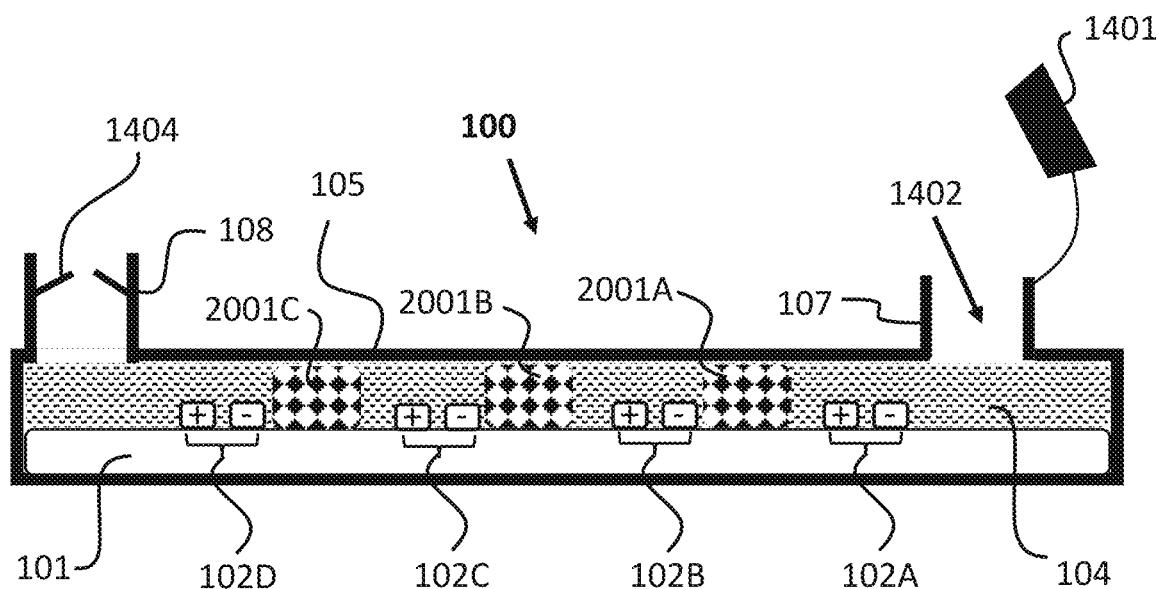
FIGS. 20A-20B illustrate an embodiment of an apparatus configured for lateral sample flow and having a plurality of spaced apart electrode pairs and regions of a porous conductive film derivatized with diffusion matrices.
Figure 20B:
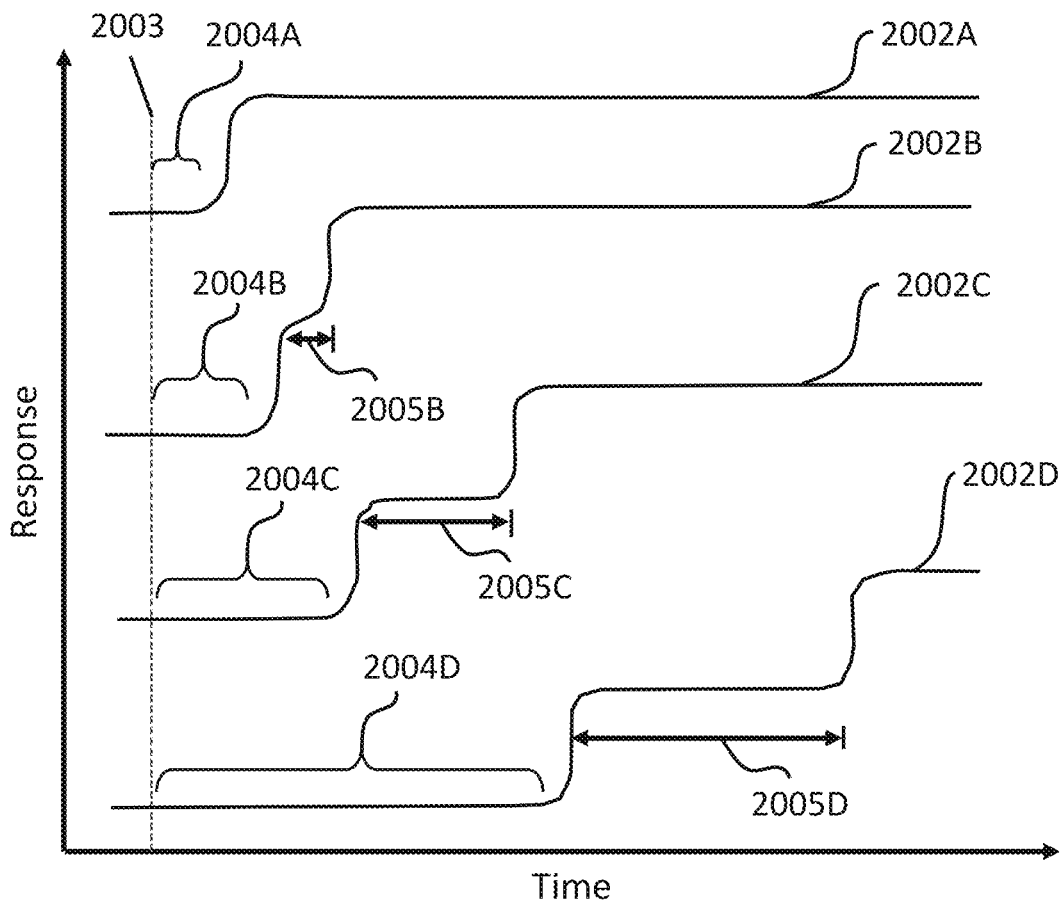

FIGS. 20A-20B illustrate an embodiment of an apparatus configured for lateral sample flow and having a plurality of electrode pairs 102 and regions of a porous conductive film 103 derivatized with diffusion matrices 2001A-2001C. FIG. 20A illustrates an embodiment of apparatus 100 configured for lateral sample flow. In this exemplary embodiment porous conductive film 103 is derivatized with diffusion matrices at selected regions between electrode pairs 102A and 102B, matrix 2001A; between electrode pairs 102B and 102C, matrix 2001B; and between electrode pairs 102C and 102D, matrix 2001C.

FIG. 20B illustrates four sensor response profiles that may be determined using different electrode pairs 102 in the apparatus embodiment depicted in FIG. 20A. Sensor response profiles 2002A-D can be determined with electrode pairs 102A-D, respectively. In this exemplary embodiment, measurements of an electrical property of porous conductive film 103 can begin at time point to represented by vertical line 2003. In this embodiment, solvated ions and molecules in test sample liquid diffusing from sample reservoir 1402 through the interstitial liquid in porous conductive film 103 toward outlet port 108 may traverse electrode pairs 102A-D at different times, and an initial response of each sensor to an ion or molecule analyte 112 may occur at different times, illustrated as the amount of time spanning regions 2004A-D, respectively. In embodiments, in which a liquid test sample comprises a plurality of species of ion or molecule analytes 112 that can diffuse at different rates through porous conductive film 103, subsequent changes in sensor response measured by the different electrode pairs 102 may begin at different times. In this exemplary embodiment, liquid test sample is added to sample reservoir 1402 nearest to electrode pair 102A. In this embodiment, the plurality of different species of analytes 112 may not separate prior to sample diffusion to electrode pair 102A. As such a plurality of sensor responses indicative of different analytes may not be observed. In some embodiments, as solvated ion and molecule analytes 112 in submersion liquid 106 diffuse further toward outlet port 108, the amount of time that passes between a first response to a first analyte 112 and a second response to a second analyte 112 (times 2005B, 2005C, and 2005D) may become increasingly longer. However, in some embodiments diffusion matrices 2001A, 20018, and 2001C on $MO_x$ structures 104 may inhibit diffusion of one or more analytes in a test sample liquid. As such, in these embodiments the amount of time that passes between a first response to a first analyte and a second response to a second analyte at each electrode pair 102 can depend on interactions that may occur between each analyte in a sample and diffusion matrices 2001A-2001C.

Figure 21:
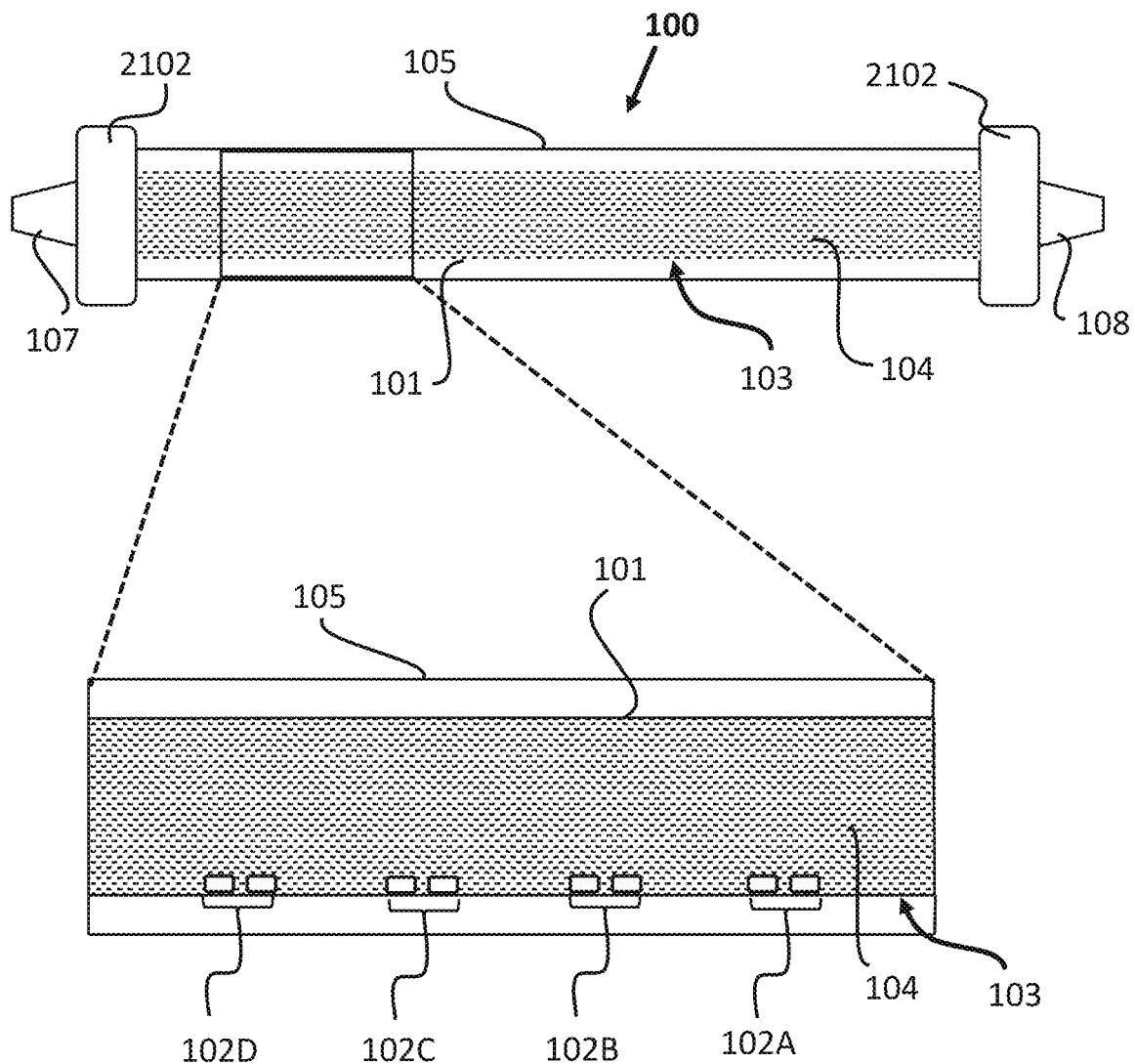
FIG. 21 illustrates an embodiment of an apparatus in which $MO_x$ structures are deposited to fill a housing and an enlargement of a region of the apparatus.

FIG. 21 illustrates a schematic depiction of an embodiment of apparatus 100 in which $MO_x$ structures 104 are deposited to fill a housing and an enlargement of a region of the apparatus. In some embodiments, $MO_x$ structures 104 may be deposited within housing 105. In some embodiments, $MO_x$ structures can be deposited to fill a portion of the volume of housing 105 in which the portion is greater than 0% and from less than about <1% to 100% of the available volume of housing 105. In some embodiments $MO_x$ structures may fill about 2%, 5%, 10%, 25%, 50%, 95%, 99%, or about 100% of the volume of housing 105. In some aspects, an exemplary housing 105 useful in these embodiments can be a pipe or tube with a circular or square cross section. In some embodiments the cross-sectional geometry of housing 105 may be any geometrical shape suitable for use in apparatus 100. In some aspects, examples of these geometrical shapes may include an elliptical or rectangular cross section. In the exemplary apparatus depicted in FIG. 21, $MO_x$ structures 104 form porous conductive film 103 that fills housing 105 and is positioned on substrate 101 that is the interior surface of housing 105. In some aspects, porous conductive film 103 that fills housing 105 may be held in position using for example a porous grate 2102, which can be positioned adjacent to inlet port 107 and outlet port 108 to prevent $MO_x$ structures 104 from exiting housing 105, while allowing liquid to pass during analysis of liquid samples. In these exemplary embodiments, a plurality of electrode pairs 102A-D can be operably positioned along an interior sidewall of housing 105 to measure an electrical property of porous conductive film 103.

Figure 22A:
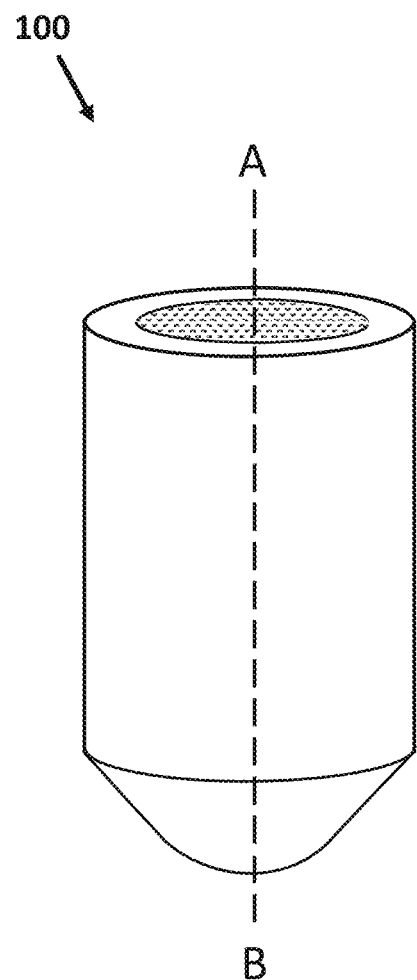
FIGS. 22A-22B illustrate a perspective view and a cross section of an embodiment of an apparatus in which $MO_x$ structures are deposited to fill a housing, and which is adapted for use in a vertical or gravity sample flow position.
Figure 22B:
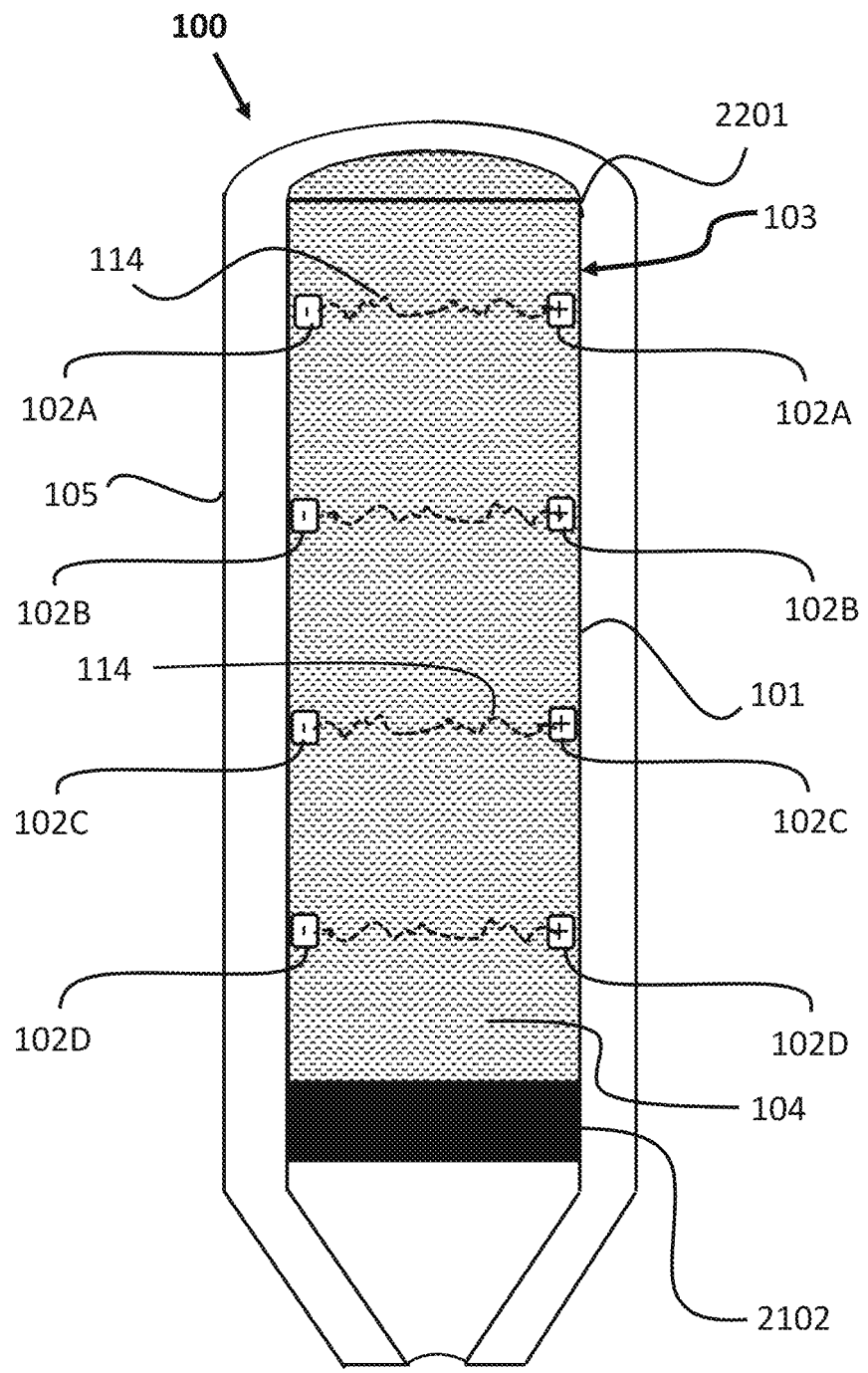

FIGS. 22A-22B illustrate a perspective view and a cross section of an embodiment of an apparatus 100 in which $MO_x$ structures 104 are deposited to fill housing 105, and which is adapted for use in a vertical or gravity sample flow position. FIG. 22A is a perspective view of this exemplary embodiment of apparatus 100. FIG. 22B is an AB cross-sectional view of FIG. 22A. In this exemplary embodiment, $MO_x$ structures 104 can be deposited in vertical housing 105 to a selected level 2201 and can be held in place by porous grate 2102, thereby forming porous conductive film 103 on substrate 101 that is the interior surface of housing 105. In some embodiments, a liquid test sample can be added to the top of porous conductive film 103 comprising $MO_x$ structures 104 and sample liquid can traverse the column from top to bottom. In some embodiments, a single electrode pair 102 or a plurality of electrode pairs 102A-102D can be operably positioned with each electrode adjacent to one another along an interior sidewall of housing 105 (as in the configuration of electrode pairs 102A-102D in FIG. 21) to measure an electrical property of porous conductive film 103. In some aspects, each electrode in an electrode pair 102 can be positioned such that they are not adjacent. For example, electrodes in an electrode pair 102 may be separated and operably positioned across from each other in housing 105 as illustrated in the FIG. 22. Current 114 between each electrode in a pair may be determined by the shortest distance between each electrode and may comprise current that follows multiple paths through porous conductive film 103. In some aspects, spacing 1607 between electrode pairs 102 may be chosen to drive current 114 between selected electrode pairs.

In some embodiments, detecting, identifying, and/or quantifying an ion or molecule analyte 112 in a test sample can comprise comparing test sample sensor response data with control sensor response data acquired with one or more control liquid samples having one or more known ions or molecules. In some embodiments, a control sensor response profile can be determined with a control liquid sample having a known concentration of an analyte 112 of interest. In some embodiments, the one or more known ion or molecule analytes 112 can be one or more selected ion or molecule analytes 112 suspected of being in a test sample. In some aspects, detecting a plurality of selected analyte species 112 in a test sample can comprise comparing one or more test sample sensor response profiles with one or more control sensor response profiles.

In some embodiments, a plurality of sensor response profiles determined with control and test samples, under a variety of experimental conditions using a variety of sensors 110, can be compared for detecting one or more selected species of ion or molecule analytes 112. Exemplary experimental parameters that may be varied when determining a sensor response profile have been extensively listed and described herein. In some embodiments, exemplary experimental parameters that can be varied when determining sensor response data include, sensor structure, presence and type of a diffusion matrix, concentrations of ions or molecules in a liquid sample, presence and type of a semipermeable barrier 301, composition of liquid in which a sensor 110 is submerged, ion or molecule species and number of different species in a control liquid sample, to name several.

In some aspects analyzing a liquid sample can comprise (1) exposing a sensor 110 to the liquid sample by adding the liquid sample to a chamber 109, the chamber having a submersion liquid 106 disposed therein and the sensor submerged in the submersion liquid 106, wherein the sensor comprises a porous conductive film 103 made of chemiresistive semiconducting $MO_x$ structures 104; (2) generating an electric current in the porous conductive film 103 and measuring an electrical property of the porous conductive film 103 for a selected period of time ranging from before exposing the sensor to liquid sample 307 to a selected time after exposing the sensor 110 to the liquid sample; (3) identifying a change in the measured electrical property of the porous conductive film 103; and (4) correlating the change in the measured electrical property with the presence of an ion or molecule analyte 112 in the liquid sample. In some aspects, exposure of sensor 110 to liquid sample 307 can be stopped, for example by washing sensor 110 with a wash liquid 111 and measuring an electrical property of porous conductive film 103 can continue for a selected time after exposure to liquid sample 307 is stopped and may continue for a selected time during and after wash period 508. In some aspects, comparing liquid test sample sensor response data with control sensor response data can be used to correlate a change in the measured electrical property of a porous conductive film 103 with the presence of an ion or molecule analyte 112 in the liquid sample. As used herein in some embodiments, a measured electrical property of a porous conductive film 103 also means determining sensor response data or sensor response. In some aspects, measuring an electrical property of the porous conductive film 103 may be for a selected period of time ranging from before exposing the sensor 110 to the liquid sample to a selected time after stopping exposure of the sensor 110 to the liquid sample.

In some embodiments, qualitative and quantitative differences and similarities between a control sensor response profile and a test sample sensor response profile and among multiple sensor response profiles can be determined by computationally comparing sensor response data obtained during analysis of control and/or test samples. Sensor electrical response data may be transferred to a processor and in some aspects stored in a database and deconvoluted or processed to determine the presence or absence of and/or the quantity of a selected type of ion or molecule analyte 112 in a liquid sample. In some aspects, comparing sensor response data determined with control and test samples can comprise comparing data that are stored in the database.

In various embodiments, an apparatus is disclosed for use in the detection, identification, and quantification of one or more selected species of ions and/or molecules. In some embodiments, the apparatus can comprise or be communicatively coupled to a processor that is communicatively coupled to a memory device. In some embodiments, machine-executable instructions can be stored on an apparatus in a non-transitory computer-readable medium (e.g., machine-executable instructions, algorithms, software, computer code, computer programs, etc.) When executed by the processor, instructions can cause the processor to receive sensor response data and to conduct analyses of sensor response data. In some aspects, the machine-executable instructions can cause the processor to (a) receive an input of sensor response data; (b) generate a sensor response profile comprising an association of an electrical response of a sensor with time of exposure of the sensor to one or more liquid samples; and (c) store the data on the memory device or on any other memory device that is communicatively coupled to the processor. In some aspects the machine-executable instructions can cause the processor to (a) compare sensor response profile data acquired from a plurality of sensor response determinations performed during analyses of control and test liquid samples; (b) identify qualitative and quantitative differences among selected sensor response profile data; (c) deconvolute the sensor response profile data to identify and quantify individual species of ions or molecules that may be present in a liquid sample; (d) correlate a change in a measured electrical property of a porous conductive film with the presence of a species of molecule or ion in the liquid sample and/or (e) store the data on the memory device or on any other memory device that is communicatively coupled to the processor. In some embodiments, the apparatus is a computer, wherein the computer comprises a processor and a memory device having computer code stored on it.

In some embodiments, the apparatus can further comprise a monitor communicatively coupled to the processor and memory device to display input information and/or the sensor response profile. In some embodiments, instructions stored on the non-transitory machine-readable medium further encode a user interface that provides a graphical display on a monitor. In some embodiments, the interface can allow a user to enter parameter information regarding sensor response data (e.g., by allowing the user to upload a data file or by allowing the user to enter information into display fields shown on the user interface). In some embodiments, the user interface provides the user with options for analyzing the parameter information, such as various methods for displaying and/or saving the input data and/or sensor response profiles (e.g., by displaying the data on the user's monitor, sending the data to a specified electronic device or electronic address, printing, and/or saving the data to a particular location). In various embodiments, a sensor response profile can be stored as data in a non-transitory storage medium physically connected to the apparatus (e.g., on an internal memory device such as a hard drive on a computer) and/or stored on a remote storage device that is communicatively connected to the apparatus (e.g., by a wired or wireless intranet or internet connection and the like). In some embodiments, the user interface provides the user with options for automatically storing the sensor response data in a particular location, printing the data, and/or sending the data to a specified electronic device or electronic address. In some aspects of the invention, including for display purposes, measured current values in sensor response data can be converted to resistance through Ohm's law (V=IR) and reported as a sensor response profile or a graphical display of a sensor response profile.

In some embodiments, the identity of one or more ion or molecule analytes 112 that are to be detected and/or quantified in a liquid sample may be known. In some aspects, monitoring the progress of a chemical reaction in a liquid can be accomplished by measuring an electrical response of porous conductive film 103 in the presence of the chemical reaction for a selected period of time, identifying a change in the measured electrical property of the porous conductive film, and correlating the change in the measured electrical property with the presence of a selected species of ion or molecule in the liquid sample or a plurality of selected species of ions or molecules molecule or ion in the liquid sample.

Figure 23:
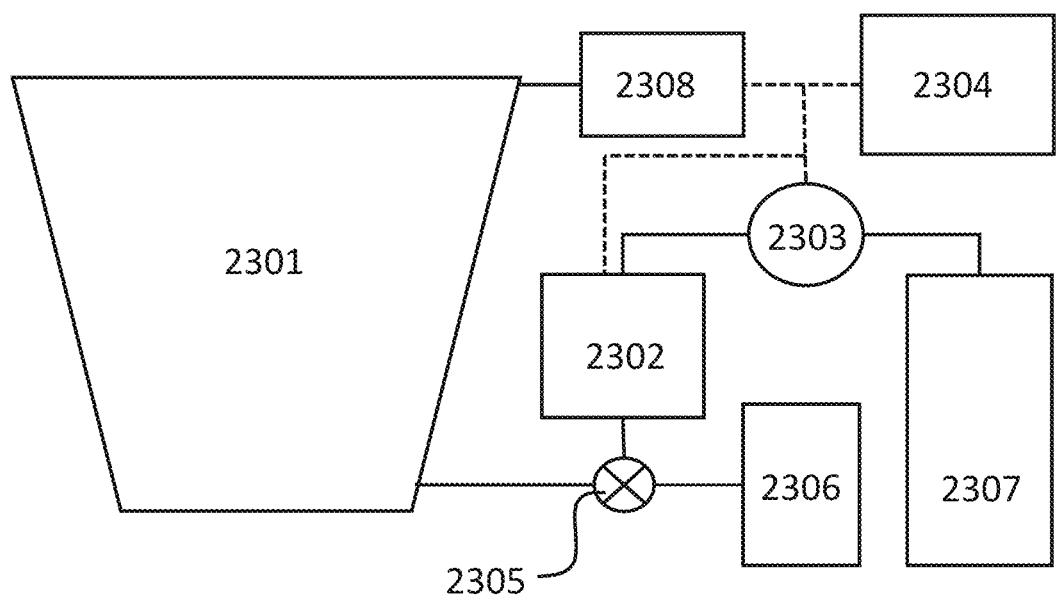
FIG. 23 illustrates an embodiment of a reactor or bioreactor and associated components useful for monitoring progress of a chemical reaction.

FIG. 23 illustrates an embodiment of a reactor or bioreactor and associated components useful for monitoring progress of a chemical reaction. In this exemplary embodiment, bioreactor 2301 may be used for housing a chemical reaction mixture such as, for example only, a reaction for the production of a selected biomolecule. In some embodiments, a liquid sample of a reaction mixture can be directed to sensor detection region 2302 using pump 2303. In some embodiments sensor detection region 2302 can comprise an apparatus 100 useful for detecting ions and molecules. Apparatus 100 may be used to determine sensor response profiles for detecting and/or quantifying analytes 112 in the liquid sample. Sensor response data may be analyzed by using computational analysis system 2304. In some aspects, monitoring production of a known analyte is accomplished by determining and comparing sensor response data from liquid test samples pumped from bioreactor 2301 to sensor detection region 2302. Pump 2303 working in concert with valve 2305 can provide a means for moving liquid test samples, and for moving wash liquid from wash reservoir 2306 for washing the sensor in apparatus 100 as needed. After determining sensor response data for test liquid sample and wash liquid samples, pump 2303 may direct spent liquid to waste reservoir 2307. Computational analysis system 2304 may be used to analyze sensor response data. In some embodiments, computational analysis system can be programmed to cause the movement of one or more reaction components, chemicals, diluents, buffers, stabilizers, or other reagents to bioreactor 2301 from reagent reservoir 2308.

In some embodiments, an apparatus can be useful for monitoring a chemical reaction for ions and molecules that are produced during the reaction. One exemplary chemical reaction that can be monitored using apparatus 100 is the extension of a nucleic acid molecule, such as by way of example only, a nucleic acid polymerization that occurs during sequencing of a nucleic acid. Nucleic acid polymerization and sequencing reactions including reaction components and by-products have been extensively studied. DNA polymerization and DNA sequencing are described here as one example.

DNA sequencing detects the incorporation of deoxyribonucleoside triphosphates (dNTPs) as nucleotides into a growing strand of the nucleic acid, thereby enabling a determination of the DNA sequence of the growing strand of DNA. Components of a typical sequencing reaction are well known to persons of skill in the art. Exemplary reaction components include a template DNA strand, a sequencing primer, one or more dNTPs, a polymerase reaction buffer having a pH suitable for enzyme functionality, a source of $Mg^{2+}$ ions (e.g., $MgCl_2$), and a polymerase enzyme. During a polymerization reaction, a sequencing primer hybridizes with a complementary region of a DNA template strand. A dNTP present in the reaction mixture is added by a polymerase enzyme to the 3' end of the primer across from a complementary nucleotide base present in the template strand. The identification of the added nucleotide at each location in a growing DNA strand can be monitored as the DNA strand grows, allowing for determination of the DNA sequence. During addition of a dNTP to the 3' end of a growing DNA strand, a proton $H^+$ is released from the 3'-OH present in the nucleotide at the 3' end of the primer, and two phosphate groups (PPi) complexed with $Mg^{2+}$ are released from the added dNTP. Free $Mg^{2+}$, counter ion (e.g., $Cl^-$), and buffer molecules are also present in the mixture. In one exemplary embodiment for DNA sequencing, a sequencing reaction may progress in submersion liquid 106 which can be chosen to comprise reaction components necessary for nucleic acid synthesis. In some aspects, a liquid reaction may initially comprise necessary reaction components but lack dNTPs. In these exemplary aspects, a selected dNTP may be added singularly to the liquid polymerase reaction mixture and conductance or resistance of porous conductive film 103 can be measured to determine if the dNTP was incorporated into the growing DNA strand. In some embodiments, the associated $H^+$ release can result in a change in the pH of the reaction liquid 106, and the pH change can be detected by measuring a change in conductance or resistance of porous conductive film 103 as $H^+$ ions bind to or interact with $MO_x$ structures 104. In some embodiments, one or more other molecules or ions that are produced as the result of nucleotide incorporation during nucleic acid chain extension or that are indicative of incorporation of a nucleotide into a nucleic acid molecule can be detected and/or quantified by identifying a change in a measured electrical property of porous conductive film 103 and correlating the change in the measured electrical property with the presence or amount of the one or more ion or molecule analytes 112. In some aspects, it can be useful to evaluate sensor response data to identify and/or quantify multiple ions or molecules whose presence or amount is indicative of incorporation of a nucleotide into a nucleic acid molecule. In some aspects, the addition of a dNTP to a polymerase reaction may result in no detectable change in an electrical property of porous conductive film 103, and in some aspects, this can suggest that the selected dNTP is not complementary to the appropriate nucleotide present in the template strand and was not incorporated into a growing nucleic acid. Selected dNTPs may be added individually to a reaction mixture in a suitable fashion to enable detection of the incorporation of dNTPs and determination of the DNA sequence of the template and newly synthesized strands.

In some embodiments, determining a sensor response during a chemical reaction, such as nucleic acid synthesis, can be at a temperature or in a temperature range that is suitable for reaction progress, enzyme functionality, and reagent stability, to name a few parameters.

In some embodiments, selected control liquid mixtures of a polymerization reaction, lacking for example selected components of the reaction mixture, may also be exposed to a sensor 110 and the sensor responses compared with sensor responses for other selected control mixtures or with complete reaction mixtures to assist in determining the DNA sequence. In some embodiments, a sensor response to ions and molecules in a DNA sequencing reaction can be compared to a sensor response observed during exposure of sensor 110 to a reaction mixture that lacks all dNTPs or to a reaction mixture that comprises one or a plurality of selected dNTPs. Computer-implemented deconvolution of sensor response data allows for determination of dNTP incorporation, or lack thereof, in a growing DNA strand.

In some embodiments, reaction products or by-products released during nucleotide incorporation may diffuse at different rates through the interstitial liquid among $MO_x$ structures of porous conductive film 103. For example, smaller $H^+$ ions may diffuse more rapidly than $Mg^{2+}$, PPI—$Mg^{2+}$, $Cl^-$, and other larger ion or molecule analytes 112 to $MO_x$ structure 104 of porous conductive film 103, thereby allowing, by way of example only for more sensitive, more rapid, or more selective determination of proton release and nucleotide incorporation.

In some embodiments, a dual chamber housing may be employed when monitoring a chemical reaction. For example, for monitoring DNA sequencing, reaction components may be added to second subchamber 302 that is separated from first subchamber 303, by semipermeable barrier 301. Semipermeable barrier 301 can be chosen so as to allow for diffusion of selected smaller ion or molecule analytes 112 from the polymerization reaction progressing in subchamber 302, across semipermeable barrier 301, and to subchamber 303 for detection by sensor 110. In some aspects, detection and quantification of these selected ion or molecule analytes 112 that may be produced during DNA polymerization can be correlated with the incorporation of a nucleotide into a nucleic acid molecule and used for determining a DNA sequence or for detecting and quantifying nucleic acid molecules.

In some embodiments an apparatus can be useful for detecting ions or molecules in a polymerization reaction such as for example a nucleic acid polymerization. In some aspects, detecting ions or molecules in a nucleic acid polymerization reaction can be used for determining a nucleic acid sequence or for quantifying nucleic acids, such as amplified nucleic acids from a nucleic acid amplification reaction. In some aspects a method comprises exposing a sensor to a liquid reaction mixture for polymerization of nucleic acids, wherein the sensor is disposed in a chamber and submerged in submersion liquid 106 and wherein the sensor comprises a porous conductive film 103 made of chemiresistive semiconducting $MO_x$ structures 104; generating an electric current in the porous conductive film 103 and measuring an electrical property of the porous conductive film 103 for a selected period of time; identifying a change in the measured electrical property of the porous conductive film 103; and correlating the change in the measured electrical property with the incorporation of a nucleotide into a nucleic acid molecule. In some aspects, the nucleic acids can be quantified.

In some embodiments, it may be useful to modify or adjust the structural characteristics of porous conductive film 103 so as to modify diffusion of different molecules or ions throughout porous conductive film 103 during monitoring of an electrical property of the film, such as during the monitoring of a chemical reaction. In some aspects, it may be suitable that porous conductive film 103 comprises $MO_x$ structures 104 derivatized with molecules that interact nonspecifically with ion or molecule reaction components, products, or by products, thereby modifying the diffusion of one or more ion or molecule species to the surfaces of $MO_x$ structure 104.

In some aspects, selected reaction components of a chemical reaction can be attached to or coupled to $MO_x$ structures 104 in porous conductive film 103. By way of example only, a DNA template that is being sequenced can be attached to $MO_x$ structures 104 or a DNA template that is being amplified may be attached to $MO_x$ structures 104. In some embodiments, nucleotide primers used in sequencing or amplification reactions may be attached to $MO_x$ structures 104. In some embodiments, reagents may be synthesized or modified such that newly synthesized or amplified nucleic acids can be attached to $MO_x$ structures as a reaction progresses.

Figure 24A:
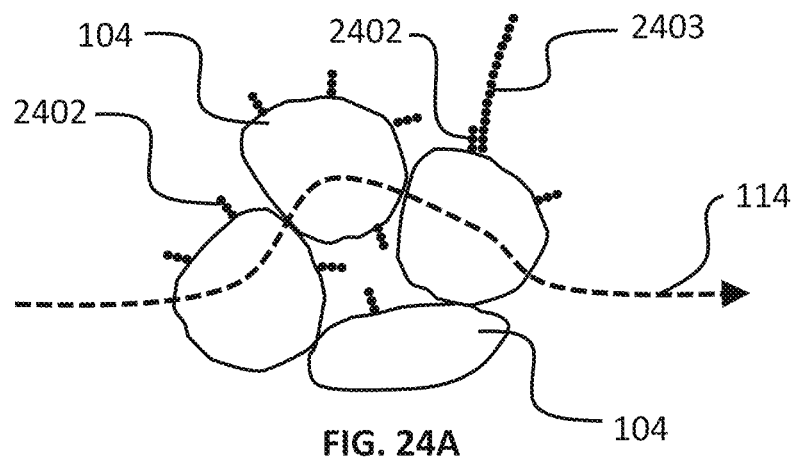
FIGS. 24A-24C illustrate an exemplary embodiment in which target DNA is captured on $MO_x$ structures and amplified.
Figure 24B:
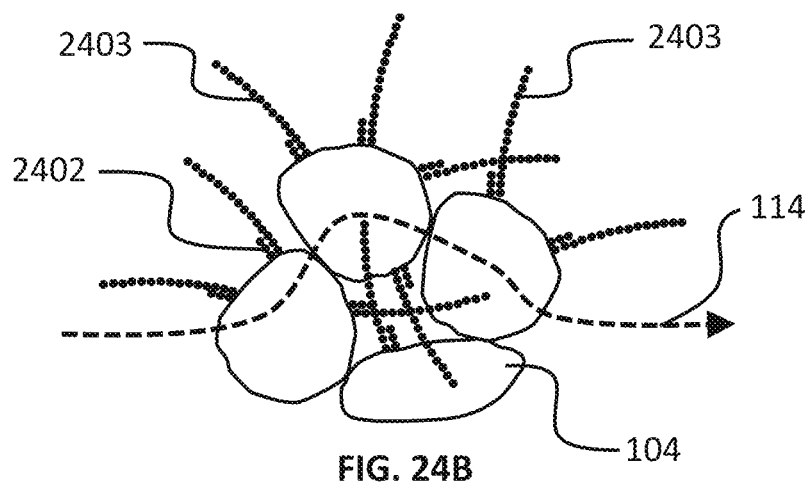
Figure 24C:
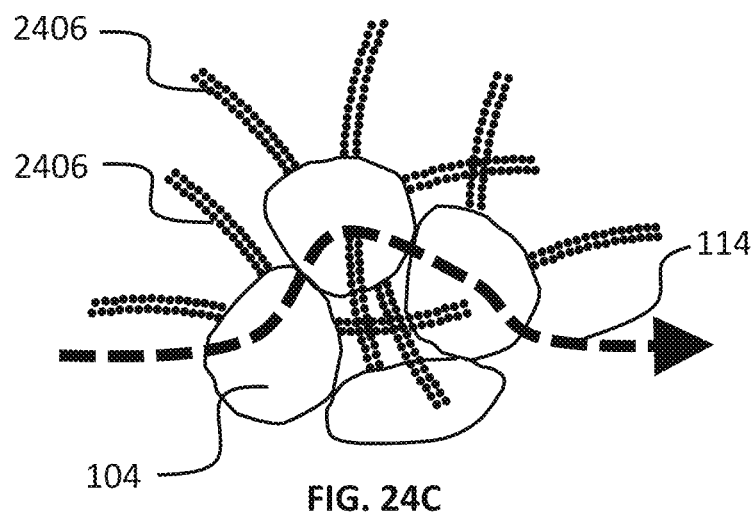

FIGS. 24A-24C illustrate an exemplary embodiment in which target DNA is captured on $MO_x$ structures 104 and amplified. FIG. 24A illustrates one method of capturing a target nucleic acid, here DNA molecule 2403, on $MO_x$ structures 104 using a nucleic acid comprising a first common sequence 2402 that is complementary to some portion of target DNA molecule 2403. In some embodiments, the portion of target DNA molecule 2403 that is complementary to common sequence 2402 may have been previously ligated or otherwise joined to target DNA 2403. In some embodiments a sensor response profile can be determined with a liquid sample, using an apparatus 100 with a porous conductive film 103 comprising $MO_x$ structures 104 having nucleic acids, comprising common sequence 2402, attached to the structures and hybridized to target DNA molecule 2403. In some aspects, the determined sensor response profile may be used as a control sensor response profile or may provide a baseline current level 114 for use when tracking changes to an electrical property of porous conductive film 103, such as for example when monitoring progress of a chemical reaction.

In some embodiments, a nucleic acid attached to $MO_x$ structures 104 and comprising common sequence 2402 may be used to prime nucleic acid synthesis in a nucleic acid amplification reaction, such as a reaction that is performed for purposes of amplifying the number of target DNA molecules 2403 that are attached to MOx structures 104. FIG. 24B illustrates an embodiment in which MOx structures 104 comprise attached target DNA molecules 2403 following amplification of the captured molecules. In some embodiments, during an amplification reaction, reaction chemicals (e.g., reaction components, products and by-products) may adsorb to and desorb from the surfaces of MOx structures 104, which can result in changes to electrical conductivity 114 of porous conductive film 103 that can be detected and measured for determining reaction progress.

FIG. 24C illustrates double stranded nucleic acids (2406) attached to MOx structures 104 following nucleic acid extension using nucleic acids comprising common sequence 2402 (FIG. 24B) as extension primers. In this embodiment, as for those depicted in FIGS. 24A-B, changes to electrical conductivity 114 of porous conductive film 103 can be detected and measured for determining reaction progress.

In some embodiments, differences between the interaction of $MO_x$ structures 104 with a first species of molecule or ion analyte and the interaction of $MO_x$ structures 104 with a second species of ion or molecule analyte 112 may occur for reasons other than differences in diffusion rates of ion or molecule analytes 112 and may account for differential detection of the first and second species by different electrode pairs 102. By way of example, the affinities of the first and second species of analytes 112 for $MO_x$ structures 104 in a porous conductive film 103 may be different. In some aspects, a first species of analyte may have a higher affinity for $MO_x$ structures 104 than does a second species of analyte. In some aspects, the first species of analyte having a higher affinity for MOx structures 104 in a region of porous conductive film 103 may outcompete a second species of analyte for interacting with the $MO_x$ structures. By way of analogy, such competition may occur during a sample loading phase (e.g., self displacement chromatography) and during the displacement phase of displacement chromatography, which is known to those having skill in the art.

Figure 25A:
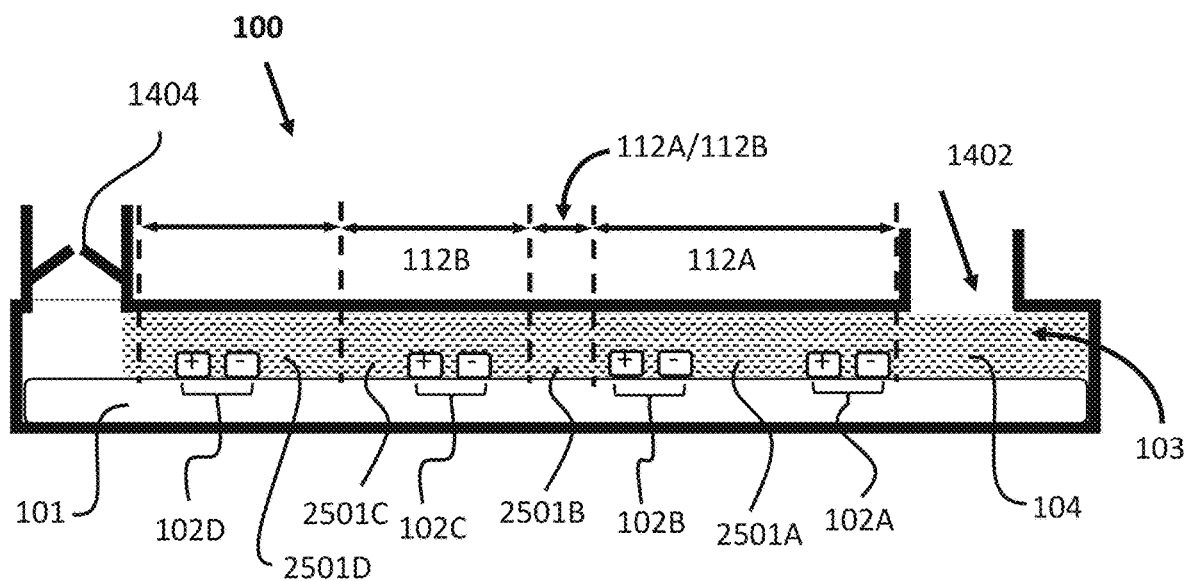
FIGS. 25A-25B illustrate a schematic depiction of an exemplary apparatus having four electrode pairs operably connected to a porous conductive film and configured for lateral sample flow and four sensor response profiles that may be determined during analysis of molecule and ion species having different binding affinities for metal oxide structures.
Figure 25B:
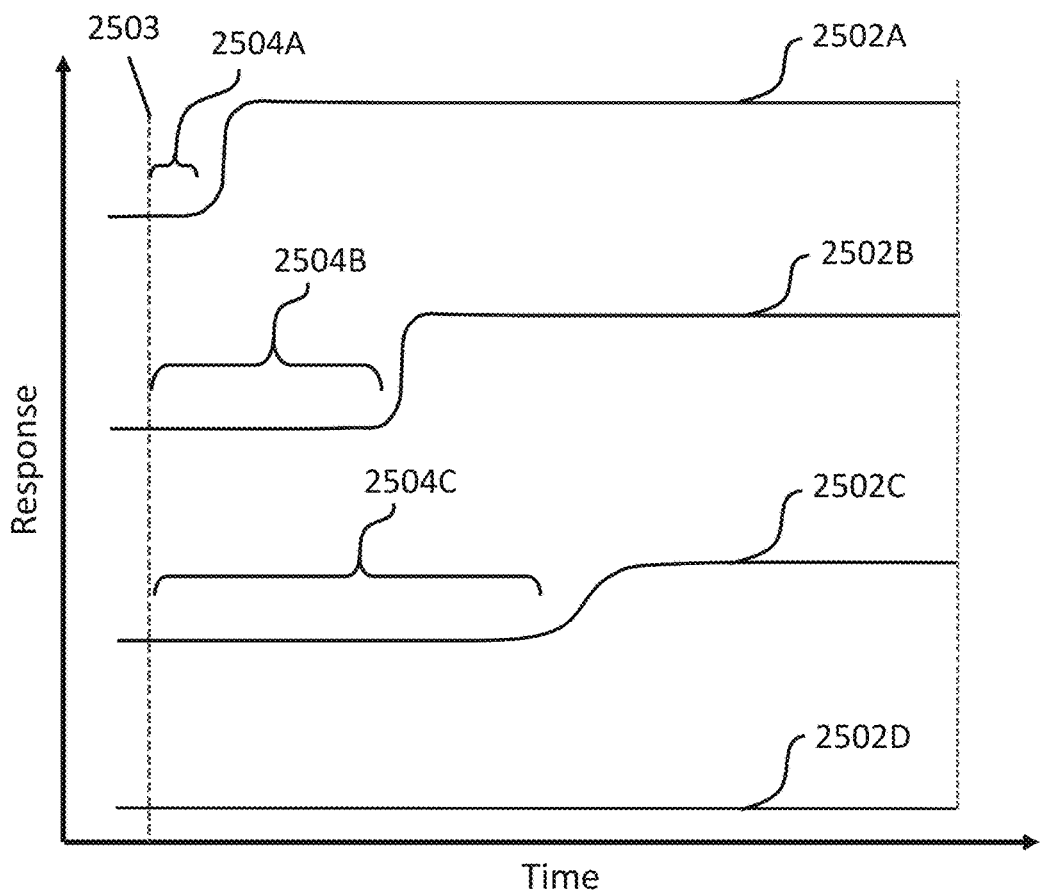

FIG. 25A illustrates a schematic depiction of an exemplary embodiment of an apparatus having four electrode pairs 102A-102D pairs of electrodes operably connected to porous conductive film 103 and configured for lateral sample flow. FIG. 25B illustrates four sensor response profiles 2502A-2502D that may be determined with electrode pairs 102A-102D, respectively, during analysis of ion or molecule species having different binding affinities for metal oxide structures 104 in a porous conductive film 103. In this exemplary embodiment, measurements of an electrical property of porous conductive film 103 can begin at time point $t_0$ represented by vertical line 2503. In this embodiment, test sample liquid diffusing from sample reservoir 1402 through the interstitial liquid in porous conductive film 103 to outlet port 108 may traverse electrode pairs 102A-D at different times, and an initial response of each sensor to an ion or molecule analyte 112 may occur at different times, illustrated as the amount of time spanning regions 2504A-C, respectively, or a response may not be detected. In embodiments, in which a liquid test sample comprises a plurality of ion or molecule analytes 112 that have different binding affinities for $MO_x$ structures 104, an initial response of each sensor to an ion or molecule analyte, if detected, may occur at different times.

By way of example, a first analyte species 112A may have a higher binding affinity for $MO_x$ structures 104 than does a second analyte species 1128. As wicking of a test or control sample liquid that is added to sample reservoir 1402 progresses toward outlet port 108, analyte species 112A may interact with porous conductive film 103 nearer to electrode pairs 102A and 102B forming a region 2501A (between dashed lines) of porous conductive film 103 where "higher binding affinity" analyte species 112A outcompetes "lower binding affinity" analyte 112B for interacting with or binding to $MO_x$ structures 104, at equilibrium. Sensor response profile 2502A represents the electrical response of porous conductive film 103 that may be detected by electrode pair 102A to high binding analyte species 112A, with an initial response occurring after a time period 2504A. Response profile 2502B represents the electrical response of porous conductive film 103 that may be detected by electrode pair 102B to "higher binding affinity" analyte species 112A, with an initial response occurring after a time period 2504B. For a selected length 1406, width 1408, and thickness 1407 of porous conductive film 103, the time to initial response of porous conductive film 103 to ion or molecule analyte species 112A and the detection of a response by a given electrode pair 102A-102D at a selected distance from sample reservoir 1402, or lack of detection thereof, can be affected by a variety of factors, including by way of example, the amount and concentration of an analyte 112 in a test sample, the volume of test sample added to reservoir 1402, and the availability of binding or interaction sites on $MO_x$ structures 104.

In this exemplary embodiment, the molar amount of "higher binding affinity" analyte species 112A in a sample aliquot that can be added to sample reservoir 1402 is equal to the molar quantity of available interaction or binding sites on $MO_x$ structures 104 in a section of porous conductive film 103 including 2501A and at least part of region 2501B (lying between electrode pairs 102B and 102C). Also in this example, "lower binding affinity" analyte species 112B that may have been prevented from interacting or binding to $MO_x$ structures 104 due to the presence of "higher binding affinity" analyte species 112A can be transported by fluid flow, wicking, or diffusion across electrode pairs 102A and 102B and begin interacting or binding with $MO_x$ structures in region 2501B of porous conductive film 103 between electrode pairs 102B and 102C. As such, region 2501B represents a section of porous conducting film 103 in which both analyte species 112A and 112B can bind to $MO_x$ structures 104. As the amount of ion or molecule analyte species 112A decreases to essentially zero in the liquid sample, only the remaining analyte species 112B interacts with or binds to $MO_x$ structures 104 forming a region 2501C of porous conductive film 103 having only "lower binding affinity" analyte species 112B. Response profile 2502C represents the electrical response of porous conductive film 103 that may be detected by electrode pair 102C to low binding affinity species 112B, with an initial response occurring after a time period 2504C. As the amount of ion or molecule analyte species 112B decreases to essentially zero in the liquid sample, as in region 2501D, no further change in the electrical response of porous conductive film 103 is detected by electrode pair 102D, as indicated by the unchanging sensor response profile 2502D.

In another example, the addition of new liquid sample comprising solvated ions or molecules with higher binding affinity than species 112A into sample reservoir 1402 flowing or diffusing toward outlet port 108 through porous conductive film 103 may cause "higher binding affinity" species 112A ions or molecules to be displaced and move from region 2501A into regions 2501B and 2501C. In some aspects, this may result in a competitive displacement of "lower binding affinity" species 112B from $MO_x$ structures 104 and binding or interaction of higher binding affinity species 112A to the $MO_x$ structures 104, which may result in a change in the electrical response of porous conductive film 103 that can be detected by electrode pair 102C. As a result, competitive displacement of bound ions or molecules may occur in additional regions of porous conductive film 103 further from inlet port 107 and closer to outlet port 108.

In yet another example, such as during the monitoring of a chemical reaction using an apparatus 100, "higher binding affinity" species 112A that is a reaction product may accumulate during a chemical reaction resulting in an increase in the number of the "higher binding affinity" ion or molecule analyte species 112A that are bound to or interacting with $MO_x$ structures 104. In a lateral flow assay this may result in an increase in the size (length) of a region porous conductive film 103 having bound ion or molecule reaction products, which may subsequently result in a change of the electrical property of the porous conductive film 103 that can be detected by electrode pairs 102 positioned further from sample reservoir 1402. The distance of the electrode pair measuring the change from sample reservoir 1402 may be correlated to the number of bound reaction product ions or molecules and to the progress of the chemical reaction.

In some embodiments, the affinities of different species of molecules and ions for $MO_x$ structures may be affected by one or more of a plurality of factors. By way of example, in some embodiments, the type or types of $MO_x$ structures 104 present in porous conductive film 103 may interact differently with different species of analytes 112 or with other ion or molecule analyte species 112 present in submersion liquid 106. ions and/or molecules present in submersion liquid 106 may interact with $MO_x$ structures and affect sensor response to ion and/or molecule analytes 112 of interest. For example, in some aspects, a submersion liquid 106 may be a buffer solution and may comprise ions and/or molecules that include a weak acid and its conjugate base. These acidic and basic ionic species may interact with $MO_x$ structures 104 and as a result may affect the space charge region of the $MO_x$ structures 104. In some aspects, space charge region differences in $MO_x$ structures 104 may affect sensor response to the ion or molecule analyte species 112 of interest. In another exemplary aspect, the presence of a plurality of different ion or molecule analyte species 112 in a test sample added to a submersion liquid 106 may affect the interaction of analytes 112 with $MO_x$ structures 104 thereby affecting the sensor response to the analytes 112.

In some aspects, solvation of one or more species of ions or molecules by the submersion liquid 106 may affect the rate of diffusion of the ion or molecule to the $MO_x$ structures 104, the adsorption of the molecule or ion to the $MO_x$ structures, and the desorption of ions or molecules from the $MO_x$ structures. One or more of these phenomenon may affect sensor response to ion and molecule analytes 112 of interest and may affect the sensor response as determined by different electrode pairs 102.

In some embodiments, the composition of one or more of the submersion liquid 106, sample (test or control) liquid, and any other liquid that may be added to a sensor chamber or chambers during sensor operation may be selected so as to influence the interaction of one or more species of ions or molecules with $MO_x$ structures 104. In some aspects, influencing the interaction of ions or molecules may include one or more of enhancing or inhibiting interaction of selected species with $MO_x$ structures 104, thereby modulating sensor response. In some aspects modulation of sensor response by adjusting the composition of one or more of the liquids may enhance detection and quantification of one or more analyte 112 in a test sample and may enhance discrimination of analytes 112 in a test sample.

What is claimed is:

1. An apparatus for use in detecting molecules and ions comprising:
   (a) a housing defining a chamber, the chamber having a liquid therein;
   (b) a sensor submerged in the liquid and comprising,
      (i) a porous conductive film positioned on a substrate and made of chemiresistive semiconducting metal oxide structures, and
      (ii) a pair of electrodes operably connected to the porous conductive film for generating electric current in the film between the electrodes and for detecting a change in an electrical property of the film.

2. The apparatus of claim 1 wherein the sensor is equilibrated in the liquid.

3. The apparatus of claim 1 wherein the chemiresistive semiconducting metal oxide structures comprise either or both of nanostructures and microstructures.

4. The apparatus of claim 1 wherein the liquid is an aqueous liquid comprising either or both of solvated molecules and solvated ions.

5. The apparatus of claim 4 wherein some of the either or both of solvated molecules and solvated ions are organic molecules.

6. The apparatus of claim 4 wherein some of the either or both of solvated molecules and solvated ions are adsorbed to the porous conductive film.

7. The apparatus of claim 4 wherein the aqueous liquid is a buffer solution comprising a mixture of a weak acid and its conjugate base.

8. The apparatus of claim 4 wherein some of the either or both of solvated molecules and solvated ions are analytes.

9. The apparatus of claim 1 further comprising a first inlet port that provides for fluid communication with the chamber.

10. The apparatus of claim 9 further comprising a second inlet port that provides for fluid communication with the chamber.

11. The apparatus of claim 9 further comprising a wicking material that effects the transport of either or both of ions and molecules across one or more electrode pairs.

12. The apparatus of claim 9 further comprising a first outlet port.

13. The apparatus of claim 11 wherein the wicking material effects the transport of either or both of ions and molecules through the porous conductive film.

14. The apparatus of claim 12 further comprising a semipermeable barrier that divides the chamber into a first subchamber and a second subchamber, wherein the sensor is positioned in the first subchamber, and wherein the first inlet port and first outlet port are configured to provide for fluid communication with the second subchamber.

15. The apparatus of claim 14 further comprising a second inlet port and a second outlet port, wherein the second inlet port and the second outlet port are configured to provide for fluid communication with the first subchamber.

16. The apparatus of claim 14 wherein the semipermeable barrier is in contact with the porous conductive film.

17. The apparatus of claim 14 wherein the semipermeable barrier comprises a plurality of semipermeable membranes.

18. The apparatus of claim 1 wherein the sensor comprises a plurality of electrode pairs operably connected to and positioned at selected spaced-apart locations along the porous conductive film.

19. The apparatus of claim 18 wherein the electrodes of at least one electrode pair are positioned on opposing sides of the chamber.

20. The apparatus of claim 18 further comprising a first inlet port that provides for fluid communication with the chamber and wherein the first inlet port is configured as a wicking material.

21. The apparatus of claim 20 wherein the wicking material is configured for controlling the wicking rate of a sample liquid across the porous conductive film.

22. The apparatus of claim 18 wherein some of the chemiresistive semiconducting metal oxide structures are derivatized with a diffusion matrix that interacts non-specifically with either or both of ion analytes and molecule analytes.

23. The apparatus of claim 22 wherein the derivatized chemiresistive semiconducting metal oxide structures are positioned between two selected electrode pairs of the plurality of electrode pairs.

24. A method for quantifying one or more ion or molecule analytes in a liquid sample, using the apparatus of claim 18, the method comprising:
   (a) exposing the sensor to the liquid sample;
   (b) generating an electric current in the porous conductive film at each electrode pair in the plurality of electrode pairs;
   (c) measuring an electrical property of the porous conductive film at each electrode pair;
   (d) identifying a change in the measured electrical property of the porous conductive film at each electrode pair; and
   (e) quantifying the one or more ion or molecule analytes based on the binding capacity for the one or more ion or molecule analytes of a selected mass of MOx structures and the measured electrical property of the porous conductive film at each electrode pair.

25. A method for detecting an ion or molecule analyte in a liquid sample using the apparatus of claim 1, the method comprising:
   (a) exposing the sensor to the liquid sample,
   (b) generating an electric current in the porous conductive film and measuring an electrical property of the porous conductive film for a selected period of time ranging from before exposing the sensor to the liquid sample to a selected period of time after exposing the sensor to the liquid sample;
   (c) identifying a change in the measured electrical property of the porous conductive film; and
   (d) correlating the change in the measured electrical property with the presence of a molecule or ion in the liquid sample.

26. A method for monitoring a nucleic acid polymerization reaction using the apparatus of claim 1, the method comprising:
- (a) exposing the sensor to the nucleic acid polymerization reaction;
- (b) generating an electric current in the porous conductive film and measuring an electrical property of the porous conductive film for a selected period of time;
- (c) identifying a change in the measured electrical property of the porous conductive film;
- (d) identifying a nucleotide incorporated into the nucleic acid based on the interaction of a plurality of reaction products with the porous conductive film; and
- (e) identifying a sequence of the nucleic acid based on the identity of the incorporated nucleotide.

* * * * *